US011857638B2

(12) United States Patent
Zhou et al.

(10) Patent No.: US 11,857,638 B2
(45) Date of Patent: Jan. 2, 2024

(54) QUINONE-CONTAINING CONJUGATES

(71) Applicant: PROMEGA CORPORATION, Madison, WI (US)

(72) Inventors: Wenhui Zhou, San Luis Obispo, CA (US); Hui Wang, San Luis Obispo, CA (US); James J. Cali, Verona, WI (US); Sarah Duellman, Madison, WI (US); Jolanta Vidugiriene, Madison, WI (US); Natasha Karassina, Madison, WI (US)

(73) Assignee: PROMEGA CORPORATION, Madison, WI (US)

( * ) Notice: Subject to any disclaimer, the term of this patent is extended or adjusted under 35 U.S.C. 154(b) by 1019 days.

(21) Appl. No.: 16/523,384

(22) Filed: Jul. 26, 2019

(65) Prior Publication Data

US 2020/0030456 A1 Jan. 30, 2020

Related U.S. Application Data

(60) Provisional application No. 62/711,328, filed on Jul. 27, 2018.

(51) Int. Cl.

| | |
|---|---|
| ***A61K 31/122*** | (2006.01) |
| ***C07D 417/12*** | (2006.01) |
| ***C07K 16/30*** | (2006.01) |
| ***A61P 35/00*** | (2006.01) |
| ***A61K 47/68*** | (2017.01) |
| ***G01N 33/58*** | (2006.01) |
| ***A61K 49/00*** | (2006.01) |

(52) U.S. Cl.

CPC ........ *A61K 47/6889* (2017.08); *A61K 31/122* (2013.01); *A61K 47/6891* (2017.08); *A61K 49/0039* (2013.01); *A61K 49/0043* (2013.01); *A61K 49/0052* (2013.01); *C07D 417/12* (2013.01); *C07K 16/30* (2013.01); *G01N 33/582* (2013.01)

(58) Field of Classification Search

CPC .... A61K 31/122; C07D 417/12; C07K 16/30; A61P 35/00

See application file for complete search history.

(56) References Cited

U.S. PATENT DOCUMENTS

| | | | | |
|---|---|---|---|---|
| 7,829,531 | B2 | 11/2010 | Senter et al. | |
| 9,242,013 | B2 | 1/2016 | Howard et al. | |
| 2002/0119305 | A1 | 8/2002 | Mrksich et al. | |
| 2008/0248511 | A1 | 10/2008 | Daily et al. | |
| 2008/0279868 | A1 | 11/2008 | Boyd et al. | |
| 2011/0256157 | A1 | 10/2011 | Howard et al. | |
| 2012/0117667 | A1 | 5/2012 | Klaubert et al. | |
| 2015/0307916 | A1 | 10/2015 | Zhou et al. | |
| 2021/0000769 | A1* | 1/2021 | Phanstiel, IV ....... | A61K 31/165 |
| 2022/0249421 | A1* | 8/2022 | Kelley ................ | A61K 31/201 |

FOREIGN PATENT DOCUMENTS

| | | |
|---|---|---|
| NO | 2014193722 | 12/2014 |
| WO | 2003040100 | 5/2003 |
| WO | 2004103272 | 12/2004 |
| WO | 2014194247 | 12/2014 |
| WO | 2015116867 | 8/2015 |

OTHER PUBLICATIONS

International Search Report and Written Opinion, International Patent Application No. PCT/US2019/043655, dated Nov. 4, 2019, 13 pages.

Hamann "Monoclonal antibody-drug conjugates" Expert Opin. Ther. Patents 2005, 15(9), 1087-1103.

Liu et al. "Antibody-drug conjugates for non-oncological indications" Expert Opin. Biol. Th. (2016) 16(5), 591-593.

De Carvalho et al. "Siderophores as 'Trojan Horses': tackling multidrug resistance?" Front. Microbiol. (2014), 5 (290) doi 10.3389/fmicb.2014.00290.

Starr et al. "Siderophore Receptor-Mediated Uptake of Lactivicin Analogues in Gram-Negative Bacteria" J. Med. Chem. (2014) 57, 3845-3855.

Miller et al., "The design, synthesis and study of siderophore-antibiotic conjugates Siderophore mediated drug transport" Biol. Met. (1991) 4(1), 62-69.

Casi et al. "Antibody-Drug Conjugates and Small Molecule-Drug Conjugates: Opportunities and Challenges for the Development of Selective Anticancer Cytotoxic Agents" J. Med. Chem. (2015) 58 (22), 8751-8761.

Srinivasarao et al. "Principles in the design of ligand-targeted cancer therapeutics and imaging agents" Nat. Rev. Drug Discov. (2015) 14, 203-219.

Zheng et al. "A Redox-Sensitive Resin Linker for the Solid Phase Synthesis of C-Terminal Modified Peptides" J. Org. Chem. (1999) 64(1), 156-161.

Jain et al. "Current ADC Linker Chemistry" Pharm. Res. (2015) 32, 3526-3540.

Ducry et al. "Antibody-Drug Conjugates: Linking Cytotoxic Payloads to Monoclonal Antibodies" Bioconjugate Chem. (2010) 21, 5-13.

Seattle Genetics "Antibody-Drug Conjugates (ADSs)" Oct. 2012, 12 pages.

Mustafa et al., "Novel No-Wash Luminogenic Probes for the Detection of Transporter Uptake Activity" Bioconjugate Chem. 2016, 27:87-101.

* cited by examiner

*Primary Examiner* — Sun Jae Yoo

(74) *Attorney, Agent, or Firm* — Casimir Jones, S.C.; Anne M. Reynolds

(57) ABSTRACT

Conjugates comprise a drug or probe, a cell binding agent, and a quinone-containing linker. The quinone-containing linker may be reduced intracellularly to trigger release of the drug or probe. These conjugates may selectively deliver a drug or probe to a site of action of interest for local release of the active drug or probe.

31 Claims, 3 Drawing Sheets

QUINONE-CONTAINING CONJUGATES

CROSS-REFERENCE TO RELATED APPLICATIONS

This application claims the priority benefit of U.S. Provisional Patent Application Ser. No. 62/711,328, filed on Jul. 27, 2018, which is incorporated herein by reference in its entirety.

TECHNICAL FIELD

The present disclosure relates generally to conjugates, compounds, compositions, and methods of using the conjugates, compounds, and compositions including detection and/or treatment of proliferative disorders.

BACKGROUND

Antibody Drug Conjugates (ADCs) are designed to selectively target and destroy tumor cells. They are assembled by connecting a cytotoxic molecule known as the payload, generally an antimitotic agent, by way of a linker to an antibody that selectively binds an antigen on the targeted tumor cells. Bound ADCs are taken up by target cells via endocytosis and delivered to lysosomes for degradation where the cytotoxic payload is released and kills the tumor cells.

Linker chemistries currently in use for ADCs are described as cleavable or non-cleavable. Cleavable forms incorporate a specific release mechanism that is triggered inside of target cells. These include hydrazone, disulfide, pyrophosphate diester, and peptide linkers. The best-known peptide linkers are cathepsin B substrates with an aminobenzyloxycarbonyl group that facilitates traceless payload elimination after proteolytic cleavage. Non-cleavable forms release payloads after non-specific cleavage/degradation in the cytosol and lysosomes. This mechanism can result in heterogeneous linker cleavage that delivers payloads with variable potencies due to residual linker atoms. While there has been some success with this approach, the heterogeneous pool of released payload molecules contributes a substantial degree of complexity in pharmacokinetics/pharmacodynamics (PK/PD) and absorption-distribution-metabolism-excretion (ADME)/toxicity properties. Furthermore, stability of an ADC in the blood stream is critical for avoiding off target toxicity due to payload release in the circulation. This has been a problem for hydrazone and disulfide linked ADCs, but is improved with non-cleavable linkers. There is a need therefore for novel linker chemistries with improved properties to increase the options available for ADC design and development with potential to enable ideal ADC designs for certain targets.

SUMMARY

The present invention relates to conjugates where a drug or a probe and a cell-binding agent (e.g., antibody) are linked through a quinone-containing linker. These conjugates may selectively deliver cytotoxins to a site of action of interest for local release of the active drug. The quinone-containing linker may be reduced in situ to trigger release of the cytotoxic drugs.

In one aspect, provided are conjugates of formula (I), or a salt thereof, $$Cb\text{-}(G)_p \quad (I)$$

wherein

Cb is a cell-binding moiety;

p is a number from 1 to 20;

G is formula (II), (III), or (IV)

(II)

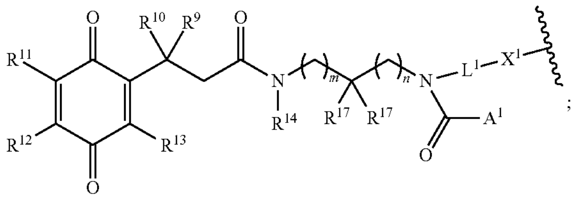

(III)

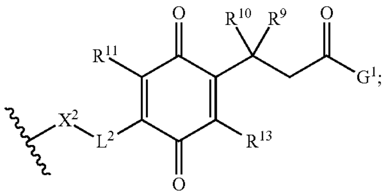

(IV)

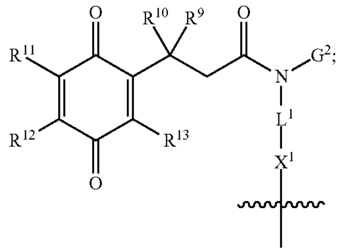

$R^9$ and $R^{10}$ are each independently selected from $C_{1-4}$alkyl;

$R^{11}$, $R^{12}$, and $R^{13}$ are each independently H, $C_{1-4}$alkyl, $C_{1-4}$alkoxy, bromo, chloro or amino, or $R^1$ and $R^{12}$ in formula (II) or (IV), together with the atoms to which they are attached form a fused phenyl ring;

$L^1$ is a first linker moiety;

$L^2$ is a second linker moiety;

$G^1$ is $-A^2$,

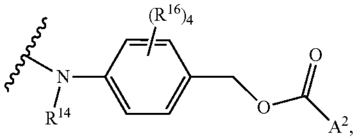

or

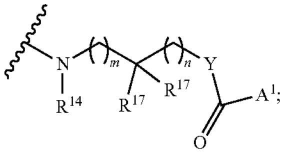

$G^2$ is

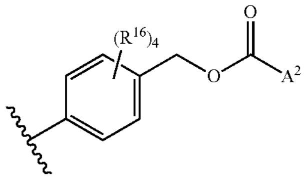

or

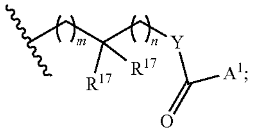

$X^1$ and $X^2$ are each an antibody-linking moiety;

Y is O or $NR^{15}$;

$R^{14}$ and $R^{15}$ are each independently H, $C_{1-30}$alkyl optionally substituted with 1-8 halogens, —$C_{1-30}$alkylene-OH, —$C_{1-30}$alkylene-$C_{1-4}$alkoxy, —$C_{1-30}$alkylene-COOH, or —$C_{1-30}$alkylene-amido;

$R^{16}$, at each occurrence, is independently H, halogen, $CH_3$, $OCH_3$, or $NO_2$;

$R^{17}$, at each occurrence, is independently H or $C_{1-4}$alkyl or both $R^{17}$ together with the carbon to which they are attached form a cycloalkyl ring having from 3-7 carbons;

m is an integer from 0-2;

n is an integer from 0-2;

$A^1$ is a payload moiety bonded through a substitutable oxygen or sulfur atom; and $A^2$ is a payload moiety bonded through a substitutable oxygen, sulfur, or nitrogen atom.

Another aspect provides compounds of formula 7, or a salt thereof,

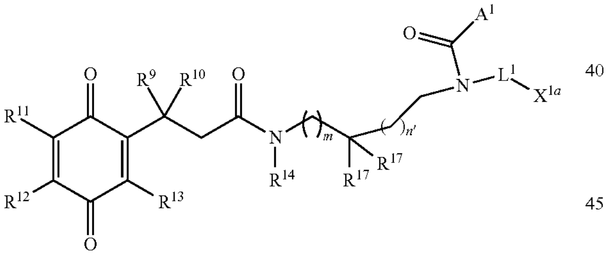

wherein $R^9$ and $R^{10}$ are each independently selected from $C_{1-4}$alkyl;

$R^{11}$, $R^{12}$, and $R^{13}$ are each independently H, $C_{1-4}$alkyl, $C_{1-4}$alkoxy, bromo, chloro or amino, or $R^1$ and $R^{12}$ together with the atoms to which they are attached form a fused phenyl ring;

$L^1$ is a first linker moiety;

$X^{1a}$ is —$OS_2R^{50}$, OH, —Cl, —Br, —I, —$N_3$, —C≡CH, —CN, COOH, —$COOR^{40}$, —$COJ^1$, —$CH(SO_3H)$—$C(O)OR^{40}$, —NCO, —NCS, —$C(O)CH_2J^1$,

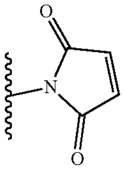 , 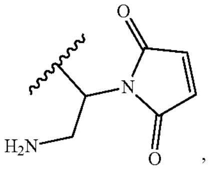 ,

-continued

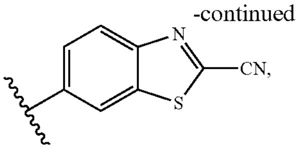

—$NH_2$, or —$NH(C_{1-6}alkyl)$;

$R^{40}$ is $C_{1-6}$alkyl, 4-nitrophenyl, pentafluorophenyl, tetrafluorophenyl, —C(O)—$OR^{41}$, or

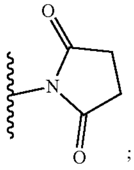 [SMILES: *N1C(=O)CCC1=O]

;

$R^{41}$ is $C_{1-6}$alkyl or phenyl; $J^1$ is —Cl, —Br, —I, or —$OSO_2R^{50}$;

$R^{50}$ is $C_{1-6}$alkyl, $C_{1-6}$haloalkyl, phenyl, 4-methylphenyl, 4-nitrophenyl, or 4-bromophenyl;

$R^{14}$ is H, $C_{1-30}$alkyl optionally substituted with 1-8 halogens, —$C_{1-30}$alkylene-OH, —$C_{1-30}$alkylene-$C_{1-4}$alkoxy, —$C_{1-30}$alkylene-COOH, or —$C_{1-30}$alkyleneamido;

$R^{17}$, at each occurrence, is independently H or $C_{1-4}$alkyl or both $R^{17}$ together with the carbon to which they are attached form a cycloalkyl ring having from 3-7 carbons;

m is an integer from 0-2;

n' is 0 or 1; and $A^1$ is a payload moiety bonded through a substitutable oxygen or sulfur atom.

Another aspect provides compounds of formula 10, or a salt thereof,

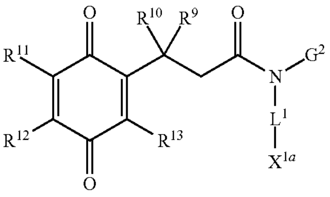

10 wherein $R^9$ and $R^{10}$ are each independently selected from $C_{1-4}$alkyl;

$R^{11}$, $R^{12}$, and $R^{13}$ are each independently H, $C_{1-4}$alkyl, $C_{1-4}$alkoxy, bromo, chloro or amino, or $R^1$ and $R^{12}$ together with the atoms to which they are attached form a fused phenyl ring;

$L^1$ is a first linker moiety;

$G^2$ is

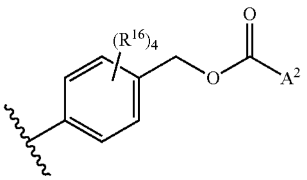

or

-continued

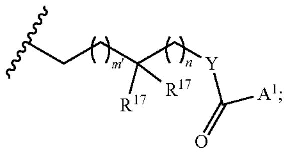

Y is O or $NR^{15}$;

$R^{15}$ is each independently H, $C_{1-30}$alkyl optionally substituted with 1-8 halogens, —$C_{1-30}$ alkylene-OH, —$C_{1-30}$alkylene-$C_{1-4}$alkoxy, —$C_{1-30}$alkylene-COOH, or —$C_{1-30}$alkylene-amido;

$R^{16}$, at each occurrence, is independently H, halogen, $CH_3$, $OCH_3$, or $NO_2$;

$R^{17}$, at each occurrence, is independently H or $C_{1-4}$alkyl or both $R^{17}$ together with the carbon to which they are attached form a cycloalkyl ring having from 3-7 carbons;

$X^{1a}$ is —$OSO_2R^{50}$, OH, —Cl, —Br, —I, —$N_3$, —C≡CH, —CN, COOH, —$COOR^{40}$, —$COJ^1$, —$CH(SO_3H)$—$C(O)OR^{40}$, —NCO, —NCS, —$C(O)CH_2J^1$,

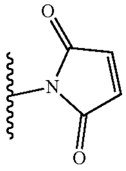 , 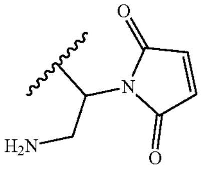 ,

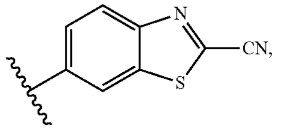

—$NH_2$, or —$NH(C_{1-6}alkyl)$;

$R^{40}$ is $C_{1-6}$alkyl, 4-nitrophenyl, pentafluorophenyl, tetrafluorophenyl, —C(O)—$OR^{41}$, or

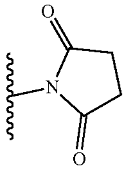 ;

$R^{41}$ is $C_{1-6}$alkyl or phenyl;

$J^1$ is —Cl, —Br, —I, or —$OSO_2R^{50}$;

$R^{50}$ is $C_{1-6}$alkyl, $C_{1-6}$haloalkyl, phenyl, 4-methylphenyl, 4-nitrophenyl, or 4-bromophenyl;

m' is 0 or 1;

n is an integer from 0-2;

$A^1$ is a payload moiety bonded through a substitutable oxygen or sulfur atom; and $A^2$ is a payload moiety bonded through a substitutable oxygen, sulfur, or nitrogen atom.

Another aspect provides compounds of formula 12, or a salt thereof,

12

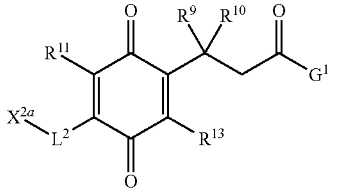

wherein $G^1$ is -$A^2$,

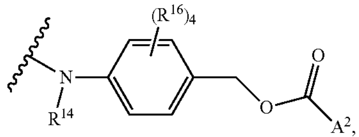 or

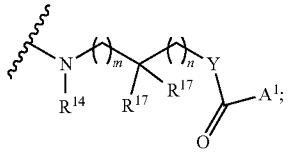

$R^9$ and $R^{10}$ are each independently selected from $C_{1-4}$alkyl;

$R^{11}$ and $R^{13}$ are each independently H, $C_{1-4}$alkyl, $C_{1-4}$alkoxy, bromo, chloro or amino;

$L^2$ is a second linker moiety; Y is O or $NR^{15}$;

$R^{14}$ and $R^{15}$ are each independently H, $C_{1-30}$alkyl optionally substituted with 1-8 halogens, —$C_{1-30}$alkylene-OH, —$C_{1-30}$alkylene-$C_{1-4}$alkoxy, —$C_{1-30}$alkylene-COOH, or —$C_{1-30}$alkyleneamido;

$R^{16}$, at each occurrence, is independently H, halogen, $CH_3$, $OCH_3$, or $NO_2$;

$R^{17}$, at each occurrence, is independently H or $C_{1-4}$ alkyl or both $R^{17}$ together with the carbon to which they are attached form a cycloalkyl ring having from 3-7 carbons;

m is an integer from 0-2;

n is an integer from 0-2;

$X^{2a}$ is —$OSO_2R^{50}$, OH, —Cl, —Br, —I, —$N_3$, —C≡CH, —CN, COOH, —$COOR^{40}$, —$COJ^1$, —$CH(SO_3H)$—$C(O)OR^{40}$, —NCO, —NCS, —$C(O)CH_2J^1$,

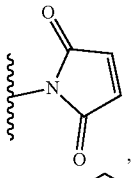 , 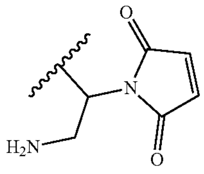 ,

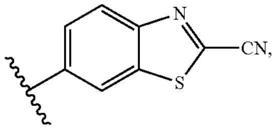

—$NH_2$, or —$NH(C_{1-6}alkyl)$;

$R^{40}$ is $C_{1-6}$alkyl, 4-nitrophenyl, pentafluorophenyl, tetrafluorophenyl, —C(O)—$OR^{41}$, or

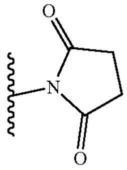

;

$R^{41}$ is $C_{1-6}$alkyl or phenyl;

$J^1$ is —Cl, —Br, —I, or —$OSO_2R^{50}$;

$R^{50}$ is $C_{1-6}$alkyl, $C_{1-6}$haloalkyl, phenyl, 4-methylphenyl, 4-nitrophenyl, or 4-bromophenyl;

$A^1$ is a payload moiety bonded through a substitutable oxygen or sulfur atom; and $A^2$ is a payload moiety bonded through a substitutable oxygen, sulfur, or nitrogen atom.

Another aspect provides compositions comprising a conjugate of formula (I), or a salt thereof, and a carrier.

Another aspect provides pharmaceutical compositions comprising a conjugate of formula (I), or a pharmaceutically acceptable salt thereof, and a pharmaceutically acceptable carrier.

Another aspect provides a method of treating a proliferative disorder comprising administering a therapeutically effective amount of a conjugate of formula (I), or a pharmaceutically acceptable salt or composition thereof, to a patient in need thereof. For example, the invention provides a method of killing a cell, wherein a conjugate compound of the invention is administered to the cell an amount sufficient to kill the cell.

In other aspects, disclosed is a method for evaluating cellular uptake of an agent comprising: a) contacting a sample comprising cells with a labeled agent, wherein the labeled agent is derived from an agent and a compound of formula (I); and b) detecting light emission, whereby the detection of light emission indicates cellular uptake of the agent.

Another aspect provides a kit comprising a conjugate of formula (I), or a pharmaceutically acceptable salt or composition thereof, and instructions for use.

Another aspect provides a kit comprising a compound of formula 7, or a salt or composition thereof, and instructions for use.

Another aspect provides a kit comprising a compound of formula 10, or a salt or composition thereof, and instructions for use.

Another aspect provides a kit comprising a conjugate of formula 12, or a salt or composition thereof, and instructions for use.

The compounds, compositions, methods, and processes are further described herein.

DETAILED DESCRIPTION

1. Definition of Terms

Figure 1:
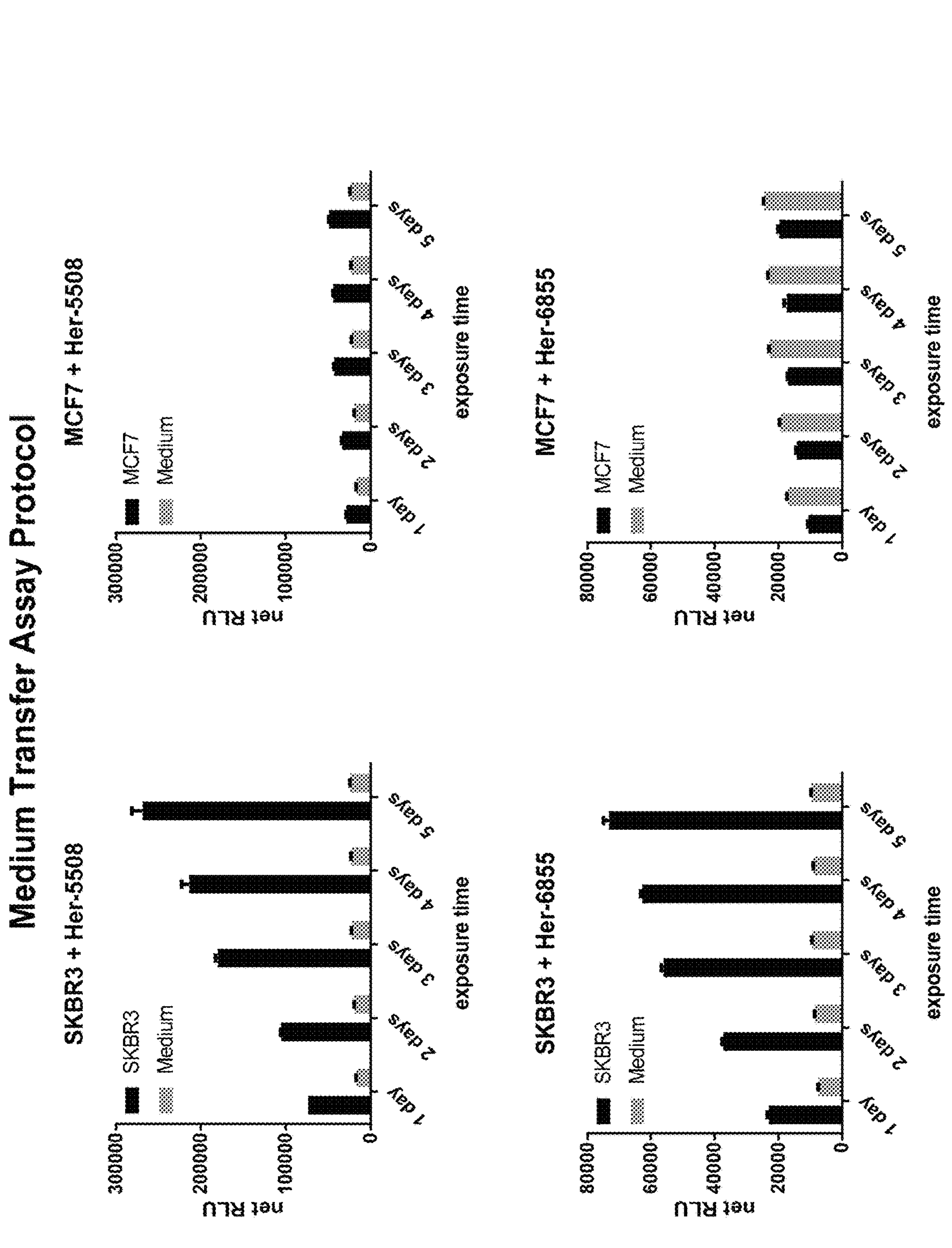
FIG. 1 shows luciferin luminescence (RLU=relative light unit) upon cellular release of luciferin from the Herceptin Conjugate of PBI-5508 or PBI-6855 in HER positive and negative cells (Example 7).

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms “comprise(s),” “include(s),” “having,” “has,” “can,” “contain(s),” and variants thereof, as used herein, are intended to be open-ended transitional phrases, terms, or words that do not preclude the possibility of additional acts or structures. The present disclosure also contemplates other embodiments “comprising,” “consisting of” and “consisting essentially of,” the embodiments or elements presented herein, whether explicitly set forth or not.

Terms such as “alkyl,” “cycloalkyl,” “alkylene,” etc. may be preceded by a designation indicating the number of atoms present in the group in a particular instance (e.g., “$C_{1-4}$alkyl,” “$C_{3-8}$cycloalkyl,” “$C_{1-6}$alkylene”). These designations are used as generally understood by those skilled in the art. For example, the representation “C” followed by a subscripted number indicates the number of carbon atoms present in the group that follows. Thus, “$C_3$alkyl” is an alkyl group with three carbon atoms (i.e., n-propyl, isopropyl). Where a range is given, as in “$C_{1-4}$,” the members of the group that follows may have any number of carbon atoms falling within the recited range. A “$C_{1-4}$alkyl,” for example, is an alkyl group having from 1 to 4 carbon atoms, however arranged.

As used herein, the term “alkenyl” refers to a straight or branched hydrocarbon chain containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

As used herein, the term “alkoxy” refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term “alkyl” refers to a linear or branched saturated hydrocarbon radical. Representative examples include methyl, ethyl, n-propyl, i-propyl, n-butyl, t-butyl, i-butyl, pentyl, and hexyl.

The term “alkylene,” as used herein, means a divalent group derived from a straight or branched chain saturated hydrocarbon. Representative examples of alkylene include, but are not limited to, —$CH_2$—, —$CH_2CH_2$—, —$CH_2CH_2CH_2$—, —$CH_2CH(CH_3)CH_2$—, and —$CH_2CH(CH_3)CH(CH_3)CH_2$—.

The term “alkenylene,” as used herein, means a divalent group derived from a straight or branched chain hydrocarbon containing at least one carbon-carbon double bond. Representative examples of alkenylene include, but are not limited to —CH=CH—, —$CH_2$CH=CH—, and —$CH_2$CH=CH($CH_3$)—.

As used herein, the term "alkynyl" refers to a straight or branched hydrocarbon radical having one or more carbon-carbon triple bonds. Alkynyl groups of the present invention include, but are not limited to, ethynyl, propynyl, and butynyl.

As used herein, the term "amido" refers to —$CONH_2$.

As used herein, the term "amino" refers to an —$NH_2$ group.

As used herein, the term "amino acid" refers to both natural and unnatural amino acids. It also includes protected natural and unnatural amino acids.

As used herein, the term "aryl" means phenyl or bicyclic aryl. The bicyclic aryl is naphthyl, dihydronaphthalenyl, tetrahydronaphthalenyl, indanyl, or indenyl. The phenyl and bicyclic aryls are attached to the parent molecular moiety through any carbon atom contained within the phenyl or bicyclic aryl.

As used herein, the term "phenylene" means a divalent phenyl radical, e.g., 1,4-phenylene ( 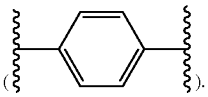 ).

As use herein, the term "azide" or "azido" refers to an —N═$N^+$═$N^-$ (i.e., —$N_3$) group.

As used herein, the term "derivative" may refer to a compound that is derived from a similar compound by some chemical or physical process. The derivative is a compound of similar chemical structure. The derivative may be a structural analogue.

As used herein, the term "carboxy" refers to a —C(O)—OH group.

The term "cycloalkyl" as used herein, means a saturated carbocyclic ring system containing zero heteroatoms as ring atoms, and zero double bonds. Examples of monocyclic cycloalkyls include, but are not limited to, cyclopropyl, cyclobutyl, cyclopentyl, cyclohexyl, cycloheptyl, and cyclooctyl. The cycloalkyl groups of the present invention may contain an alkylene bridge of 1, 2, 3, or 4 carbon atoms, linking two non-adjacent carbon atoms of the group. Examples of such bridged systems include, but are not limited to, bicyclo[2.2.1]heptanyl and bicyclo[2.2.2]octanyl. The cycloalkyl groups described herein can be appended to the parent molecular moiety through any substitutable carbon atom.

As used herein, the term "di(alkyl)amino" refers to two independently selected alkyl groups, as defined herein, appended to the parent molecular moiety through an amino group, as defined herein. Representative examples of di(alkyl)amino include, but are not limited to, N,N-dimethylamino, N-ethyl-N-methylamino, and N-isopropyl-N-methylamino.

As used herein, the term "halogen" or "halo" refers to a fluoro, chloro, bromo, or iodo radical.

As used herein, the term "haloalkoxy" refers to an alkoxy group, as defined herein, substituted by one, two, three, or four halogen atoms. Representative examples of haloalkoxy include, but are not limited to, chloromethoxy, 2-fluoroethoxy, trifluoromethoxy, and pentafluoroethoxy.

As used herein, the term "haloalkyl" refers to an alkyl group, as defined herein, substituted by one, two, three, or four halogen atoms. Representative examples of haloalkyl include, but are not limited to, chloromethyl, 2-fluoroethyl, trifluoromethyl, pentafluoroethyl, 2-chloro-3-fluoropentyl, and 4,4,4,-trifluorobutyl.

As used herein, the term "hydroxy" refers to an —OH group.

The term "linker" refers to a divalent chemical group or combination of divalent chemical groups, where the divalent groups may comprise rings or chains. The divalent chemical group(s) are composed of atoms or combinations of atoms connected by covalent bonds. Linkers (e.g., first and second linker moieties) connect separate chemical moieties such as, for example, connecting an antibody-linking moiety ($X^1$ or $X^2$) to the parent molecular moiety. Linkers are connected to an antibody-linking moiety and a parent molecular moiety by covalent bonds. The linker length may vary depending on the particular application. Generally, the first and second linker moieties contain at least a linear arrangement of from 2 to 50 atoms, through a combination of chain(s) and/or ring(s), where the linear arrangement may include side branching and/or substitution. The linkers may include one or more heteroatoms such as oxygen, nitrogen, sulfur, or phosphorus. Linkers may contain oxo groups, amino groups, alkyl groups, halogens and nitro groups. Linkers may also contain aryl groups. Exemplary divalent groups include —$C_{1-12}$alkylene-, —($C_{2-6}$alkylene-O)—$C_{1-6}$alkylene-, $C_{3-8}$cycloalkylene; —$C_{1-6}$alkylene-, —$C_{2-6}$alkylene-O—, $C_{3-8}$cycloalkylene, —C(O)—, —O—, —S—, —S(O)—, —$S(O)_2$—, —$NR^{20}$—, —$C(R^{21})$═N—NH—, —CH($CO_2H$)—,

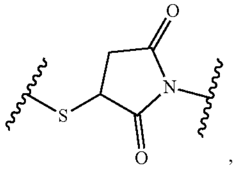 [SMILES: *SC1CC(=O)N(*)C1=O]

, an amino acid moiety, a protected amino acid moiety, and phenylene; wherein the $C_{3-8}$cycloalkylene and phenylene are optionally independently substituted with 1-4 substituents independently selected from the group consisting of $C_{1-4}$alkyl, $C_{1-4}$haloalkyl, $C_{1-4}$alkoxy, halo, cyano, and hydroxy; $R^{20}$ and $R^{21}$ at each occurrence are independently hydrogen or $C_{1-4}$alkyl; and x is an integer from 1 to 20. In some embodiments, a first or second linker moiety contains or consists of at least one of —$C_{1-12}$alkylene-, —($C_{2-6}$alkylene-O)$_x$—$C_{1-6}$alkylene-, or $C_{3-8}$cycloalkylene bonded to the parent molecular moiety, and optionally, one or more additional divalent moieties arranged to connect to the antibody linking moiety ($X^1$ or $X^2$), the one or more additional divalent moieties being selected from the group consisting of —$C_{1-6}$alkylene-, —$C_{2-6}$alkylene-O—, $C_{3-8}$cycloalkylene, —C(O)—, —O—, —S—, —S(O)—, —$S(O)_2$—, —$NR^{20}$—, —$C(R^{21})$═N—NH—, —CH($CO_2H$)—,

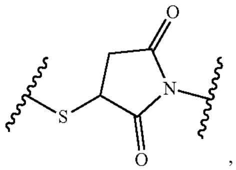 [SMILES: *SC1CC(=O)N(*)C1=O]

, an amino acid moiety, a protected amino acid moiety, and phenylene; wherein the $C_{3-8}$cycloalkylene and phenylene are optionally independently substituted with 1-4 substituents independently selected from the group consisting of $C_{1-4}$alkyl, $C_{1-4}$haloalkyl, $C_{1-4}$alkoxy, halo, cyano, and hydroxy; wherein x, $R^{20}$, and $R^{21}$ are as defined herein.

The linkers may be "traceless" or "self-immolative" linkers. The term "traceless linker" or "self-immolative linker" refers to a linker wherein biotransformation of a conjugate results in spontaneous cleavage of the linker from the parent molecular moiety.

Antibody linking moieties ($X^1$ or $X^2$) are divalent chemical groups bonded to the terminal end of a first or second linker moiety, respectively, and connect to a cell binding moiety (e.g. antibody moiety, small molecule drug moiety, polynucleotide). Exemplary antibody linking moieties include

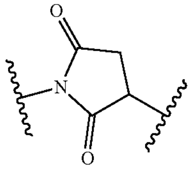
,
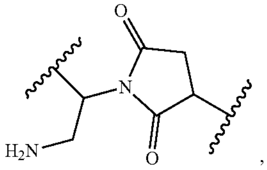
,

—C(O)$CH_2$—, —NHC(S)—, —NHC(O)—, —C(O)—, —CH($SO_3$H)—C(O)—,

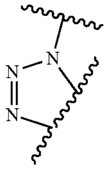
,
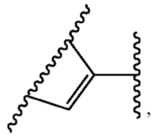
,

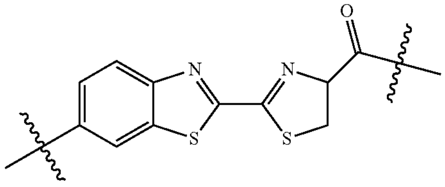
,

—NH—, or —N($C_{1-6}$alkyl)-. Antibody linking moieties may be bonded to Cb through N-terminal cysteine of Cb, through a sulfhydryl group (e.g., cysteine), through an amino (e.g., lysine, dUallylamine), through a carbonyl moiety (derived from a carboxyl in Cb), or through a ring formed by click chemistry (e.g., a triazole). For example, the antibody binding moiety

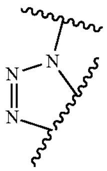

is bonded to

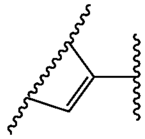

in an antibody to form a triazole moiety (e.g.,

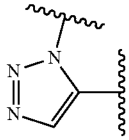
).

The triazole is formed by [3+2]cycloaddition of an azide to an alkyne, where the azide may originate from $X^{1a}/X^{2a}$ and the alkyne from the antibody, or vice versa.

The term "amino acid" refers to naturally occurring and synthetic/unnatural amino acids. Naturally occurring amino acids are those encoded by the genetic code as well as those amino acids that are later modified, e.g., hydroxyproline, γ-carboxyglutamate, and O-phosphoserine. For example, the term "natural amino acid" refers to any one of the common, naturally occurring L-amino acids found in proteins, including glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys), and methionine (Met). As used herein, the term "unnatural amino acid" refers to all amino acids that are not natural amino acids as described above. Such amino acids include the D-isomers of any of the naturally occurring amino acids described above. Unnatural amino acids also include homoserine, ornithine, norleucine, and thyroxine. Unnatural amino acids as part of a cell-binding agent may contain an alkyne or azide group capable of undergoing cycloaddition with a corresponding functional group at $X^{1a}/X^{2a}$ to form a triazole. Additional unnatural amino acids are well known to one of ordinary skill in the art. An unnatural amino acid may be a D- or L-isomer. An unnatural amino acid may also be an alpha amino acid or a beta amino acid. An unnatural amino acid may also be a post-translationally modified amino acid such as a phosphorylated serine, threonine or tyrosine, an acylated lysine, or an alkylated lysine or arginine. Many forms of post-translationally modified amino acids are known. One amino acid that may be used in particular is citrulline (cit), which is a precursor to arginine and is involved in the formation of urea in the liver.

In some embodiments, $L^{1b}$ or $L^{2b}$ comprise a peptide sequence cleavable by a protease expressed in tumor tissue. In some embodiments, a peptide sequence is selected from the group consisting of Val-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu, β-Ala-Leu-Ala-Leu, and Gly-Phe-Leu-Gly. In particular embodiments, a peptide sequence is Val-Cit or Val-Lys.

As used herein, the term "protected amino acid" refers to an amino acid side chain that additionally contains a protected functional group. Protecting groups are well known in the art and are intended to protect such functional groups as amino, hydroxy, thio, or carboxy against undesirable reactions during synthetic procedures. The protecting groups may be removed by a chemical reaction following the synthesis. Examples of protected amino acid side chains include benzyloxymethyl derived from serine, (4-methoxyphenyl)methyl derived from tyrosine, and tert-butylpropanoate derived from glutamate.

As used herein, the term “amino acid side chain” refers to the group attached to the co-carbon of an amino acid. It is the characterizing portion of an amino acid and is derived from a corresponding amino acid by elimination of the $NH_2CHC(O)OH$ moiety. For example, the amino acid side chain of alanine is methyl, and the amino acid side chain of phenylalanine is phenylmethyl. An amino acid side chain may be a natural amino acid side chain or an unnatural amino acid side chain. In some embodiments, an amino acid side chain may be a protected amino acid side chain.

As used herein, the term “amino protecting group” refers to a moiety that prevents chemical reactions from occurring on the nitrogen atom to which that protecting group is attached. An amino protecting group must also be removable by a chemical reaction. Such groups are well known in the art and include those described in detail in Protecting Groups in Organic Synthesis, T. W. Greene and P. G. M. Wuts, 3$^{rd}$ edition, John Wiley & Sons, 1999, the entirety of which is incorporated herein by reference. Suitable amino protecting groups include, but are not limited to, carbobenzyloxy (—NHCO—$OCH_2C_6H_5$ or —NH-Cbz); t-butyloxycarbonyl (—NHCO—$OC(CH_3)_3$ or —NH-Boc); 9-fluorenylmethyloxycarbonyl (—NH—Fmoc), 2,2,2-trichloroethyloxycarbonyl (—NH-Troc), and allyloxycarbonyl (—NH-Alloc). (In each of the above, the —NH— represents the nitrogen from the amino group that is being protected.)

As used herein, the term “amino blocking group” refers to a moiety that prevents chemical reactions from occurring on the nitrogen atom to which that blocking group is attached. In contrast to an amino protecting group, an amino blocking group is not intended to be removed by a chemical reaction. Such groups include, for example, acyl groups such as acetyl (—NHCO—$CH_3$) and succinyl (—NH—CO—$CH_2$—$CH_2$—COO—). (In each of the above, the —NH— represents the nitrogen from the amino group that is being blocked.)

As used herein, the term “nitrogen protecting group” refers to groups intended to protect an amino group against undesirable reactions during synthetic procedures. Representative nitrogen protecting groups include acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

As used herein, the term “oxo” refers to a double bonded oxygen (=O) radical.

The term “saccharide” refers to a sugar or other carbohydrate, especially a simple sugar. It includes both the alpha- and the beta-anomers. The saccharide can be a $C_6$-polyhydroxy compound, typically a $C_6$-pentahydroxy, and often a cyclic glycal. It includes the known simple sugars and their derivatives, as well as polysaccharides with two or more monosaccharide residues. The saccharide can include protecting groups on the hydroxyl groups. The hydroxyl groups of the saccharide can be replaced with one or more acetamido, halo or amino groups. Additionally, one or more of the carbon atoms can be oxidized, for example to keto or carbonyl groups. Suitable saccharides include galactose, glucose, glucuronic acid and neurominic acid.

As used herein, the term “sulfonyl” refers to $S(O)_2$.

A group is “substitutable” if it comprises at least one carbon or nitrogen atom that is bonded to one or more hydrogen atoms. Thus, for example, hydrogen, halogen, and cyano do not fall within this definition.

If a group is described as being “substituted”, a non-hydrogen radical is in the place of hydrogen radical on a carbon or nitrogen of the group. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated).

When a group is referred to as “unsubstituted” or not referred to as “substituted” or “optionally substituted”, it means that the group does not have any substituents. If a group is described as being “optionally substituted”, the group may be either (1) not substituted or (2) substituted. If a group is described as being optionally substituted with up to a particular number of non-hydrogen radicals, that group may be either (1) not substituted; or (2) substituted by up to that particular number of non-hydrogen radicals or by up to the maximum number of substitutable positions on the group, whichever is less.

If substituents are described as being “independently selected” from a group, each substituent is selected independent of the other. Each substituent, therefore, may be identical to or different from the other substituent(s).

A “payload moiety” refers to a payload radical (e.g., $-A^1$, $-A^2$) attached to the parent molecular moiety at a substitutable atom in the payload. In preferred embodiments, payloads have a chemically reactive functional group selected from the group consisting of a primary or secondary amine, hydroxyl, and sulfhydryl. Payloads $HA^1$ and $HA^2$ preferably are a drug (e.g., cytotoxic drug, antibiotic) or a reporter (e.g., a probe). Non-limiting examples of preferred payloads include a duocarmycin (duocarmycins and duocarmycin analogs and derivatives, CC-1065, CBI-based duocarmycin analogues, MCBI-based duocarmycin analogues, CCBI-based duocarmycin analogues), a doxorubicin (e.g., doxorubicin, doxorubicin conjugates, morpholino-doxorubicin, cyanomorpholino-doxorubicin), a dolastatin (e.g., dolestatin-10), combretastatin, calicheamicin, a maytansine (e.g., maytansine, maytansine analogues, DM-1, DM-4, analogs disclosed in WO2004/103272, which is incorporated herein by reference), an auristatin (e.g., auristatin E, auristatin EB (AEB), auristatin EFP (AEFP), monomethylauristatin E (MMAE)), a pyrrolobenzodiazepine (e.g. SGN-1882, SGN-1996, pyrrolobenzodiazepines disclosed in US2011/0256157 and U.S. Pat. No. 9,242,013, which are incorporated herein by reference), SN-38, 5-benzoylvaleric acid-AE ester (AEVB), tubulysins, disorazole, epothilones, Paclitaxel, docetaxel, Topotecan, rhizoxin, echinomycin, colchicine, vinblastin, vindesine, estramustine, cemadotin, eleutherobin, methotrexate, methopterin, dichloromethotrexate, 5-fluorouracil, 6-mercaptopurine, cytosine arabinoside, melphalan, leurosine, leurosideine, actinomycin, daunorubicin, daunorubicin conjugates, mitomycin C, mitomycin A, caminomycin, aminopterin, tallysomycin, podophyllotoxin, podophyllotoxin derivatives, etoposide, etoposide phosphate, vincristine, taxol, taxotere retinoic acid, butyric acid, $N^8$ acetyl spermidine and camptothecin.

In some embodiments the payload is an antibiotic agent. Suitable antibiotic agents and methods to conjugate to a cell binding agent include those described in WO2014/193722 and WO2014/194247, which are incorporated herein by reference.

Other drug conjugates provided by the invention are conjugates of synthetic glucocorticoids (e.g., dexamethasone), kinase inhibitors (e.g., dasatinib), and LXR nuclear receptor agonists, as described by Liu et al, Expert Opinion of Biological Therapy (2016) 16(5), 591-593, which is incorporated herein by reference.

As used herein, the term "reporter moiety" refers to a moiety that, under appropriate conditions directly or indirectly generates a detectable signal. Exemplary reporter moieties include, but are not limited to, fluorophores, luminescent molecules, chemiluminescent molecules, dyes, radiolabels, colorimetric molecules, and substrates for enzymes such as luciferases. In some embodiments, a reporter moiety may indirectly generate a detectable signal, for example, when the reporter moiety is a substrate for an enzyme, e.g., a luciferase. The reaction of the enzyme with the substrate then produces a detectable signal such as fluorescence or luminescence. As used herein, the term "bioluminescent reporter moiety" may refer to a moiety that is a substrate for a luciferase. For example, the bioluminescent reporter moiety can be a luciferin, a luciferin derivative, e.g., pre-luciferin, aminoluciferin, quionolyl-luciferin, napthyl luciferin, fluorolucifeirn, chloroluciferin, precursors of luciferin derivatives, a coelenterazine, or a coelenterazine derivative or analog, e.g., furimazine. The luminescent signal generated may be detected using a luminometer. As used herein, the term "fluorescent reporter moiety" may refer to a moiety that fluoresces. For example, the fluorescent reporter moiety may be a fluorophore, such as coumarin, R110, fluoroscein, DDAO, resorufin, cresyl violet, sily xanthene, or carbopyronine. Fluorescence may be detected using a fluorometer. Colorimetric payload release may be detected as an increase in absorbance at a specified wavelength.

In certain embodiments, the reporter moiety is a bioluminescent reporter moiety. In certain embodiments, the reporter moiety is a luciferin, a luciferin derivative or analog, a preluciferin or analog, coelenterazine, or a coelenterazine derivative or analog. In some embodiments, the reporter moiety is luciferin, pro-luciferin, aminoluciferin, quionolyl-luciferin, napthyl luciferin, chloroluciferin, coelenterazine, furimazine, coelenterazine-n, coelenterazine-f, coelenterazine-h, coelenterazine-hcp, coelenterazine-cp, coelenterazine-c, coelenterazine-e, coelenterazine-fcp, bisdeoxycoelenterazine ("coelenterazine-hh"), coelenterazine-i, coelenterazine-icp, coelenterazine-v, and 2-methyl coelenterazine, in addition to those disclosed in WO 2003/040100, U.S. Patent Publication No. 20080248511, U.S. Patent Publication No. US 20120117667, and U.S. Patent Publication No. US 2015/0307916, the disclosures of which are incorporated by reference herein.

In certain embodiments, the reporter moiety is a fluorescent reporter moiety. In certain embodiments, the reporter moiety is a coumarin, R110, fluoroscein, DDAO, resorufin, cresyl violet, sily xanthene, or carbopyronine. In some embodiments, the reporter moiety is rhodamine 123, rhodamine X, Alexa dyes (e.g., Alexa Fluor-350, -430, -488, -and -660), DyLight 594, sulforhodamine B, sulforhodamine 101, sulfonyl chloride derivative of sulforhodamine 101 (Texas Red), fluorescein, 6-carboxyfluorescein (6-FAM), 5-carboxyfluorescein (5-Fam), 5- or 6-carboxy-4,7,2',7'-tetrachlorofluorescein (TET), 5- or 6-carboxy-4'5'2'4'5'7' hexachlorofluorescein (HEX), 5' or 6'-carboxy-4', 5'-dichloro-2,'7'-dimethoxyfluorescein (JOE), 6-JOE, 5-carboxy-2',4',5',7'-tetrachlorofluorescein (ZOE) rhodol, fluorescein isothiocyanate, coumarin, 7-amino-4-methylcoumarin, aminocoumarin, hydroxycoumarin, silyl xanthene, or carbopyronine.

Payload moieties -$A^1$ may be attached to the parent molecule by a substitutable oxygen or sulfur. For example, representative drug payload moieties -$A^1$ include

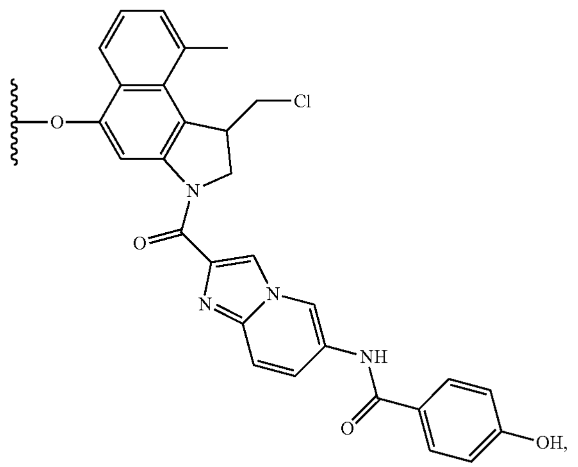

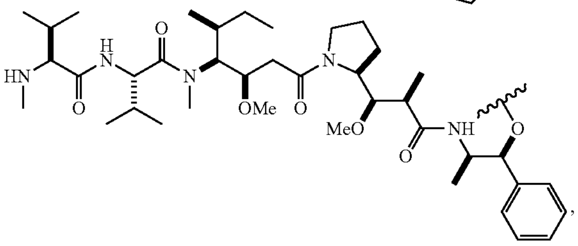

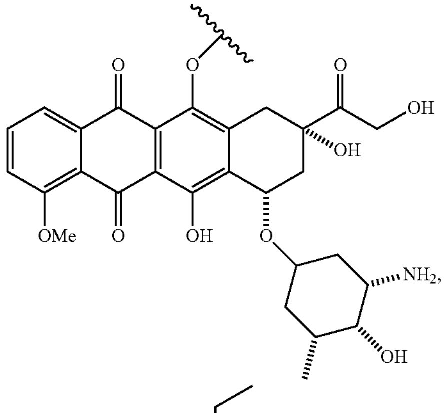

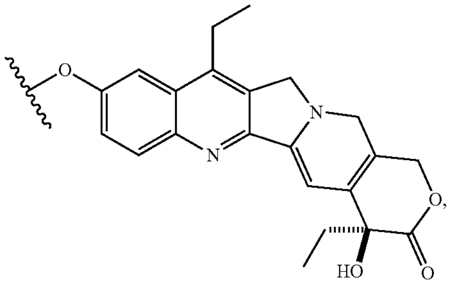

-continued
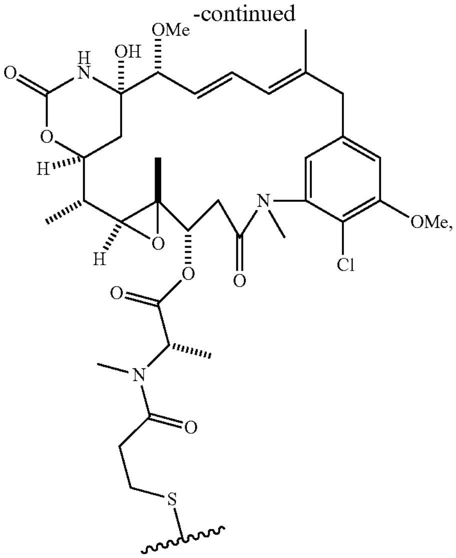
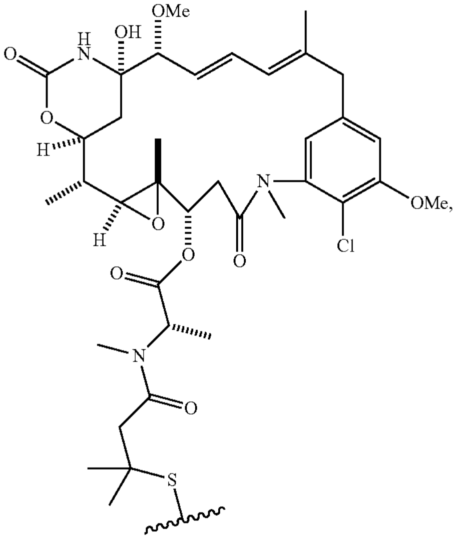
or
-continued
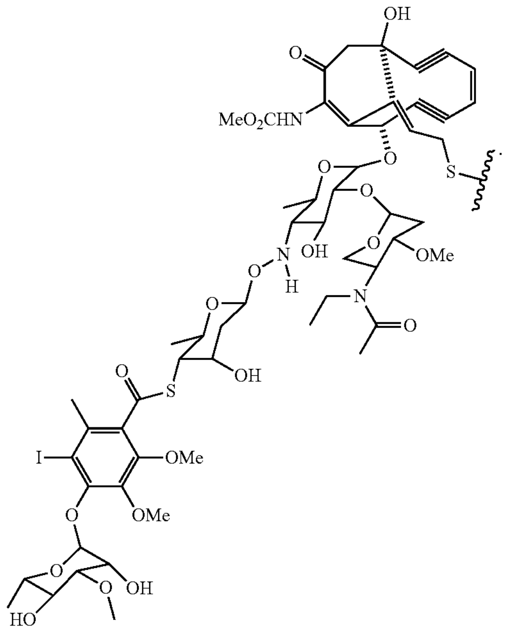
Payload moieties $-A^2$ may be attached to the parent molecule by a substitutable oxygen, nitrogen, or sulfur atom. For example, representative drug payload moieties $-A^2$ include
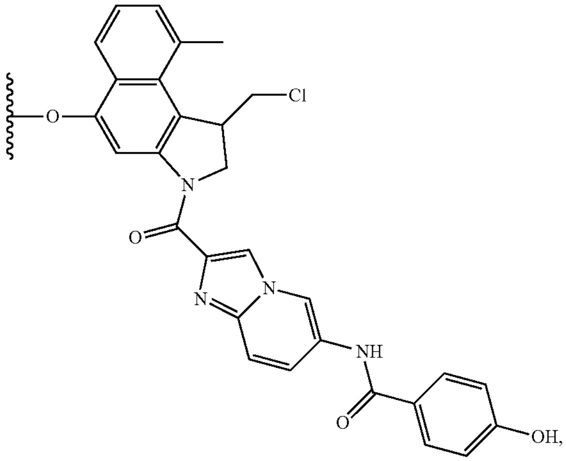

-continued
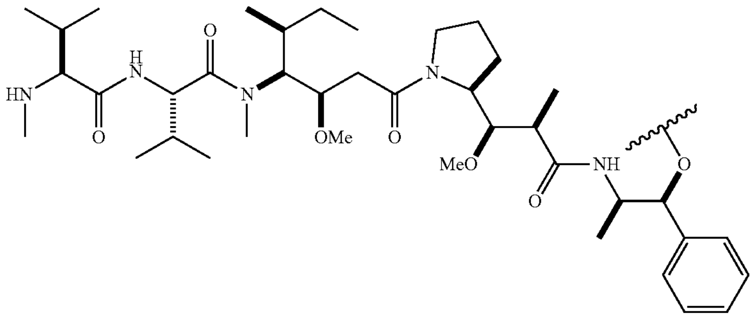
,
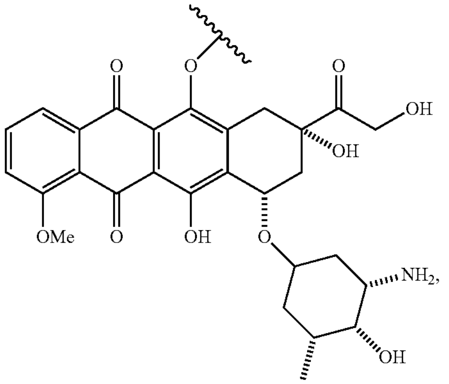
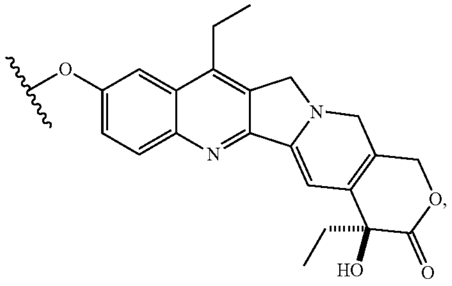
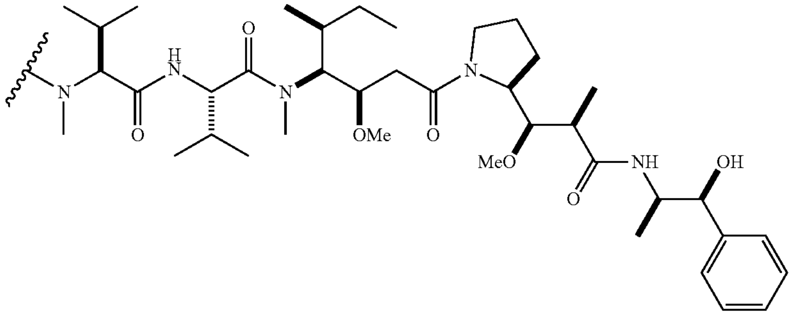
,
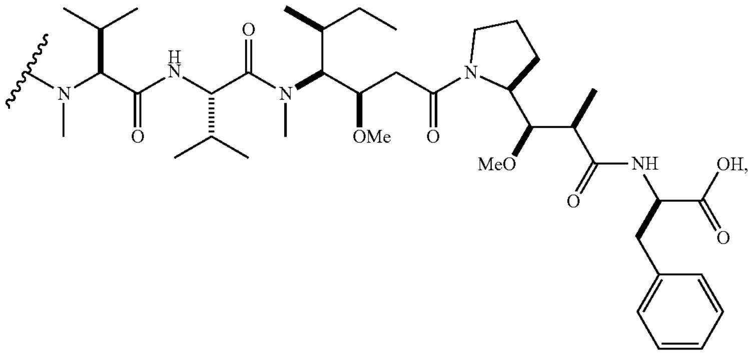
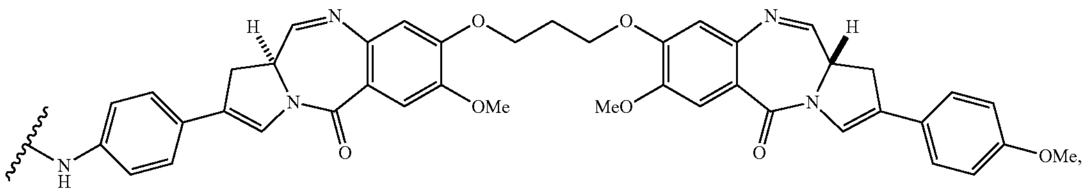

-continued

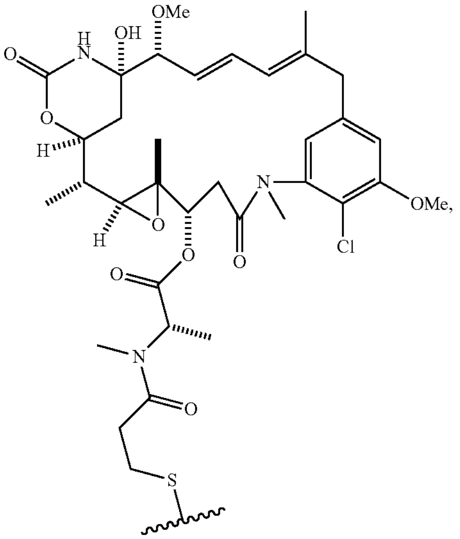

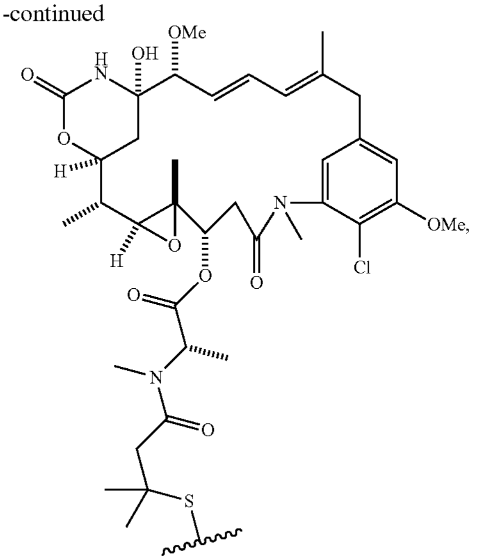

or

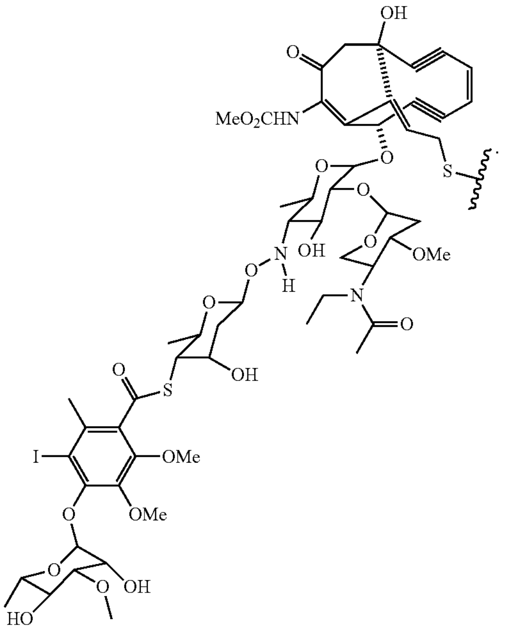

Certain compounds may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exoforms; R-, S-, and mesa-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms"). included in the term "isomer" are compounds with one or more isotopic substitutions. For example, H may be in any isotopic form, including $^{1}H$, $^{2}H$ (D), and $^{3}H$ (T); C may be in any isotopic form, including $^{12}C$, $^{13}C$, and $^{14}C$; O may be in any isotopic form, including $^{16}O$ and $^{18}O$; and the like.

A cell binding agent may be of any kind and include peptides and non-peptides. These can include antibodies or a fragment(s) of an antibody that contains at least one binding site, lymphokines, hormones, growth factors, nutrient-transport molecules, or any other cell binding molecule or substance (e.g., a protein, a carbohydrate, nucleic acid, etc.). The cell binding agent may be a nucleotide or polynucleotide including nucleic acids such as DNA and RNA, and those that include dU allylamine nucleotides. The cell binding agent may be, or comprise, a polypeptide. The polypeptide may be a cyclic polypeptide. Other proteins/peptide include ApoB, insulin, transferrin, and siderophores (e.g., for use with antibiotics). Siderophores are described, for example, by de Carvalho et al., Frontiers in Microbiology (June 2014), 5 (290), doi 10.3389/fmicb.2014.00290, Starr et al., J. Med. Chem. (2014) 57, 3845-3855, and Miller et al., Biol. Met. (1991) 4(1), 62-9, which are incorporated herein by reference. The cell binding agent may be a small molecule drug as described in Casi et al., J. Med. Chem. (2015) 58 (22), 8751-8761 and Srinivasarao et al., Nat. Rev.

Drug Discovery (2015), 14, 203-219, which are incorporated herein by reference. For example, the small molecule drug may be folate.

The term "antibody" as referred to herein includes whole antibodies and any antigen binding fragment (i.e. "antigen-binding portion") or a single chain(s) thereof. An "antibody" refers to a glycoprotein comprising at least two heavy (H) chains and two light (L) chains inter-connected by disulfide bonds or an antigen binding portion thereof. Each heavy chain is comprised of a heavy chain variable region ($V_H$) and a heavy chain constant region. The heavy chain constant region is comprised of three domains, $CH_1$, $CH_2$, and $CH_3$, and may be of the mu, delta, gamma, alpha, or epsilon isotype. Each light chain is comprised of a light chain variable region ($V_L$) and a light chain constant region. The light chain constant region is comprised of one domain, C°, which may be of the kappa or lambda isotype. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

"Antibody fragments" comprise a portion of a full length antibody, generally the antigen binding or variable region thereof. Examples of antibody fragments include Fab, Fab', $F(ab')_2$ and Fv fragments; diabodies; linear antibodies; fragments produced by a Fab expression library, anti-idiotypic (anti-Id) antibodies, CDR (complementary determining region), and epitope-binding fragments of any of the above that immunospecifically bind to cancer cell antigens, viral antigens or microbial antigens, single-chain antibody molecules; and multispecific antibodies formed from antibody fragments.

The terms "cell binding moiety" and "antibody moiety" refer to a cell binding radical or antibody radical onto which a group (e.g., G) is substituted. For example, a group G in $Ab-(G)_p$ is in place of a hydrogen radical on the antibody. Thus, an antibody moiety (or cell binding moiety) includes amino acid side chain heteroatoms (e.g., —NH— from a lysine; —S— from a cysteine) that are bonded to G. In the case of engineered antibodies bearing unnatural amino acid side chains (e.g., that contain an alkyne or azido), the antibody moiety includes those atoms of the conjugate that are derived from the unnatural amino acid side chain. For example, in the case of an alkyne-containing side chain conjugated to an azido by Click chemistry, the resulting alkene-diyl fragment is considered part of the antibody moiety (e.g.,

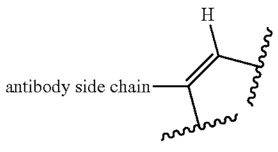

).

The antibody may be a multispecific antibody, a human antibody, a humanized antibody (fully or partially humanized), an animal antibody such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), a recombinant antibody, a chimeric antibody, a single-chain Fv ("scFv"), a single chain antibody, a single domain antibody, a Fab fragment, a F(ab') fragment, a F(ab')2 fragment, a disulfide-linked Fv ("sdFv"), and an anti-idiotypic ("anti-Id") antibody, a dual-domain antibody, a dual variable domain (DVD) or a triple variable domain (TVD) antibody (dual-variable domain immunoglobulin, and functionally active epitope-binding fragment of any of the above. In particular, an antibody includes an immunoglobulin molecule and an immunologically active fragment of an immunoglobulin molecule, namely, a molecule that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass.

A wide variety of tumor-specific or other disease-specific antigens have been identified and antibodies to those antigens have been used or proposed for use in the treatment of such tumors or other diseases. The antibodies that are known in the art can be used in the conjugates of the invention, in particular, for the treatment of the disease with which the target antigen is associated. Non-limiting examples of target antigens (and their associated diseases) to which an antibody-linker-drug conjugate of the invention can be targeted include: Her2 (breast cancer), CD20 (lymphomas), EGFR (solid tumors), CD22 (lymphomas, including nonHodgkin's lymphoma), CD52 (chronic lymphocytic leukemia), CD33 (acute myelogenous leukemia), CD4 (lymphomas, autoimmune diseases, including rheumatoid arthritis), CD30 (lymphomas, including non-Hodgkin's lymphoma), Muc18 (melanoma), integrins (solid tumors), PSMA (prostate cancer, benign prostatic hyperplasia), CEA (colorectal cancer), CD11a (psoriasis), CD80 (psoriasis), CD23 (asthma), CD40L (immune thromobcytopenic purpura), CTLA4 (T cell lymphomas) and BLys (autoimmune diseases, including systemic lupus erythematosus).

Example antibodies are also found in Table 1.

TABLE 1

| Antigens | Antibodies |
|---|---|
| CD30 | Ch IgG1 |
| CD22 | Hz IgG4 |
| CD33 | Hz IgG4 |
| CD19 | Hz IgG1 |
| CD138 | Ch IgG4 |
| CD22 | Hz IgG1 |
| CD79b | Hz IgG1 |
| CD74 | Hz IgG1 |
| HER2 | Hz IgG1 |
| GPNMB | Hu IgG2 |
| PSMA | Hu IgG1 |
| CD56 | Hz IgG1 |
| SLC44A4 | Hu IgG2 |
| CA6 | Hu IgG1 |
| CA-IX | Hu IgG1 |
| Mesothelin | Hu IgG1 |

TABLE 1-continued

| Antigens | Antibodies |
|---|---|
| CD70 | Hu IgG1 |
| CD66e/ CEACAM5 | Hz IgG1 |
| Nectin-4 | Hu IgG1 |

Ch: chimeric;
Hz: humanized;
Hu: fully human;
GPNMB: Glycoprotein NMB;
PSMA: prostate specific membrane antigen.

The antibody may be a therapeutic antibody such as Trastuzumab (Herceptin), Abciximab (ReoPro), Adalimumab (Humira), Alemtuzumab (Campath), Basiliximab (Simulect), Belimumab (Benlysta), Bevacizumab (Avastin), Brentuximab vedotin (Adcetris), Canakinumab (Ilaris), Cetuximab (Erbitux), Certolizumab pegol (Cimzia), Daclizumab (Zenapax), Denosumab (Prolia, Xgeva), Eculizumab (Soliris), Efalizumab (Raptiva), Gemtuzumab (Mylotarg), Golimumab (Simponi), Ibritumomab tiuxetan (Zevalin), Infliximab (Remicade), Ipilimumab (MDX-101; Yervoy), Muromonab-CD3 (Orthoclone OKT3), Natalizumab (Tysabri), Ofatumumab (Arzerra), Omalizumab (Xolair), Palivizumab (Synagis), Panitumumab (Vectibix), Ranibizumab (Lucentis), Rituximab (Rituxan, Mabthera), Tocilizumab (or Atlizumab) (Actemra and RoActemra), and Tositumomab (Bexxar).

2. Conjugates

Disclosed herein are quinone-containing conjugates of formula (I). The intracellular space is a reducing environment that may reduce the quinone moiety. Upon uptake of conjugates of the invention by cells, the quinone may be reduced by intracellular reduction potential to tracelessly release the payload (e.g., antimitotic agent), i.e., meaning no residual linker atoms are left on the payload moiety. As described in US2015/0307916, a quinone-linked cargo molecule (e.g. luciferin, a fluorophore or furimazine) was efficiently released upon entry into cells. Quinone moieties also appear to be stable in a non-reducing environment suggesting they would be stable outside of target cells, for example, in the blood stream. Since quinone reduction followed by traceless elimination of a covalent adduct appears to occur rapidly and efficiently in all the cell types tested so far, and quinone moieties are expected to be stable in the blood stream, quinone-containing conjugates may provide a universal means for efficiently and selectively releasing payloads inside of target cells.

Payloads $HA^1$ attached by a substitutable oxygen or sulfur atom may be released as shown in Scheme 1 upon intracellular reduction of the quinone moiety.

Scheme 1

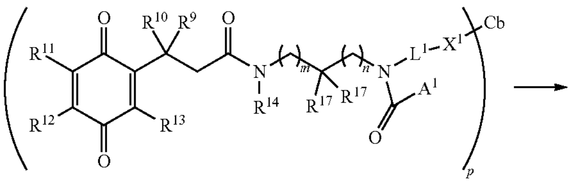

-continued

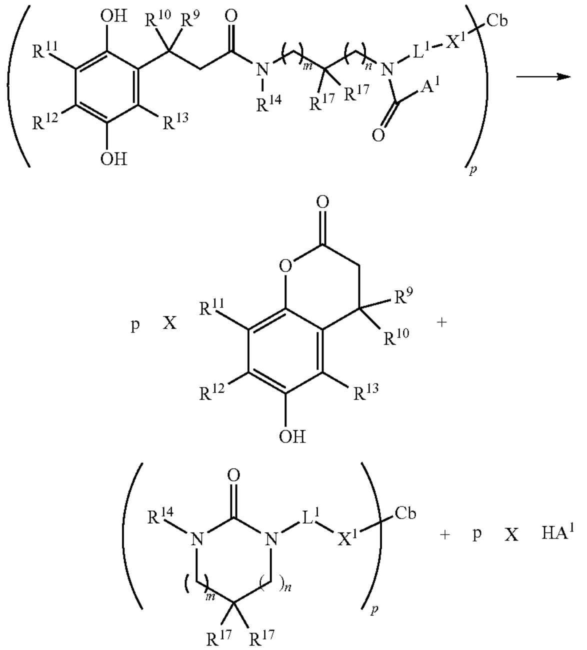

Alternatively, payloads $HA^1$ attached by an oxygen or sulfur atom may be released as shown in Scheme 2a upon intracellular reduction of the quinone moiety. Payloads $HA^2$ attached by an oxygen, sulfur, or substitutable nitrogen atom via self-immolative substitutable benzyl linker may be released upon intracellular quinone reduction as shown in Scheme 2b.

Scheme 2a

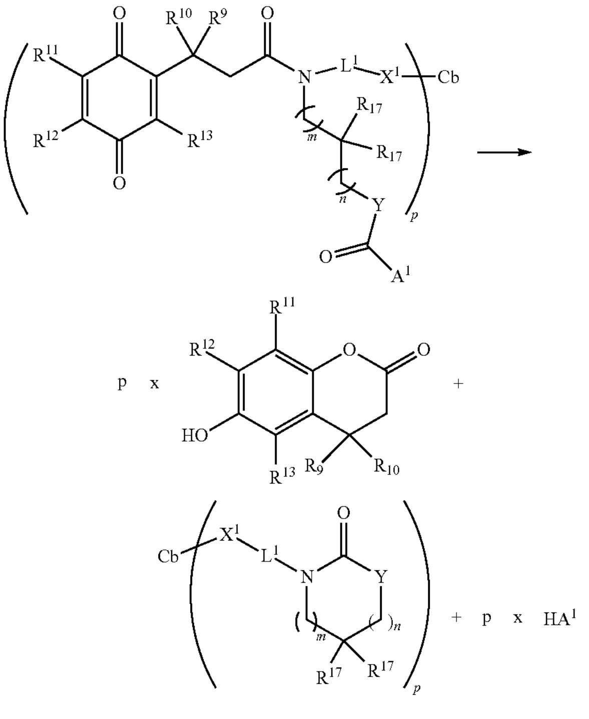

Scheme 2b

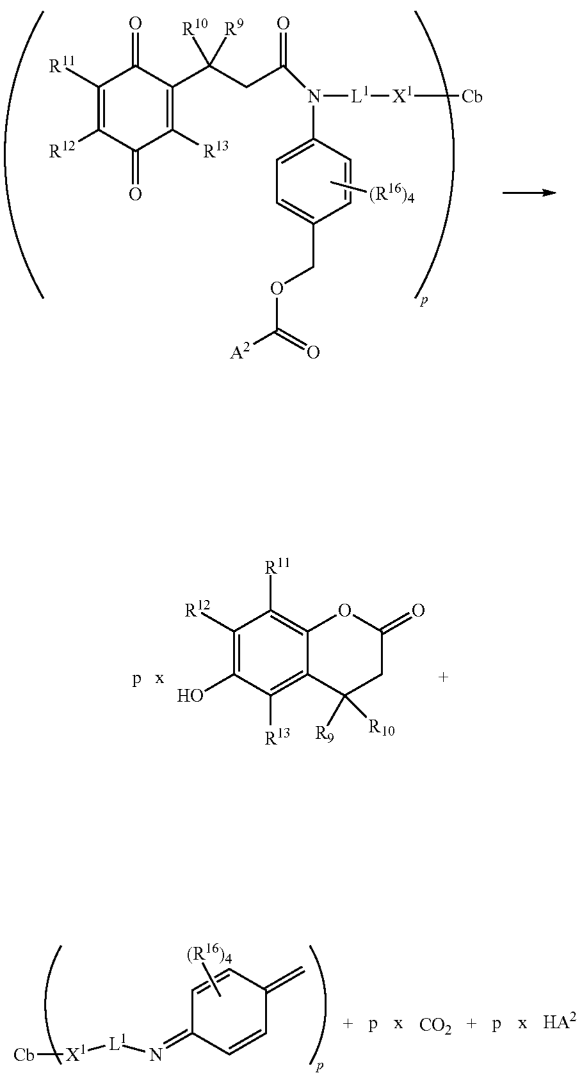

In another variation, an antibody may be attached to one side of the quinone through a second $L^2$ linker while payloads may be attached to the other side of the quinone as shown in Schemes 3a-3c. Payloads $HA^2$ directly attached by an oxygen, sulfur, or substitutable nitrogen atom may be released as shown in Scheme 3a upon intracellular reduction of the quinone moiety. Similarly, payloads $HA^1$ attached by an oxygen or sulfur atom via self-immolative amine-linker may be released upon intracellular quinone reduction as shown in Scheme 3b. Payloads $HA^2$ attached by an oxygen, sulfur, or substitutable nitrogen atom via self-immolative unsubstituted or substituted benzyl linker may be released upon intracellular quinone reduction as shown in Scheme 3c.

Scheme 3a

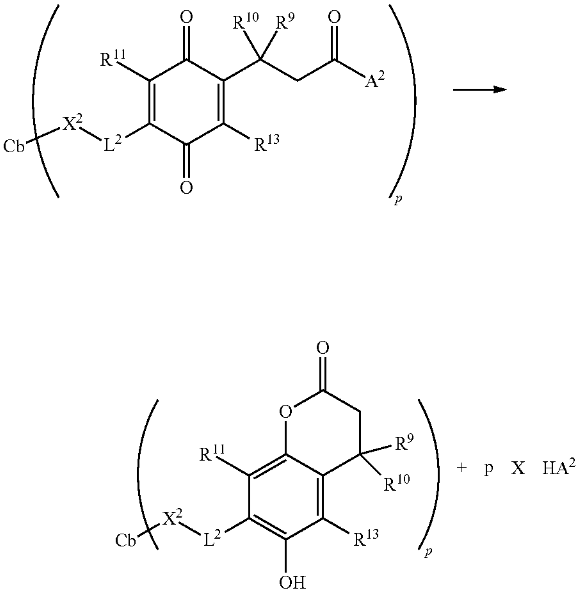

Scheme 3b

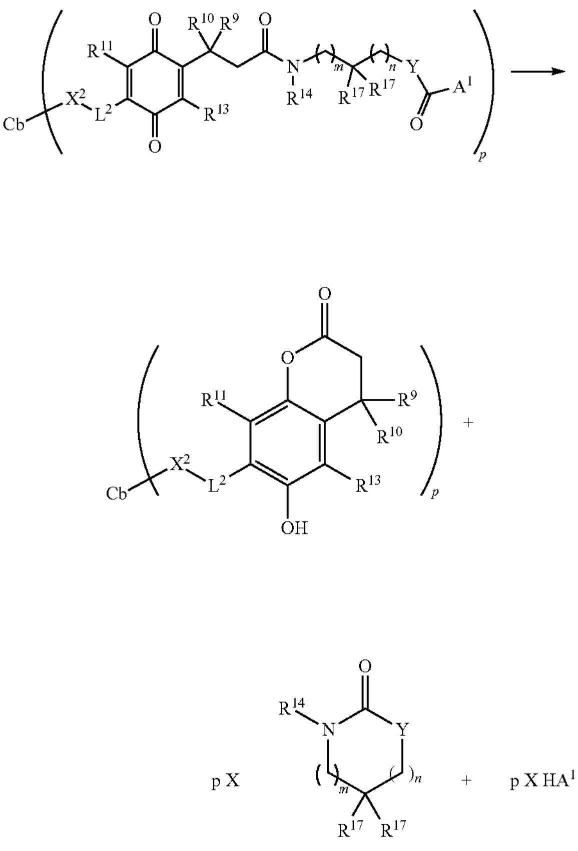

Scheme 3c

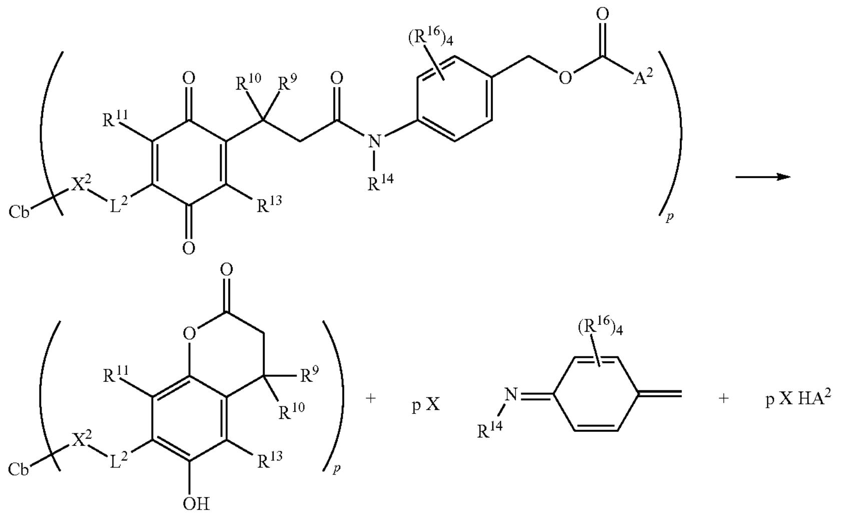

According to one aspect of the invention are conjugates of formula (I).

In some embodiments, formula (I) is Ab-$(G)_p$, wherein Ab is an antibody moiety, and G and p are as defined herein.

In some embodiments, the cell binding moiety is a small molecule drug moiety, where the parent small molecule drug has affinity for a target receptor on a cell. Representative examples of small molecule drugs and target receptors include folate (folate receptor), somatostatin analogs (somatostatin receptor), and aromatic sulfonamides (carbonic anhydrase IX), as described in Casi et al., J. Med. Chem. (2015) 58 (22), 8751-8761 and Srinivasarao et al., Nat. Rev. Drug Discovery (2015), 14, 203-219. Preferably, p is 1, when Cb is a small molecule drug moiety. In preferred embodiments, the small molecule drug moiety is folate.

In some embodiments of formula (I), G is formula (II), (III), or (IV) and $A^1$ and/or $A^2$ is an anticancer drug. In further embodiments, formula (I) is Ab-$(G)_p$, wherein Ab is an antibody moiety, p is as defined herein, G is formula (II), (III), or (IV), and $A^1$ and/or $A^2$ is an anticancer drug.

In some embodiments, G is formula (II), (III), or (IV) and $A^1$ and/or $A^2$ is a reporter moiety. In preferred embodiments, G is formula (III) or (IV) and $A^1$ and/or $A^2$ is a reporter moiety. In further embodiments, formula (I) is Ab-$(G)_p$, wherein Ab is an antibody moiety, p is as defined herein, G is formula (II), (III), or (IV), and $A^1$ and/or $A^2$ is a reporter moiety, as defined herein. In preferred embodiments, formula (I) is Ab-$(G)_p$, wherein Ab is an antibody moiety, p is as defined herein, G is formula (III) or (IV), and $A^1$ and/or $A^2$ is a reporter moiety. In other embodiments, Cb is a small molecule drug moiety, p is 1, and $A^1$ and/or $A^2$ is a reporter moiety, as defined herein. In further embodiments, the small molecule drug moiety is folate.

In some embodiments, $X^1$ or $X^2$ is

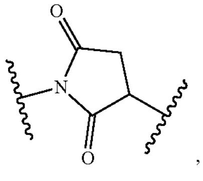
,
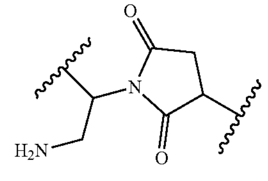
, $-C(O)CH_2-$, $-NHC(S)-$, $-NHC(O)-$, $-C(O)-$, $-CH(SO_3H)-C(O)-$,

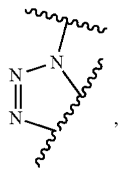
,
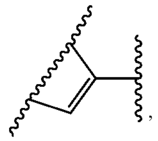
,

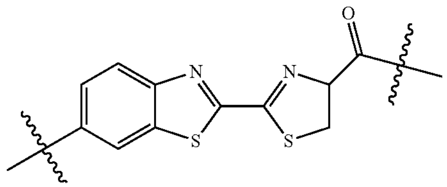 [SMILES: *C(=O)C1CSC(c2nc3ccc(*)cc3s2)=N1]
, $-NH-$, or $-N(C_{1-6}alkyl)-$.

In some embodiments, $X^1$ or $X^2$ is

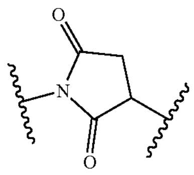
,
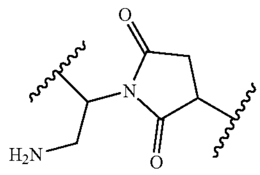
, or $-C(O)CH_2$-bonded to Cb through a sulfhydryl group (e.g., cysteine) in Cb; or $X^1$ or $X^2$ is $-NHC(S)-$, $-NHC(O)-$, $-C(O)-$, or $-CH(SO_3H)-C(O)-$ bonded to Cb through an amino (e.g., lysine) in Cb; or $X^1$ or $X^2$ is

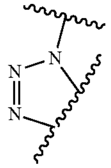
or
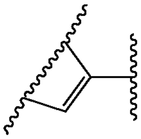
;

or $X^1$ or $X^2$ is

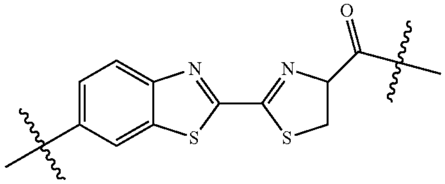

bonded to Cb through N-terminal cysteine of Cb; or $X^1$ or $X^2$ is —NH—, or —N($C_{1-6}$alkyl)- bonded to Cb through a carbonyl of Cb.

In further embodiments, $X^1$ or $X^2$ is —NH—, or —N($C_{1-6}$alkyl)- bonded to folate through a carbonyl derived from a carboxyl of folate (i.e.

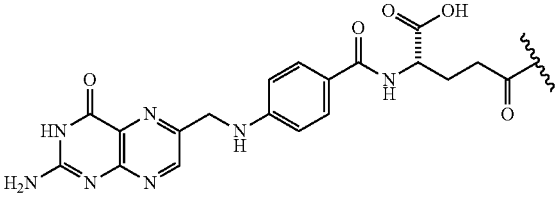
).

In some embodiments, a first or second linker moiety contains or consists of at least one of —$C_{1-12}$alkylene-, —($C_{2-6}$alkylene-O)$_x$—$C_{1-6}$alkylene-, or $C_{3-8}$cycloalkylene bonded to the parent molecular moiety, and optionally one or more additional divalent moieties covalently linked to the antibody linking moiety ($X^1$ or $X^2$), the one or more additional divalent moieties being selected from the group consisting of —$C_{1-6}$alkylene-, —$C_{2-6}$alkylene-O—, $C_{3-8}$cycloalkylene, —C(O)—, —O—, —S—, —S(O)—, —S(O)$_2$—, —NR$^{20}$—, —C(R$^{21}$)═N—NH—, —CH(CO$_2$H)—,

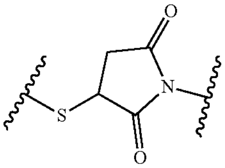
, an amino acid moiety, a protected amino acid moiety, and phenylene; wherein the $C_{3-8}$cycloalkylene and phenylene are optionally independently substituted with 1-4 substituents independently selected from the group consisting of $C_{1-4}$alkyl, $C_{1-4}$haloalkyl, $C_1$ 4alkoxy, halo, cyano, or hydroxy; wherein x, $R^{20}$ and $R^{21}$ are as defined herein.

In some embodiments, $L^1$ is $L^{1a}$ or $L^{1a}$-$L^{1b}$, wherein $L^{1b}$ is bonded to $X^1$; $L^{1a}$ is —$C_{1-12}$alkylene-, —($C_{2-6}$alkylene-O)$_x$—$C_{1-6}$alkylene-, or $C_{3-8}$cycloalkylene; $L^{1b}$ comprises, or consists of, one or more covalently bonded divalent members, the one or more divalent members being selected from the group consisting of —$C_{1-6}$alkylene-, —$C_{2-6}$alkylene-O—, $C_{3-8}$cycloalkylene, —C(O)—, —O—, —S—, —S(O)—, —S(O)$_2$—, —NR$^{20}$—, —C(R$^{21}$)═N—NH—, —CH(CO$_2$H)—,

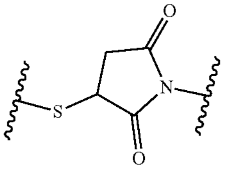
, an amino acid moiety, a protected amino acid moiety, and phenylene; wherein the $C_{3-8}$cycloalkylene and phenylene of $L^{1a}$ and/or $L^{1b}$ is optionally independently substituted with 1-4 substituents independently selected from the group consisting of $C_{1-4}$alkyl, $C_{1-4}$haloalkyl, $C_{1-4}$alkoxy, halo, cyano, or hydroxy; $R^{20}$ and $R^{21}$ at each occurrence are independently hydrogen or $C_{1-4}$alkyl; and x is an integer from 1 to 20. In further embodiments included in the foregoing, $L^{1b}$ is —C(O)NR$^{20}$-$L^{1c}$-, —NR$^{20}$C(O)-$L^{1c}$-, —NR$^{20}$C(O)O-$L^{1c}$-, —C(O)-$L^{1c}$-, —S-$L^{1c}$-, —S(O)-$L^{1c}$-, —S(O)$_2$-$L^{1c}$-, or —NR$^{20}$-$L^{1c}$-; and $L^{1c}$ is —$C_{1-6}$alkylene-, —$C_{1-6}$alkylene-NR$^{20}$C(O)—$C_{1-6}$alkylene-S—S—$C_{1-6}$alkylene-, —$C_{1-6}$alkylene-NR$^{20}$C(O)NH—N═C(R$^{21}$)-phenylene-O—$C_{1-6}$alkylene-, $C_{3-8}$cycloalkylene, —($C_{2-6}$alkylene-O)—$C_{1-6}$alkylene-, —$C_{1-6}$alkylene-$C_{3-8}$cycloalkylene-, —$C_{3-8}$cycloalkylene-$C_{1-6}$alkylene-, —$C_{1-6}$alkylene-$C_{3-8}$cycloalkylene-$C_{1-6}$alkylene-, —$C_{1-6}$alkylene-S—S—$C_{1-6}$alkylene-, or

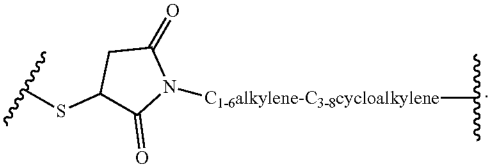
.

In further embodiments included in the foregoing, $L^{1b}$ is —C(O)NR$^{20}$-$L^{1c}$-, -cit-val-C(O)$C_{1-6}$alkylene-, —NR$^{20}$C(O)—, —NR$^{20}$C(O)-$L^{1c}$-, —NR$^{20}$C(O)O-$L^{1c}$-, -ala-val-C(O)$C_{1-6}$alkylene-, -cit-val-C(O)O—$C_{2-6}$alkylene-O—$C_{1-6}$alkylene-, -ala-val-C(O)O—$C_{2-6}$alkylene-O—$C_{1-6}$alkylene-, —S—S—$C_{1-6}$alkylene-, —NH—N═C(R$^{21}$)-phenylene-O—$C_{1-6}$alkylene-,

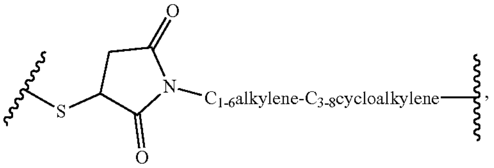
,

—$C_{1-6}$alkylene-, —$C_{2-6}$alkylene-O—, or $C_{3-8}$cycloalkylene, and $L^{1c}$ is —$C_{1-6}$alkylene-, —$C_{1-6}$alkylene-NR$^{20}$C(O)—$C_{1-6}$alkylene-S—S—$C_{1-6}$alkylene-, —$C_{1-6}$alkylene-NR$^{20}$C(O)NH—N═C(R$^{21}$)-phenylene-O—$C_{1-6}$alkylene-, $C_{3-8}$cycloalkylene, —($C_{2-6}$alkylene-O)—$C_{1-6}$alkylene-, —$C_{1-6}$alkylene-$C_{3-8}$cycloalkylene-, —$C_{3-8}$cycloalkylene-$C_{1-6}$alkylene-, —$C_{1-6}$alkylene-$C_{3-8}$cycloalkylene-$C_{1-6}$alkylene-, —$C_{1-6}$alkylene-S—S—$C_{1-6}$alkylene-, or

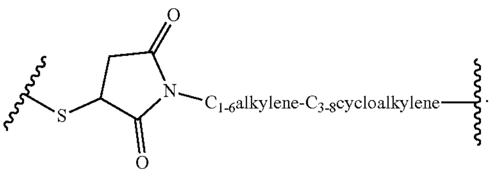

In further embodiments included in the foregoing, $L^{1a}$-$L^{1b}$ is —$C_{1-12}$alkylene-C(O)$NR^{20}$-$L^{1c}$-, —($C_{2-6}$alkylene-O)$_x$—$C_{1-6}$alkylene-C(O)$NR^{20}$-$L^{1c}$-, —$C_{3-8}$cycloalkylene-C(O)$NR^{20}$-$L^{1c}$-, —$C_{1-12}$alkylene-$NR^{20}$C(O)-$L^{1c}$-, —($C_{2-6}$alkylene-O)$_x$—$C_{1-6}$alkylene-$NR^{20}$C(O)-$L^{1c}$-, —$C_{3-8}$cycloalkylene-$NR^{20}$C(O)-$L^{1c}$-, —($C_{2-6}$alkylene-O)$_x$—$C_{1-6}$alkylene-cit-val-C(O)$C_{1-6}$alkylene-, —($C_{2-6}$alkylene-O)$_x$—$C_{1-6}$alkylene-ala-val-C(O)$C_{1-6}$alkylene-, —$C_{1-12}$alkylene-$C_{3-8}$cycloalkylene-, —$C_{3-8}$cycloalkylene-$C_{1-12}$alkylene-, —$C_{1-6}$alkylene-$C_{3-8}$cycloalkylene-$C_{1-6}$alkylene-, —($C_{2-6}$alkylene-O)$_x$—$C_{1-6}$alkylene-$C_{3-8}$cycloalkylene-, or —($C_{2-6}$alkylene-O)$_x$—$C_{1-6}$alkylene-$C_{3-8}$cycloalkylene-$C_{1-6}$alkylene-.

In further embodiments included in the foregoing —($C_{2-6}$alkylene-O)$_x$—$C_{1-6}$alkylene—in $L^{1a}$ is —($CH_2CH_2O$)$_x$—$C_{1-6}$alkylene-.

In further embodiments included in the foregoing, $L^a$ is —($CH_2CH_2O$)$_{1-2}$—$CH_2CH_2$—; $L^{1b}$ is —C(O)$NR^{20}$-$L^{1c}$-, -ala-val-C(O)($CH_2$)$_5$—, -cit-val-C(O)($CH_2$)$_5$—, or

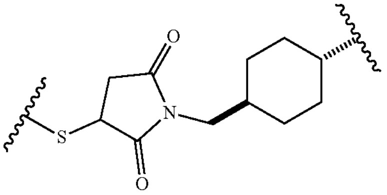
;

and $L^{1c}$ is —$CH_2CH_2$—, —$CH_2CH_2$—$NR^{20}$C(O)—$CH_2CH_2$—S—S—CH($CH_3$)$CH_2CH_2$—, or —$CH_2CH_2$—$NR^{20}$C(O)NH—N=C($CH_3$)-1,4-phenylene-O—$CH_2CH_2CH_2$—, or

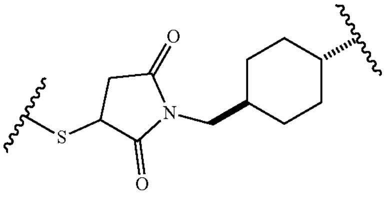
.

In further embodiments included in the foregoing, $L^{1b}$-$X^1$ is

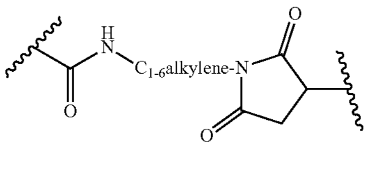
,

-continued

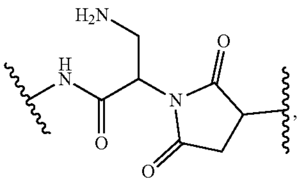
,

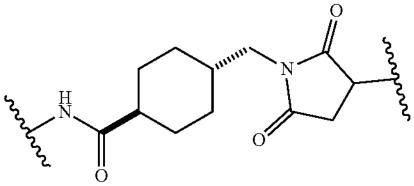
,

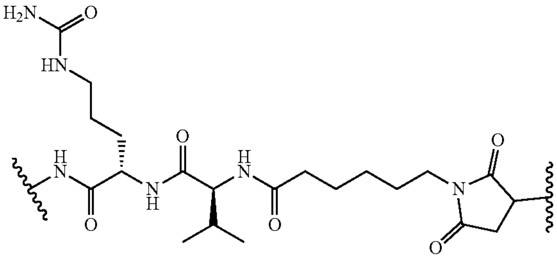
,

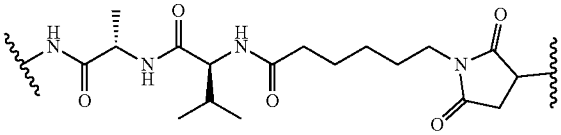
,

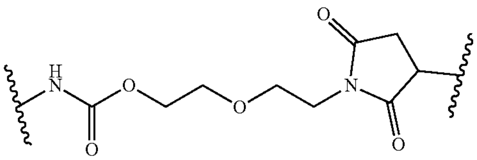
,

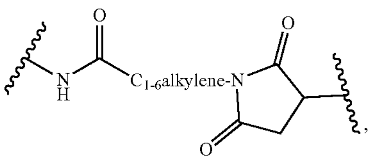
,

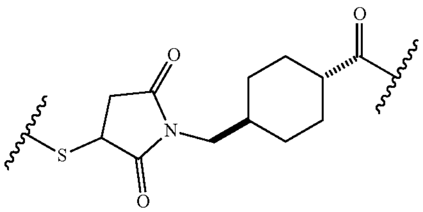
,

—C(O)$NR^{20}$—$C_{1-6}$alkylene-$NR^{20}$C(O)—$C_{1-6}$alkylene-S—S—$C_{1-6}$alkylene-C(O)—, —C(O)$NR^{20}$—$C_{1-6}$alkylene-$NR^{20}$C(O)—$C_{1-6}$alkylene-S—S—$C_{1-6}$alkylene-CH($SO_3H$)—C(O)—, —C(O)$NR^{20}$—$C_{1-6}$alkylene-$NR^{20}$C(O)NH—N=C($R^{21}$)-phenylene-O—$C_{1-6}$alkylene-C(O)—, or

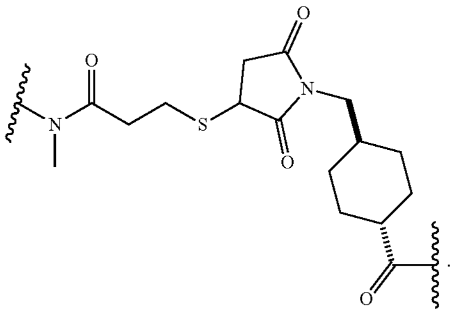
In further embodiments included in the foregoing, $L^1$-$X^1$ is
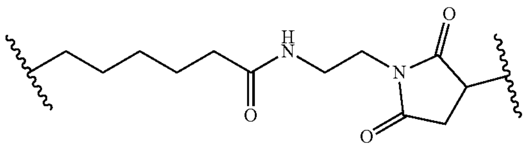,
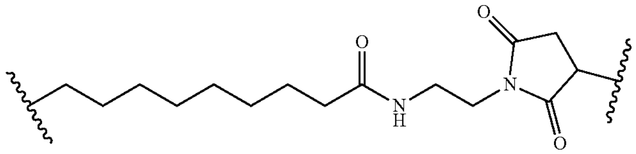,
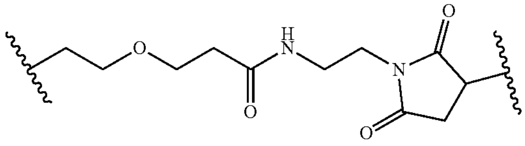,
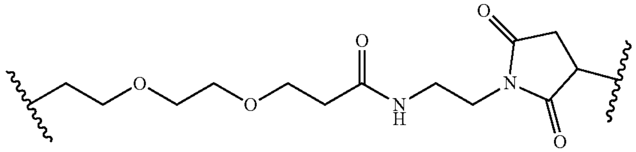,
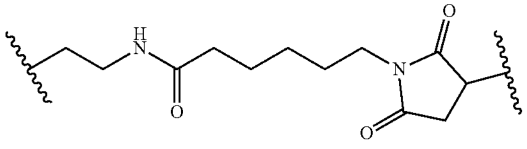, 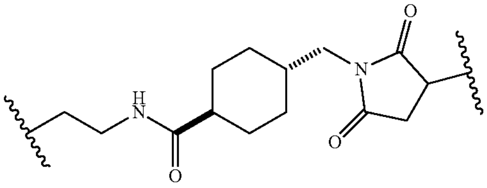,
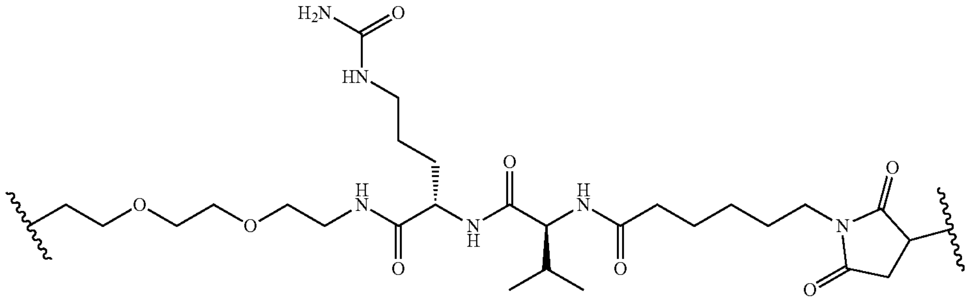,
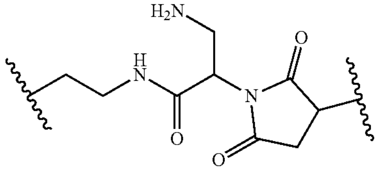, 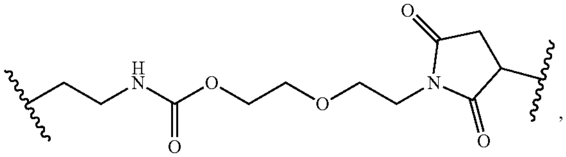, -continued
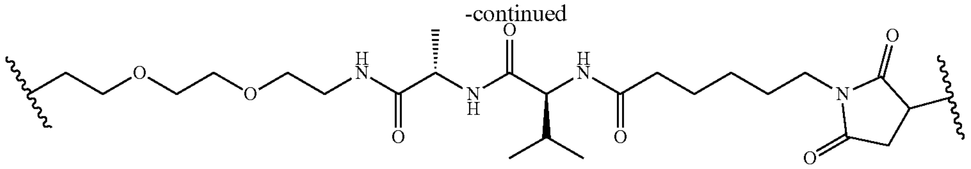,
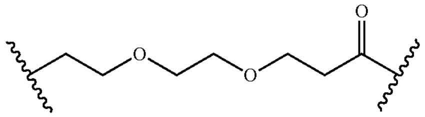,
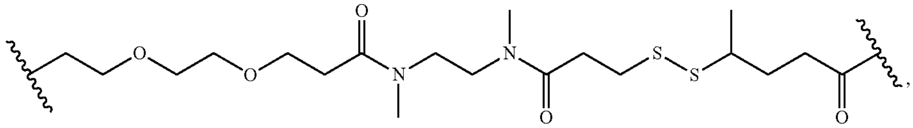,
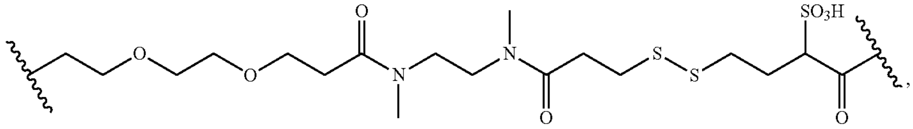,
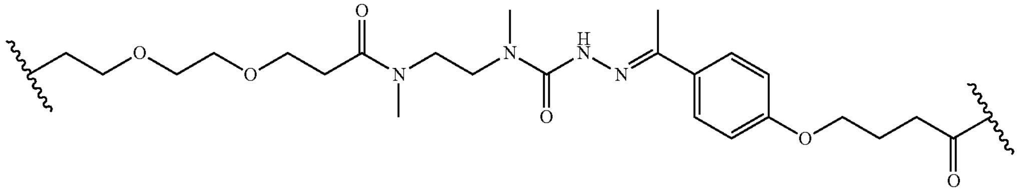, or
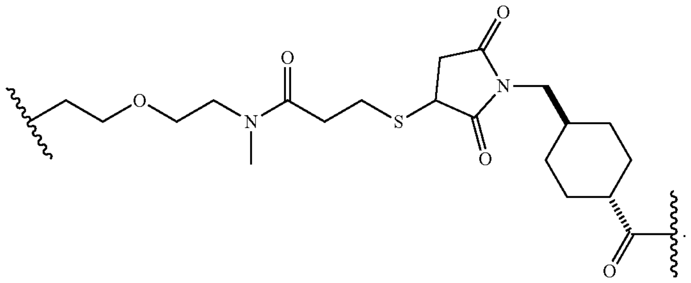
In other embodiments included in the foregoing are the following further representative $L^1$-$X^1$:
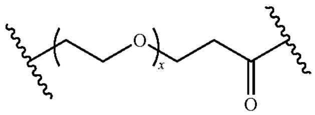,
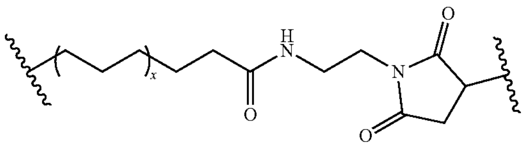,
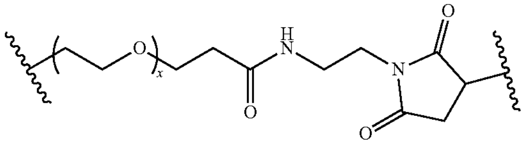,
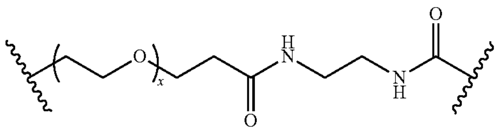,
-continued
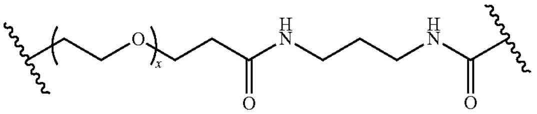,
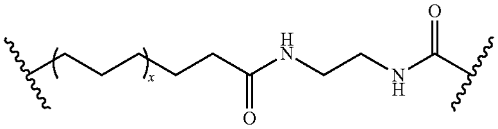,
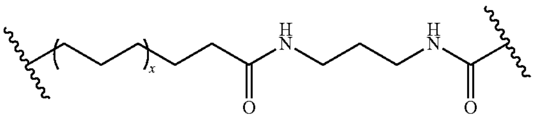,
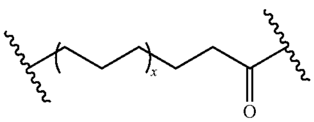, -continued

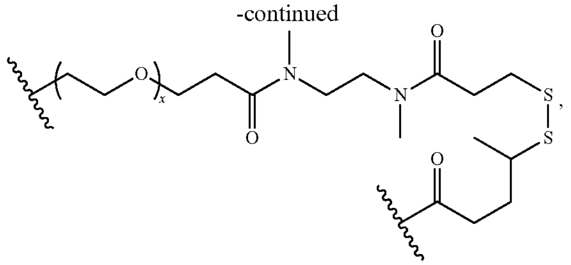

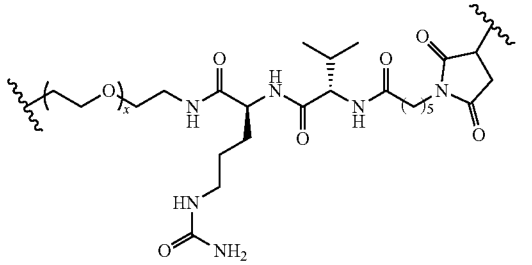

and

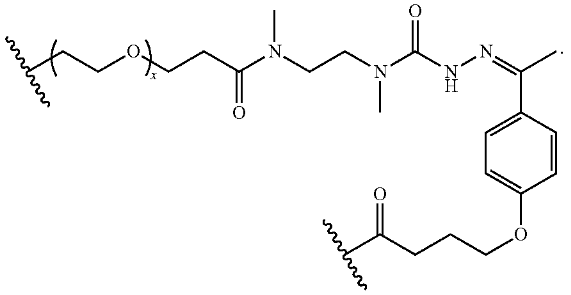

In certain embodiments, x is 2, 3, or 4.

In some embodiments, $L^2$ is $L^{2a}$ or $L^{2a}$-$L^{2b}$, wherein $L^{2b}$ is bonded to $X^2$; $L^{2a}$ is —$C_{2-6}$alkylene-; $L^{2b}$ comprises, or consists of, one or more covalently bonded divalent members, the one or more divalent members being selected from the group consisting of —$C_{1-6}$alkylene-, —$C_{2-6}$alkylene-O—, $C_{3-8}$cycloalkylene, —C(O)—, —O—, —S—, —S(O)—, —$S(O)_2$—, —$NR^{30}$—, —$C(R^{31})$=N—N—, —$CH(CO_2H)$—,

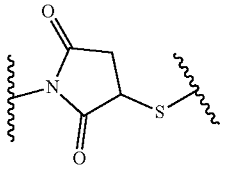
, an amino acid moiety, and phenylene; wherein the $C_{3-8}$cycloalkylene and phenylene of $L^{1b}$ are optionally independently substituted with 1-4 substituents independently selected from the group consisting of $C_{1-4}$alkyl, $C_{1-4}$haloalkyl, $C_1$ 4alkoxy, halo, cyano, or hydroxy; and $R^{30}$ and $R^{31}$ at each occurrence are independently hydrogen or $C_{1-4}$alkyl.

In further embodiments included in the foregoing, $L^{2b}$ is —C(O)$NR^{30}$-$L^{2c}$-, —$NR^{30}$C(O)-$L^{2c}$-, —$NR^{30}$C(O)O-$L^{2c}$-, —C(O)-$L^{2c}$-, —O-$L^{2c}$-, —S-$L^{2c}$-, —S(O)-$L^{2c}$-, —$S(O)_2$-$L^{2c}$-, or —$NR^{30}$-$L^{2c}$-; and $L^{2c}$ is —$C_{1-6}$alkylene-, —$C_{1-6}$alkylene-$NR^{30}$C(O)—$C_{1-6}$alkylene-S—S—$C_{1-6}$alkylene-, —$C_{1-6}$alkylene-$NR^{30}$C(O)NH—N=$C(R^{31})$-phenylene-O—$C_{1-6}$alkylene-, —$C_{3-8}$cycloalkylene, —($C_{2-6}$alkylene-O)—$C_{1-6}$alkylene-, —$C_{1-6}$alkylene-$C_{3-8}$cycloalkylene-, —$C_{3-8}$cycloalkylene-$C_{1-6}$alkylene-, —$C_{1-6}$alkylene-$C_{3-8}$cycloalkylene-$C_{1-6}$alkylene-, —$C_{1-6}$alkylene-S—S—$C_{1-6}$alkylene-, or

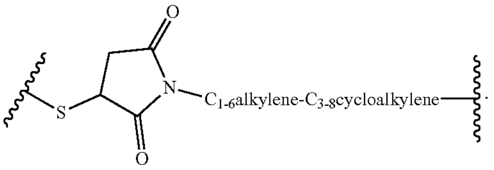
.

In further embodiments included in the foregoing, $L^{2b}$ is —C(O)$NR^{30}$-$L^{2c}$-, -cit-val-C(O)$C_{1-6}$alkylene-, —$NR^{30}$C(O)—, —$NR^{30}$C(O)-$L^{2c}$-, —$NR^{30}$C(O)O-$L^{2c}$-, -ala-val-C(O)$C_{1-6}$alkylene-, -cit-val-C(O)O—$C_{2-6}$alkylene-O—$C_{1-6}$alkylene-, -ala-val-C(O)O—$C_{2-6}$alkylene-O—$C_{1-6}$alkylene-, —S—S—$C_{1-6}$alkylene-, —NH—N=$C(R^{31})$-phenylene-O—$C_{1-6}$alkylene-,

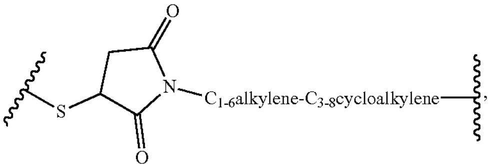
,

—$C_{1-6}$alkylene-, —$C_{2-6}$alkylene-O—, or $C_{3-8}$cycloalkylene, and $L^{2c}$ is —$C_{1-6}$alkylene-, —$C_{1-6}$alkylene-$NR^{30}$C(O)—$C_{1-6}$alkylene-S—S—$C_{1-6}$alkylene-, —$C_{1-6}$alkylene-$NR^{30}$C(O)NH—N=$C(R^{31})$-phenylene-O—$C_{1-6}$alkylene-, —$C_{3-8}$cycloalkylene, —($C_{2-6}$alkylene-O)—$C_{1-6}$alkylene-, —$C_{1-6}$alkylene-$C_{3-8}$cycloalkylene-, —$C_{3-8}$cycloalkylene-$C_{1-6}$alkylene-, —$C_{1-6}$alkylene-$C_{3-8}$cycloalkylene-$C_{1-6}$alkylene-, —$C_{1-6}$alkylene-S—S—$C_{1-6}$alkylene-, or

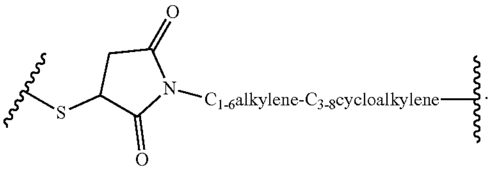
.

In further embodiments included in the foregoing, $L^{2b}$-$X^2$ is

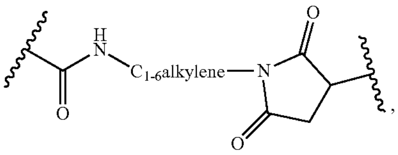
,

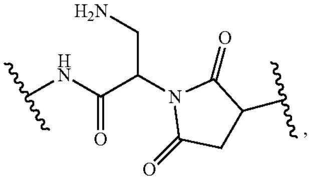
,

-continued

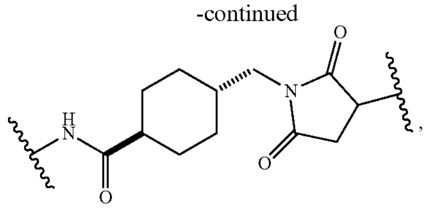

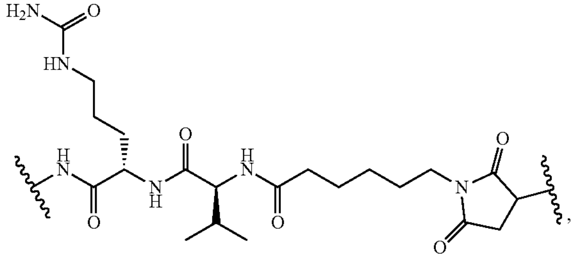

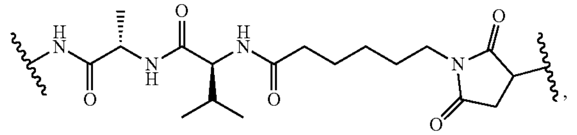

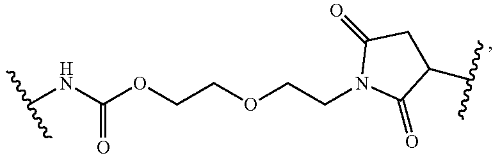

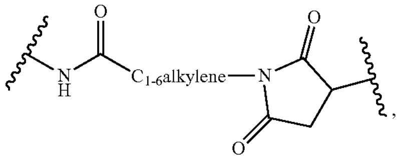

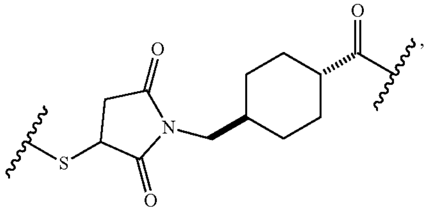

$-C(O)NR^{30}-C_{1-6}$alkylene-$NR^{30}C(O)-C_{1-6}$alkylene-S—S—$C_{1-6}$alkylene-C(O)—, $-C(O)NR^{30}-C_{1-6}$alkylene-$NR^{30}C(O)-C_{1-6}$alkylene-S—S—$C_{1-6}$alkylene-CH$(SO_3H)$—C(O)—, $-C(O)NR^{30}-C_{1-6}$alkylene-$NR^{30}C(O)$NH—N=C($R^{31}$)-phenylene-O—$C_{1-6}$alkylene-C(O)—, or

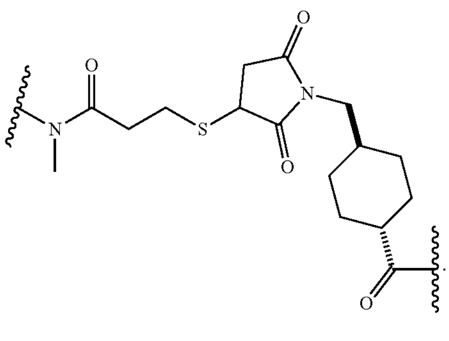

In some preferred embodiments according to formula (I), $R^9$ and $R^{10}$ are methyl.

In other preferred embodiments according to formula (I), $R^{11}$, $R^{12}$, and $R^{13}$ are each methyl.

In some embodiments according to formula (I), $R^{14}$ is H, $C_{1-6}$alkyl, $-C_{1-6}$alkylene-OH, $-C_{1-6}$alkylene-$C_{1-4}$alkoxy, $-C_{1-6}$alkylene-$CO_2H$, or $-C_{1-6}$alkylene-amide. In certain embodiments, $R^{14}$ is $-C_2$-$C_{30}$-alkylene-$CO_2H$. In certain embodiments, $R^{14}$ is $-CH_2CO_2H$; $-(CH_2)_2CO_2H$; $-(CH_2)_3CO_2H$; $-(CH_2)_4CO_2H$; $-(CH_2)_5CO_2H$; $-(CH_2)_6CO_2H$; $-(CH_2)_7CO_2H$; $-(CH_2)_8CO_2H$; $-(CH_2)_9CO_2H$; $-(CH_2)_{10}CO_2H$; $-(CH_2)_{11}CO_2H$; $-(CH_2)_{12}CO_2H$; $-(CH_2)_{13}CO_2H$; $-(CH_2)_{14}CO_2H$; $-(CH_2)_{15}CO_2H$; $-(CH_2)_{16}CO_2H$; $-(CH_2)_{17}CO_2H$; $-(CH_2)_{18}CO_2H$; $-(CH_2)_{19}CO_2H$; $-(CH_2)_{20}CO_2H$; $-(CH_2)_{21}CO_2H$; $-(CH_2)_{22}CO_2H$; $-(CH_2)_{23}CO_2H$; $-(CH_2)_{24}CO_2H$; $-(CH_2)_{25}CO_2H$; $-(CH_2)_{26}CO_2H$; $-(CH_2)_{27}CO_2H$; $-(CH_2)_{28}CO_2H$; $-(CH_2)_{29}CO_2H$; or $-(CH_2)_{30}CO_2H$. In certain embodiments, $R^{14}$ is $-(CH_2)_{15}CO_2H$. In preferred embodiments, $R^{14}$ is methyl.

In some embodiments, $R^{15}$ is H, $C_{1-6}$alkyl, $-C_{1-6}$alkylene-OH, $-C_{1-6}$alkylene-$C_{1-4}$alkoxy, $-C_{1-6}$alkylene-$CO_2H$, or $-C_{1-6}$alkylene-amide. In certain embodiments, $R^{15}$ is $CH_2CO_2H$; $(CH_2)_2CO_2H$; $(CH_2)_3CO_2H$; $(CH_2)_4$CO2H; $(CH_2)_5$CO2H; $(CH_2)_6$CO2H; $(CH_2)_7CO_2H$; $(CH_2)_8CO_2H$; $(CH_2)_9CO_2H$; $(CH_2)_{10}CO_2H$; $(CH_2)_{11}CO_2H$; $(CH_2)_{12}CO_2H$; $(CH_2)_{13}CO_2H$; $(CH_2)_{14}CO_2H$; $(CH_2)_{15}CO_2H$; $(CH_2)_{16}CO_2H$; $(CH_2)_{17}CO_2H$; $(CH_2)_{18}CO_2H$; $(CH_2)_{19}CO_2H$; $(CH_2)_{20}CO_2H$; $(CH_2)_{21}CO_2H$; $(CH_2)_{22}CO_2H$; $(CH_2)_{23}CO_2H$; $(CH_2)_{24}CO_2H$; $(CH_2)_{25}CO_2H$; $(CH_2)_{26}CO_2H$; $(CH_2)_{27}CO_2H$; $(CH_2)_{28}CO_2H$; $(CH_2)_{29}CO_2H$; or $(CH_2)_{30}CO_2H$. In certain embodiments, $R^{15}$ is $-(CH_2)_{15}CO_2H$.

In other preferred embodiments, $R^{17}$ is hydrogen.

In preferred embodiments, one of m and n is 1, and the other is 0.

In certain embodiments, x is 1 to 10, 1 to 8, 1 to 6, 1 to 5, 1 to 4, 1 to 3, or 1 to 2. In certain embodiments, x is 1, 2, 3, 4, 5, 6, 7, 8, 9, 10, 11, 12, 13, 14, 15, 16, 17, 18, 19, or 20.

In preferred embodiments, G is formula (II). In further embodiments formula (II) is formula (IIA), (IIA)

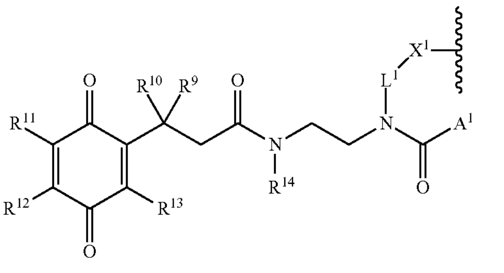

wherein $R^9$, $R^{10}$, $R^{11}$, $R^{12}$, $R^{13}$, $R^{14}$, $L^1$, $X^1$, and $A^1$ are as defined herein. In some embodiments, $L^1$-$X^1$ is

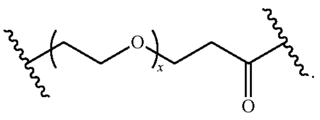

In certain embodiments, x is 2, 3, or 4.

In other preferred embodiments are conjugates wherein G is formula (IIB)

(IIB)

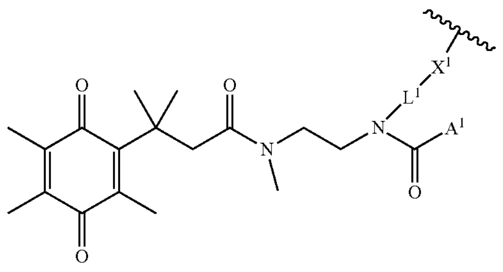

wherein $L^1$, $X^1$, and $A^1$ are as defined herein.

In other preferred embodiments are conjugates wherein G is formula (IIB-1)

(IIB-1)

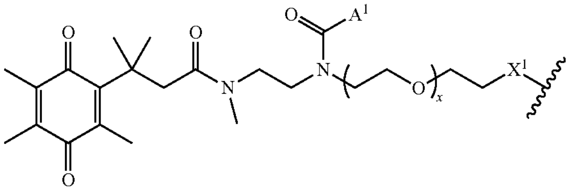

wherein x, $X^1$, and $A^1$ are as defined herein. In further embodiments according to (IIB-1), x is 2, 3, or 4. In further embodiments according to the foregoing, $X^1$ is

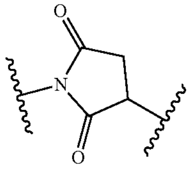 [SMILES: *C1CC(=O)N(*)C1=O]

or —C(O)—.

In preferred embodiments, G is formula (III). In further embodiments formula (III) is formula (IIIA), (III-A)

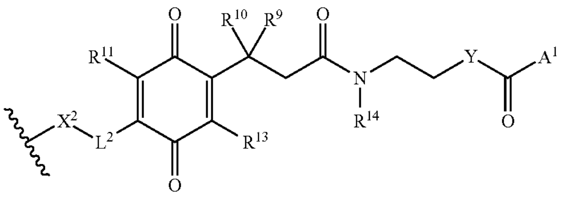

wherein $R^9$, $R^{10}$, $R^{11}$, $R^{13}$, $R^{14}$, $L^2$, $X^2$, Y, and $A^1$ are as defined herein.

In other preferred embodiments are conjugates wherein G is formula (IIIB)

(III-B)

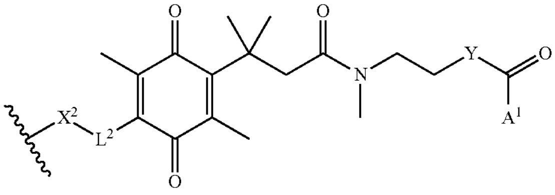

wherein $L^2$, $X^2$, Y, and $A^1$ are as defined herein.

In further embodiments formula (III) is formula (IIIC), (IIIC)

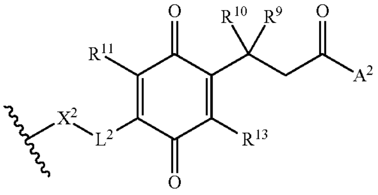

wherein $R^9$, $R^{10}$, $R^{11}$, $R^{13}$, $L^2$, $X^2$, and $A^2$ are as defined herein.

In other preferred embodiments are conjugates wherein G is formula (IIID)

(IIID)

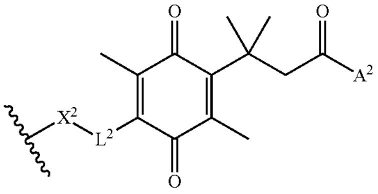

wherein $L^2$, $X^2$, and $A^2$ are as defined herein.

In further embodiments formula (III) is formula (IIIE), (IIIE)

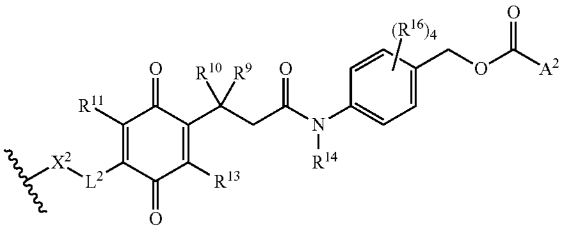

wherein $R^9$, $R^{10}$, $R^{11}$, $R^{13}$, $R^{14}$, $R^{16}$, $L^2$, $X^2$, and $A^2$ are as defined herein.

In other preferred embodiments are conjugates wherein G is formula (IIIF)

(IIIF)

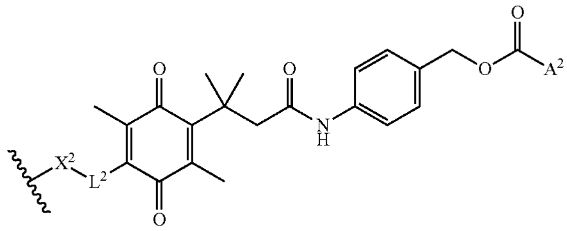

wherein $L^2$, $X^2$, and $A^2$ are as defined herein.

In preferred embodiments, G is formula (IV). In further embodiments formula (IV) is formula (IVA), (IVA)

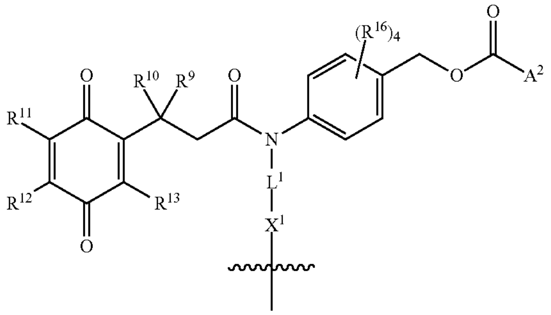

wherein $R^9$, $R^{10}$, $R^{11}$, $R^{12}$, $R^{13}$, $R^{16}$, $L^1$, $X^1$, and $A^2$ are as defined herein. In some embodiments, $L^1$-$X^1$ is

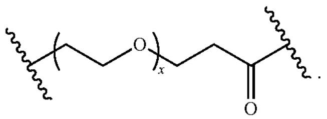

In certain embodiments, x is 2, 3, or 4.

In preferred embodiments, G is formula (V), wherein (V)

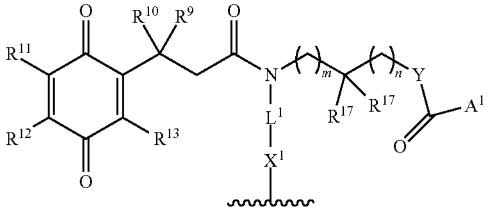

$R^9$, $R^{10}$, $R^{11}$, $R^{12}$, $R^{13}$, $R^{17}$, $L^1$, $X^1$, Y, $A^1$, m, and n are as defined herein. In some embodiments, $L^1$-$X^1$ is

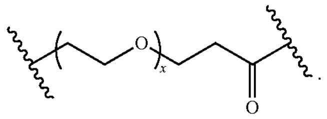

In certain embodiments, x is 2, 3, or 4.

In further embodiments, formula (V) is formula (VA), (VA)

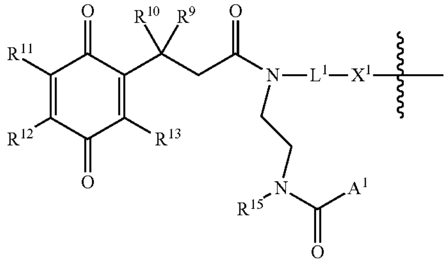

wherein $R^9$, $R^{10}$, $R^{11}$, $R^{12}$, $R^{13}$, $R^{15}$, $L^1$, X, and $A^1$ are as defined herein. In some embodiments, $L^1$-$X^1$ is

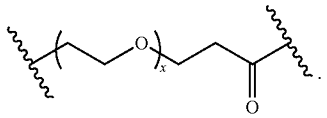

In certain embodiments, x is 2, 3, or 4.

In other preferred embodiments are conjugates wherein G is formula (VA-1)

(VA-1)

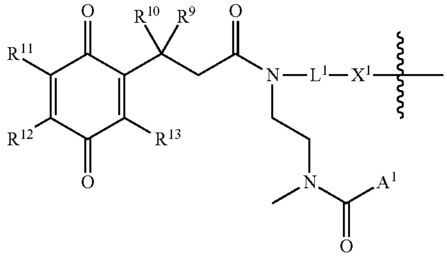

wherein $R^9$, $R^{10}$, $R^{11}$, $R^{12}$, $R^{13}$, $L^1$, $X^1$, and $A^1$ are as defined herein.

In other preferred embodiments are conjugates wherein G is formula (VA-2)

(VA-2)

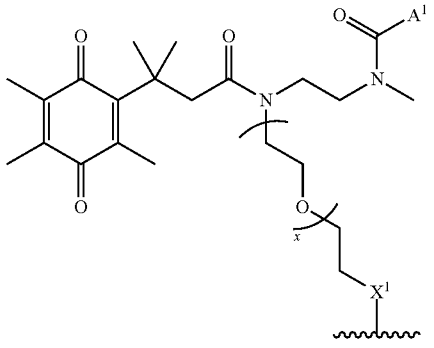

wherein x, $X^1$, and $A^1$ are as defined herein. In further embodiments according to (VA-2), x is 2, 3, or 4. In further embodiments according to the foregoing, $X^1$ is

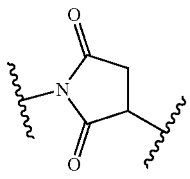 [SMILES: *C1CC(=O)N(*)C1=O]

or —C(O)—.

In some embodiments, p is a number from 1 to 10. In other embodiments, p is a number from 1 to 5. In still other embodiments, p is a number from 2-5. In still other embodiments, p is 3, 4, or 5. In a composition comprising a plurality of conjugates of formula (I), p represents the average number of groups G per antibody, also referred to as a drug-to-antibody ratio (DAR). Thus, in a composition comprising a plurality of conjugates p may have non-integer values (e.g., 3.5). In some embodiments, the DAR is from 2-5. In still other embodiments, the DAR is from 3-5. The preferred DAR may vary according to the particular antibody, payload, linker, and condition to be treated.

3. Conjugation Reagents

According to other aspects of the invention are conjugation reagents and their chemical precursors for coupling with an antibody or other cell binding agent. In the conjugation reagents, $X^{1a}/X^{2a}$ is a reactive functional group suitable for coupling with an amino, sulfhydryl, or N-terminal cysteine of an antibody; or a non-natural amino acid comprising an azido- or alkyne-containing side chain in a modified antibody; or $X^{1a}/X^{2a}$ is a protected reactive functional group, or is a chemical precursor to the reactive functional group.

Additionally, the conjugation reagents may be used to label non-biological agents, including but not limited to, solid supports/surfaces, nanoparticles, such as [60] fullerene, core-shell nanoparticles, liposome, dendrimer, and gold nanoparticles, and detergents. The detergent may be comprised within a liposome and/or solid-lipid nanoparticle (SLN) that may optionally be used to test drug delivering efficiency. The detergent may be a transfecting reagent such as Lipofectamine 2000 or Fugene 6.

In some aspects, the conjugation reagents can be conjugated with a nucleoside, nucleotide, or a polynucleotide. The conjugation reagents of the invention may be conjugated with a nucleoside, nucleotide, or polynucleotide in any way known to one of ordinary skill in the art such as through a phosphoramidite, an activated ester, or a reactive platinum complex. In certain embodiments, the labeling conjugation reagents may be conjugated to an agent using an activated carboxylic acid such as an NHS ester, pentafluorobenzene ester, an anhydride, an acetyl chloride, or using direct carboxylic acid and amine coupling reactions, or click chemistry, or maleimide, or activated carbonate, or phosphoramidite.

For example, a conjugation reagent can be attached to dU allylamine phosphoamidite and further incorporated in oligomers of interest by a traditional phosphoamidite chemistry. Alternatively, dU allylamine modified oligomers of interest can be labeled with the conjugation reagent through an activated ester by post labeling. If the labeled oligomers are primers of interest, they can also be used to amplify a sequence of interest through PCR.

In other aspects the conjugation reagents include compounds of formulas 7 or 10, or their salts,

7

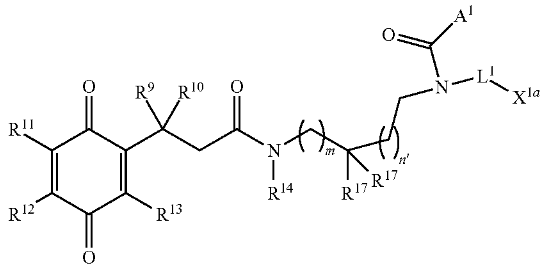

10

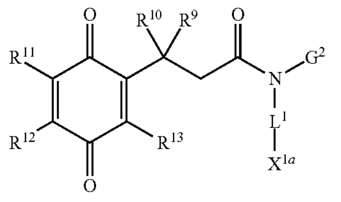

wherein $R^9$, $R^{10}$, $R^{11}$, $R^{12}$, $R^{13}$, $R^{14}$, $R^{17}$, $L^1$, $X^{1a}$, $G^2$, m, n', and $A^1$ are as defined herein.

In some embodiments, $L^1$ is $L^{1a}$ or $L^{1a}$-$L^{1b}$, wherein $L^{1b}$ is bonded to $X^{1a}$; $L^{1a}$ is —$C_{1-12}$alkylene-, —($C_{2-6}$alkylene-O)$_x$—$C_{1-6}$alkylene-, or $C_{3-8}$cycloalkylene; $L^{1b}$ comprises, or consists of, one or more covalently bonded divalent members, the one or more divalent members being selected from —$C_{1-6}$alkylene-, —$C_{2-6}$alkylene-O—, $C_{3-8}$cycloalkylene, —C(O)—, —O—, —S—, —S(O)—, —$S(O)_2$—, —$NR^{20}$—, —$C(R^{21})$=N—NH—, —$CH(CO_2H)$—,

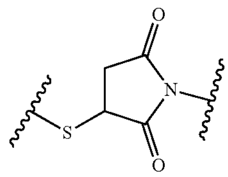

, an amino acid moiety, and phenylene; wherein the $C_{3-8}$cycloalkylene and phenylene of $L^{1a}$ and/or $L^{1b}$ is optionally independently substituted with 1-4 substituents independently selected from the group consisting of $C_{1-4}$alkyl, $C_{1-4}$haloalkyl, $C_{1-4}$alkoxy, halo, cyano, or hydroxy; $R^{20}$ and $R^{21}$ at each occurrence are independently hydrogen or $C_{1-4}$alkyl; and x is an integer from 1 to 20.

In other embodiments included in the foregoing, $L^{1b}$ is —C(O)$NR^{20}$-$L^{1c}$-, —$NR^{20}$C(O)-$L^{1c}$-, —$NR^{20}$C(O)O-$L^{1c}$-, —C(O)-$L^{1c}$-, —O-$L^{1c}$-, —S-$L^{1c}$-, —S(O)-$L^{1c}$-, —$S(O)_2$-$L^{1c}$-, or —$NR^{20}$-$L^{1c}$-; and $L^{1c}$ is —$C_{1-6}$alkylene-, —$C_{1-6}$alkylene-$NR^{20}$C(O)—$C_{1-6}$alkylene-S—S—$C_{1-6}$alkylene-, —$C_{1-6}$alkylene-$NR^{20}$C(O)NH—N═C($R^{21}$)-phenylene-O—$C_{1-6}$alkylene-, $C_{3-8}$cycloalkylene, —($C_{2-6}$alkylene-O)—$C_{1-6}$alkylene-, —$C_{1-6}$alkylene-$C_{3-8}$cycloalkylene-, —$C_{3-8}$cycloalkylene-$C_{1-6}$alkylene-, —$C_{1-6}$alkylene-$C_{3-8}$cycloalkylene-$C_{1-6}$alkylene-, —$C_{1-6}$alkylene-S—S—$C_{1-6}$alkylene-, or

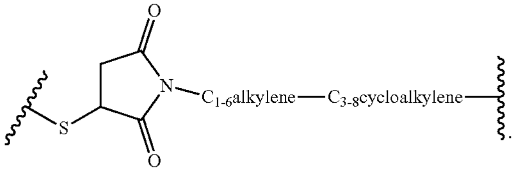
.

In other embodiments included in the foregoing, $L^{1b}$ is —C(O)$NR^{20}$-$L^{1c}$-, -cit-val-C(O)$C_{1-6}$alkylene-, —$NR^{20}$C(O)—, —$NR^{20}$C(O)-$L^{1c}$-$NR^{20}$C(O)O-$L^{1c}$-, -ala-val-C(O)$C_{1-6}$alkylene-, -cit-val-C(O)O—$C_{2-6}$alkylene-O—$C_{1-6}$alkylene-, -ala-val-C(O)O—$C_{2-6}$alkylene-O—$C_{1-6}$alkylene-, —S—S—$C_{1-6}$alkylene-, —NH—N═C($R^{21}$)-phenylene-O—$C_{1-6}$alkylene-,

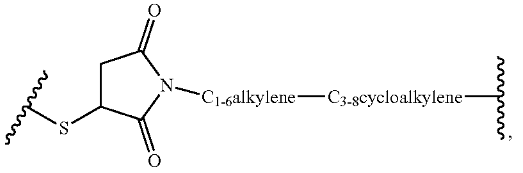
,

—$C_{1-6}$alkylene-, —$C_{2-6}$alkylene-O—, or $C_{3-8}$cycloalkylene, and $L^{1c}$ is —$C_{1-6}$alkylene-, —$C_{1-6}$alkylene-$NR^{20}$C(O)—$C_{1-6}$alkylene-S—S—$C_{1-6}$alkylene-, —$C_{1-6}$alkylene-$NR^{20}$C(O)NH—N═C($R^{21}$)-phenylene-O—$C_{1-6}$alkylene-, $C_{3-8}$cycloalkylene, —($C_{2-6}$alkylene-O)—$C_{1-6}$alkylene-, —$C_{1-6}$alkylene-$C_{3-8}$cycloalkylene-, —$C_{3-8}$cycloalkylene-$C_{1-6}$alkylene-, —$C_{1-6}$alkylene-$C_{3-8}$cycloalkylene-$C_{1-6}$alkylene-, —$C_{1-6}$alkylene-S—S—$C_{1-6}$alkylene-, or

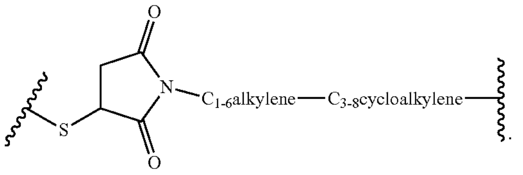
.

In other embodiments included in the foregoing, $L^{1a}$-$L^{1b}$ is —$C_{1-12}$alkylene-C(O)$NR^{20}$-$L^{1c}$-, —($C_{2-6}$alkylene-O)$_x$—$C_{1-6}$alkylene-C(O)$NR^{20}$-$L^{1c}$-, $C_{3-8}$cycloalkylene-C(O)$NR^{20}$-$L^{1c}$, $C_{1-12}$alkylene-$NR^{20}$C(O)-$L^{1c}$-, —($C_{2-6}$alkylene-O)$_x$—$C_{1-6}$alkylene-$NR^{20}$C(O)-$L^{1c}$-, —$C_{3-8}$cycloalkylene-$NR^{20}$C(O)-$L^{1c}$-, —($C_{2-6}$alkylene-O)$_x$—$C_{1-6}$alkylene-cit-val-C(O)$C_{1-6}$alkylene-, —($C_{2-6}$alkylene-O)—$C_{1-6}$alkylene-ala-val-C(O)$C_{1-6}$alkylene-, —$C_{1-12}$alkylene-$C_{3-8}$cycloalkylene-, —$C_{3-8}$cycloalkylene-$C_{1-2}$alkylene-, —$C_{1-6}$alkylene-$C_{3-8}$cycloalkylene-$C_{1-6}$alkylene-, —($C_{2-6}$alkylene-O)$_x$—$C_{1-6}$alkylene-$C_{3-8}$cycloalkylene-, or —($C_{2-6}$alkylene-O)$_x$—$C_{1-6}$alkylene-$C_{3-8}$cycloalkylene-$C_{1-6}$alkylene-.

In other embodiments included in the foregoing, $L^{1a}$ is —$(CH_2CH_2O)_{1-2}$—$CH_2CH_2$—; $L^{1b}$ is —C(O)$NR^{20}$-$L^{1c}$-, -ala-val-C(O)$(CH_2)_5$—, -cit-val-C(O)$(CH_2)_5$—, or

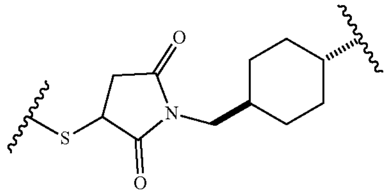
;

and $L^{1c}$ is —$CH_2CH_2$—, —$CH_2CH_2$—$NR^{20}$C(O)—$CH_2CH_2$—S—S—$CH(CH_3)CH_2CH_2$—, or —$CH_2CH_2$—$NR^{20}$C(O)NH—N═C($CH_3$)-1,4-phenylene-O—$CH_2CH_2CH_2$—, or

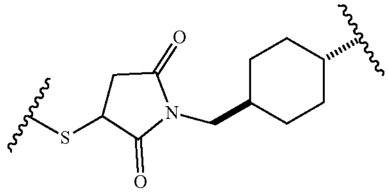
.

In other embodiments included in the foregoing, $L^{1b}$-$X^{1a}$ is

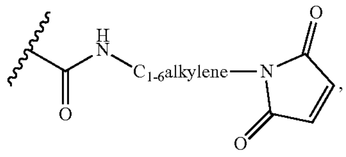
,

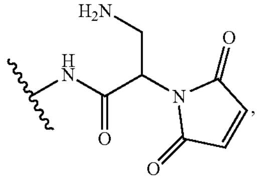
,

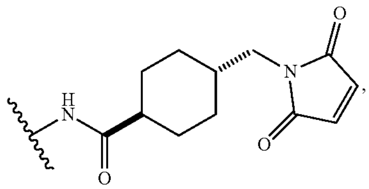
,

-continued
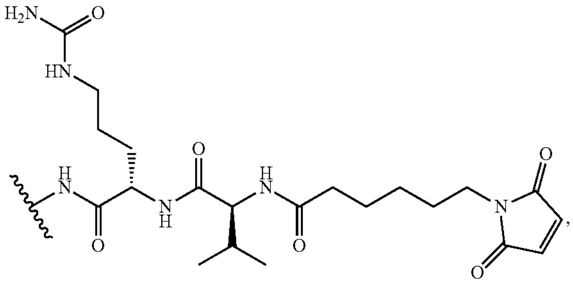,
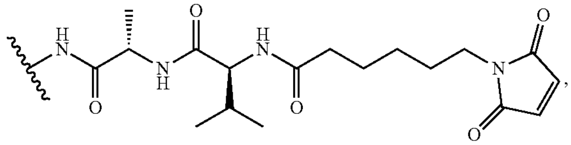,
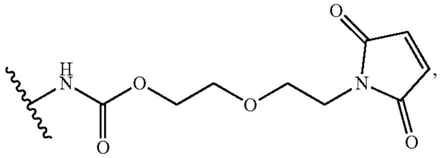,
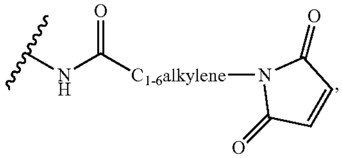,
-continued
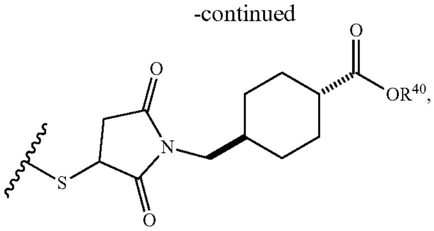
—C(O)NR$^{20}$—C$_{1-6}$alkylene-NR$^{20}$C(O)—C$_{1-6}$alkylene-S—S—C$_{1-6}$alkylene-C(O)—OR$^{40}$, —C(O)NR$^{20}$—C$_{1-6}$alkylene-NR$^{20}$C(O)—C$_{1-6}$alkylene-S—S—C$_{1-6}$alkylene-CH(SO$_3$H)—C(O)—OR$^{40}$, —C(O)NR$^{20}$—C$_{1-6}$alkylene-NR$^{20}$C(O)NH—N═C(R$^{21}$)-phenylene-O—C$_{1-6}$alkylene-C(O)—OR$^{40}$, or
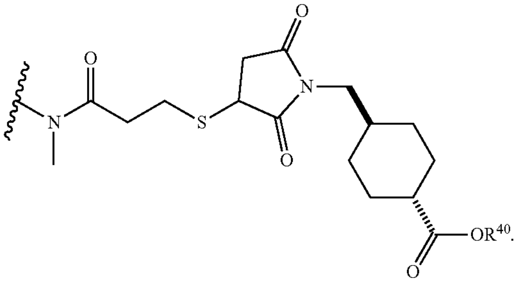
In other embodiments included in the foregoing, L$^1$-X$^{1a}$ is
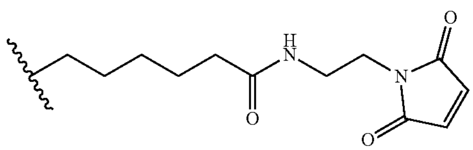,
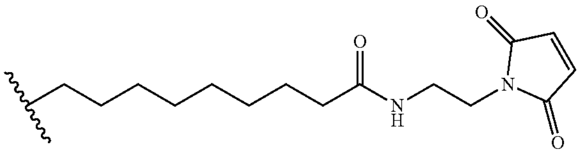,
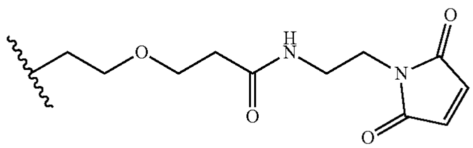,
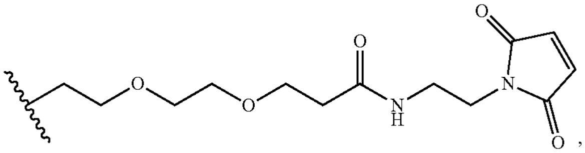,
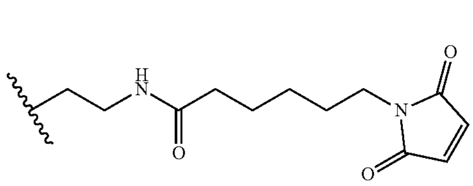,
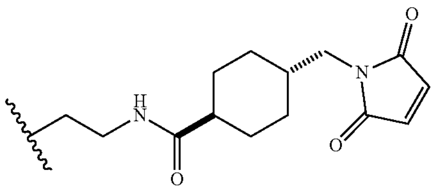,
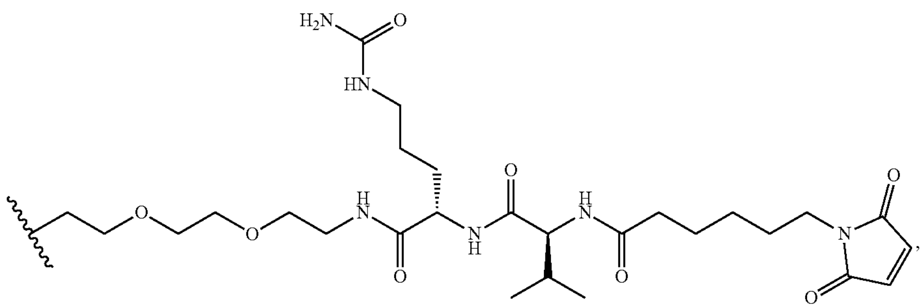, -continued
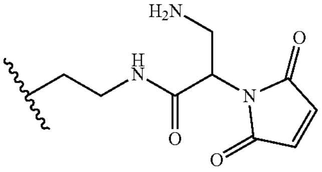,
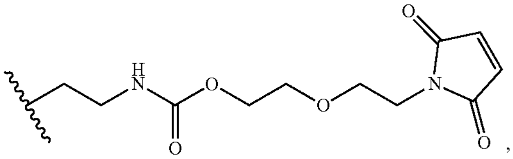,
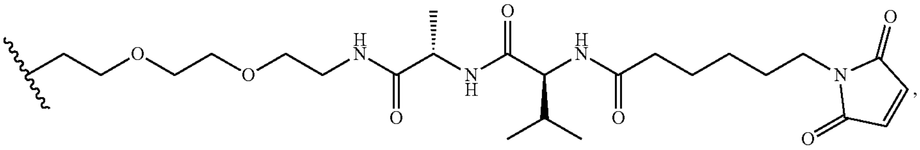,
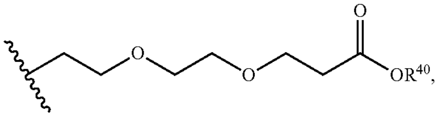,
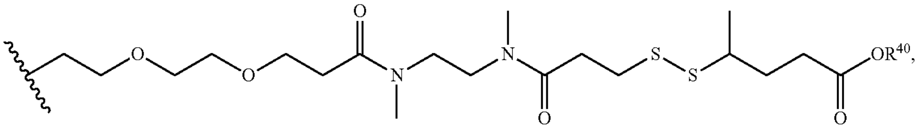,
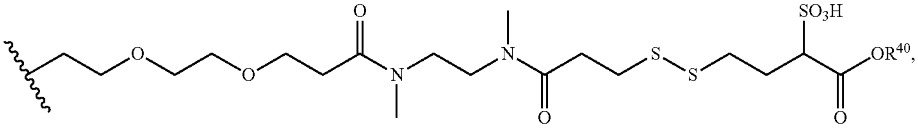,
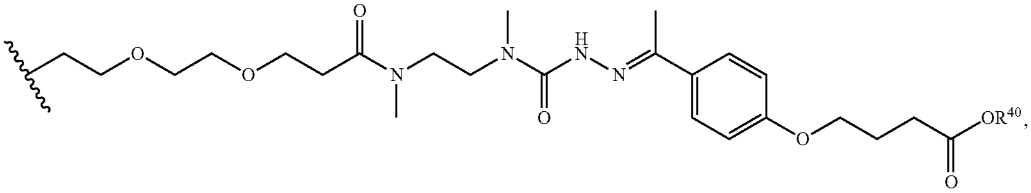, or
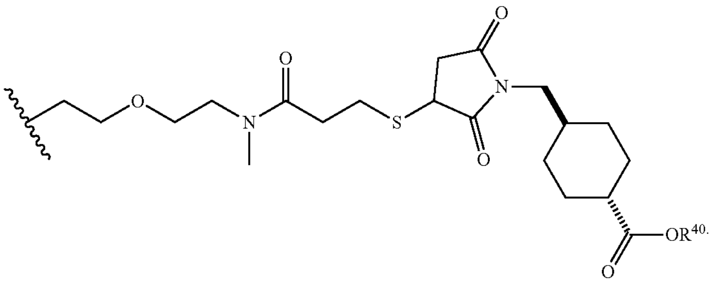.
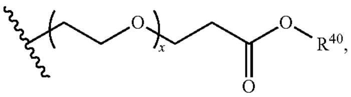,
wherein $R^{40}$ is as defined herein. In certain embodiments, $R^{40}$ is hydrogen. In certain embodiments, $R^{40}$ is
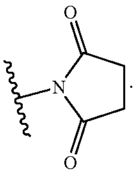 [SMILES: *N1C(=O)CCC1=O].
In certain embodiments, x is 2, 3, or 4.
In certain embodiments included in the foregoing, $L^1$-$X^{1a}$ is
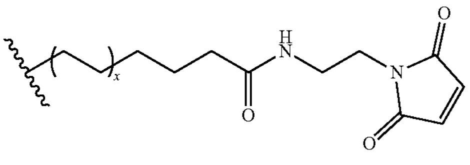
or
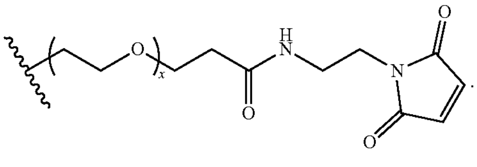.
In some preferred embodiments according to formula (7) or (10), $R^9$ and $R^{10}$ are methyl.

In other preferred embodiments according to formula (7) or (10), $R^{11}$, $R^{12}$, and $R^{13}$ are each methyl.

In some embodiments according to formula (7), $R^{14}$ is H, $C_{1-6}$alkyl, —$C_{1-6}$alkylene-OH, —$C_{1-6}$alkylene-$C_{1-4}$alkoxy, —$C_{1-6}$alkylene-$CO_2H$, or —$C_{1-6}$alkylene-amide. In certain embodiments, $R^{14}$ is —$C_2$-$C_{30}$-alkylene-$CO_2H$. In certain embodiments, $R^{14}$ is —$CH_2CO_2H$; —$(CH_2)_2CO_2H$; —$(CH_2)_3CO_2H$; —$(CH_2)_4CO_2H$; —$(CH_2)_5CO_2H$; —$(CH_2)_6CO_2H$; —$(CH_2)_7CO_2H$; —$(CH_2)_8CO_2H$; —$(CH_2)_9CO_2H$; —$(CH_2)_{10}CO_2H$; —$(CH_2)_{11}CO_2H$; —$(CH_2)_{12}CO_2H$; —$(CH_2)_{13}CO_2H$; —$(CH_2)_{14}CO_2H$; —$(CH_2)_{15}CO_2H$; —$(CH_2)_{16}CO_2H$; —$(CH_2)_{17}CO_2H$; —$(CH_2)_{18}CO_2H$; —$(CH_2)_{19}CO_2H$; —$(CH_2)_{20}CO_2H$; —$(CH_2)_{21}CO_2H$; —$(CH_2)_{22}CO_2H$; —$(CH_2)_{23}CO_2H$; —$(CH_2)_{24}CO_2H$; —$(CH_2)_{25}CO_2H$; —$(CH_2)_{26}CO_2H$; —$(CH_2)_{27}CO_2H$; —$(CH_2)_{28}CO_2H$; —$(CH_2)_{29}CO_2H$; or —$(CH_2)_{30}CO_2H$. In certain embodiments, $R^{14}$ is —$(CH_2)_{15}CO_2H$. In preferred embodiments, $R^{14}$ is methyl.

In some embodiments according to formula (10), $G^2$ is

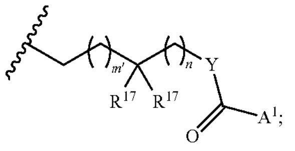

Y is $NR^{15}$; and $R^{15}$ is H, $C_{1-6}$alkyl, —$C_{1-6}$alkylene-OH, —$C_{1-6}$alkylene-$C_{1-4}$alkoxy, —$C_{1-6}$alkylene-$CO_2H$, or —$C_{1-6}$alkylene-amide.

In certain embodiments, $R^{15}$ is —$C_2$-$C_{30}$-alkylene-$CO_2H$. In certain embodiments, $R^{15}$ is $CH_2CO_2H$; $(CH_2)_2CO_2H$; $(CH_2)_3CO_2H$; $(CH_2)_4CO_2H$; $(CH_2)_5CO_2H$; $(CH_2)_6CO_2H$; $(CH_2)_7CO_2H$; $(CH_2)_8CO_2H$; $(CH_2)_9CO_2H$; $(CH_2)_{10}CO_2H$; $(CH_2)_{11}CO_2H$; $(CH_2)_{12}CO_2H$; $(CH_2)_{13}CO_2H$; $(CH_2)_{14}CO_2H$; $(CH_2)_{15}CO_2H$; $(CH_2)_{16}CO_2H$; $(CH_2)_{17}CO_2H$; $(CH_2)_{18}CO_2H$; $(CH_2)_{19}CO_2H$; $(CH_2)_{20}CO_2H$; $(CH_2)_{21}CO_2H$; $(CH_2)_{22}CO_2H$; $(CH_2)_{23}CO_2H$; $(CH_2)_{24}CO_2H$; $(CH_2)_{25}CO_2H$; $(CH_2)_{26}CO_2H$; $(CH_2)_{27}CO_2H$; $(CH_2)_{28}CO_2H$; $(CH_2)_{29}CO_2H$; or $(CH_2)_{30}CO_2H$. In certain embodiments, $R^{15}$ is —$(CH_2)_{15}CO_2H$.

In preferred embodiments, $R^{15}$ is methyl.

In other preferred embodiments of formula (7) or (10), $R^{17}$ is hydrogen.

In preferred embodiments of formula (7) or (10), m is 0 and n' is 0.

In certain embodiments of formula (7) or (10), x is 1 to 10, 1 to 8, 1 to 6, 1 to 5, 1 to 4, 1 to 3, or 1 to 2. In certain embodiments, x is 1, 2, 3, 4, 5, 6, 7, 8, 9, 10, 11, 12, 13, 14, 15, 16, 17, 18, 19, or 20.

In certain embodiments, the compound of formula (7) has formula (7A), or a salt thereof, (7A)

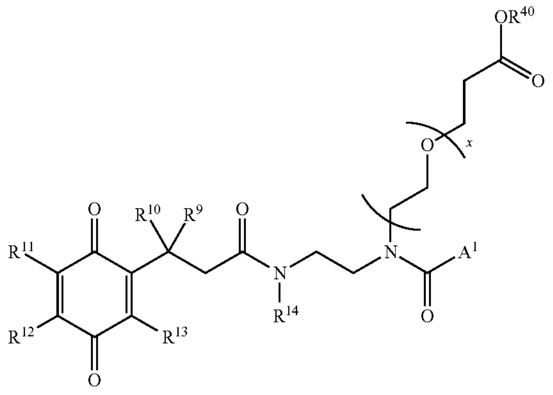

wherein $R^9$, $R^{10}$, $R^{11}$, $R^{12}$, $R^{13}$, $R^{14}$, $R^{40}$, x, and $A^1$ are as defined above.

In certain embodiments, the compound of formula (7) has formula (7B), or a salt thereof, (7B)

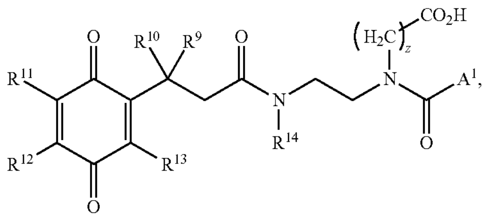

wherein z is an integer selected from 1 to 30; and $R^9$, $R^{10}$, $R^{11}$, $R^{12}$, $R^{13}$, $R^{14}$, and $A^1$ are as defined above. In certain embodiments, z is 16.

In other preferred embodiments are compounds of formula (7C)

(7C)

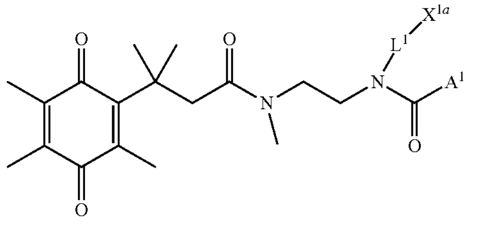

wherein $L^1$, $X^{1a}$, and $A^1$ are as defined herein.

In other preferred embodiments are compounds of formula (7E)

(7E)

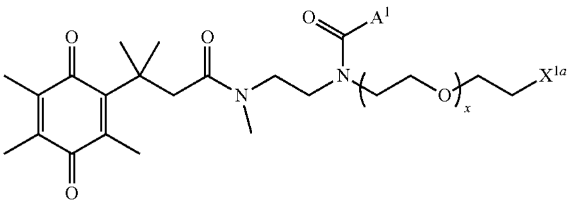

wherein x, $X^{1a}$, and $A^1$ are as defined herein. In further embodiments according to (7E), x is 2, 3, or 4. In further embodiments according to the foregoing, $X^{1a}$ is

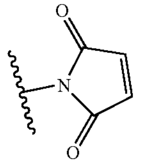 [SMILES: *N1C(=O)C=CC1=O]

or —C(O)OR$^{40}$

In certain embodiments, the compound of formula (10) has formula (10A)

(10A)

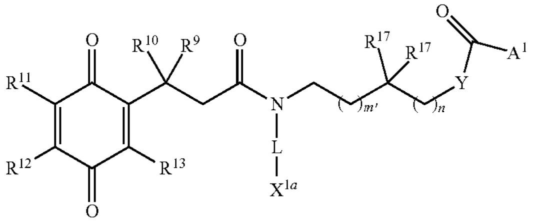

wherein $R^9$, $R^{10}$, $R^{11}$, $R^{12}$, $R^{13}$, $R^{17}$, Y, m', n, $L^1$, $X^{1a}$, and $A^1$ are as defined herein.

In certain embodiments, the compound of formula (10) has formula (10A-a), or a salt thereof, (10A-a)

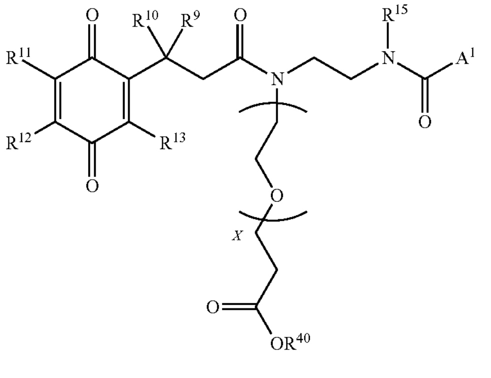

wherein $R^9$, $R^{10}$, $R^{11}$, $R^{12}$, $R^{13}$, $R^{15}$, $R^{40}$, x, and $A^1$ are as defined above.

In certain embodiments, the compound of formula (10) has formula (10A-b), or a salt thereof, (10A-b)

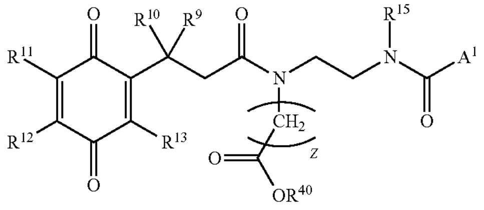

wherein z is an integer selected from 1 to 30; and $R^9$, $R^{10}$, $R^{11}$, $R^{12}$, $R^{13}$, $R^{15}$, and $A^1$ are as defined above. In certain embodiments, z is 16.

In other preferred embodiments are compounds of formula (10A-c)

(10A-c)

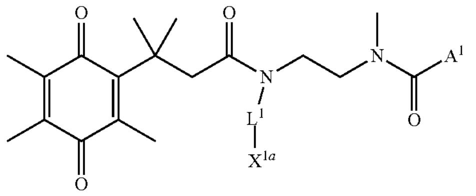

wherein $L^1$, $X^{1a}$, and $A^1$ are as defined herein.

In other preferred embodiments are compounds of formula (10A-d)

(10A-d)

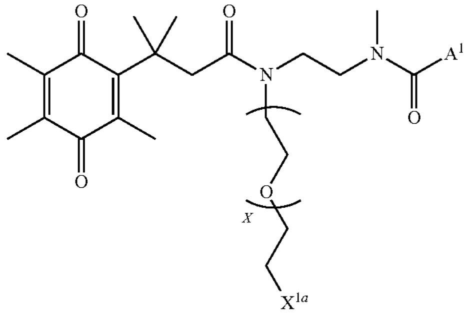

wherein x, $X^{1a}$, and $A^1$ are as defined herein. In further embodiments according to (10A-d), x is 2, 3, or 4. In further embodiments according to the foregoing, $X^{1a}$ is

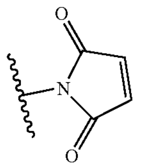 [SMILES: *N1C(=O)C=CC1=O]

or —C(O)OR$^{40}$

In certain embodiments, the compound of formula (10) has formula (10B)

(10B)

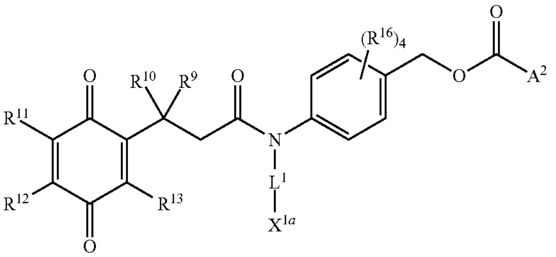

wherein $R^9$, $R^{10}$, $R^{11}$, $R^{12}$, $R^{13}$, $R^{16}$, $L^1$, $X^{1a}$, and $A^2$ are as defined above.

In other preferred embodiments are compounds of formula (10B-a), (10B-a)

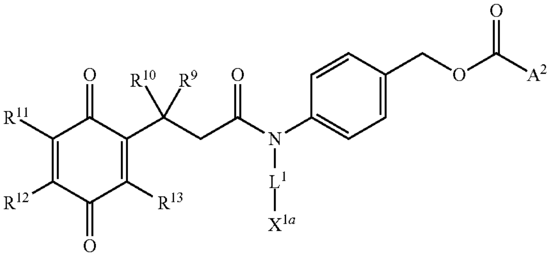

wherein $R^9$, $R^{10}$, $R^{11}$, $R^{12}$, $R^{13}$, $L^1$, $X^{1a}$, and $A^2$ are as defined above.

In other preferred embodiments are compounds of formula (10B-b), (10B-b)

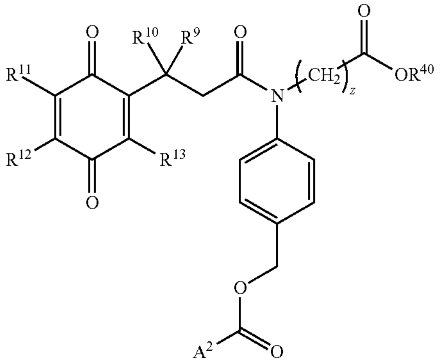

wherein $R^9$, $R^{10}$, $R^{11}$, $R^{12}$, $R^{13}$, $R^{40}$, z, and $A^2$ are as defined above.

In other preferred embodiments are compounds of formula (10B-c), (10B-c)

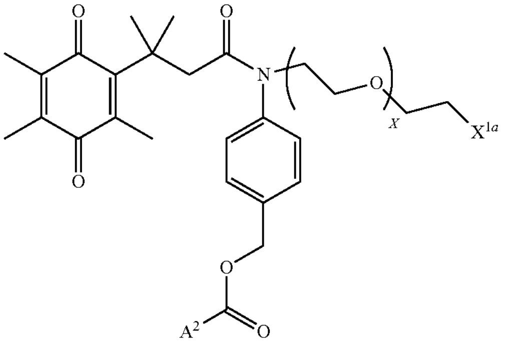

wherein x, $X^{1a}$, and $A^2$ are as defined above.

In another aspect the conjugation reagents are compounds of formula 12, or their salts,

12

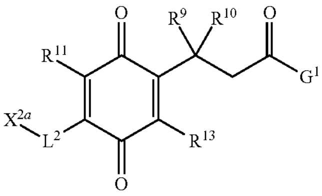

$G^1$ is $-A^2$,

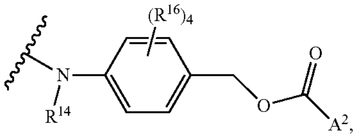

or

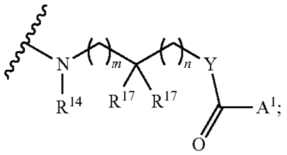

$R^9$ and $R^{10}$ are each independently selected from $C_{1-4}$alkyl;

$R^{11}$ and $R^{13}$ are each independently selected from the group consisting of H, $C_{1-4}$alkyl, $C_{1-4}$alkoxy, bromo, chloro and amino;

$L^2$ is a second linker moiety; Y is O or $NR^{15}$;

$R^{14}$ and $R^{15}$ are each independently H, $C_{1-30}$alkyl optionally substituted with 1-8 halogens, $-C_{1-30}$alkylene-OH, $-C_{1-30}$alkylene-$C_{1-4}$alkoxy, $-C_{1-30}$alkylene-COOH, or $-C_{1-30}$alkylene-amido;

$R^{16}$, at each occurrence, is independently H, halogen, $CH_3$, $OCH_3$, or $NO_2$;

$R^{17}$, at each occurrence, is independently H or $C_{1-4}$alkyl, or both $R^{17}$ together with the carbon to which they are attached form a cycloalkyl ring having from 3-7 carbons;

m is an integer from 0-2;

n is an integer from 0-2;

$X^{2a}$ is $—OSO_2R^{50}$, OH, —Cl, —Br, —I, $—N_3$, —C≡CH, —CN, COOH, $—COOR^{40}$, $—COJ^1$, $—CH(SO_3H)—C(O)OR^{40}$, —NCO, —NCS, $—C(O)CH_2J^1$,

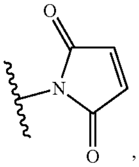
,
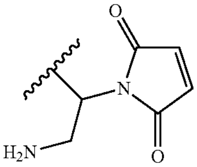
,
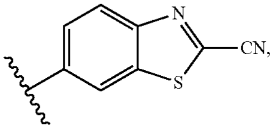

$—NH_2$, or $—NH(C_{1-6}alkyl)$;

$R^{40}$ is $C_{1-6}$alkyl, 4-nitrophenyl, pentafluorophenyl, tetrafluorophenyl, $—C(O)—OR^{41}$, or

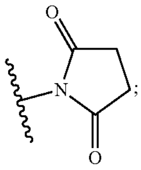 [SMILES: *N1C(=O)CCC1=O]
;

$R^{41}$ is $C_{1-6}$alkyl or phenyl;

$J^1$ is —Cl, —Br, —I, or $—OSO_2R^{50}$;

$R^{50}$ is $C_{1-6}$alkyl, $C_{1-6}$haloalkyl, phenyl, 4-methylphenyl, 4-nitrophenyl, or 4-bromophenyl;

$A^1$ is a payload moiety bonded through a substitutable oxygen or sulfur atom; and $A^2$ is a payload moiety bonded through a substitutable oxygen, sulfur, or nitrogen atom.

In some embodiments, $L^2$ is $L^{2a}$ or $L^{2a}$-$L^{2b}$, wherein $L^{2b}$ is bonded to $X^{2a}$; $L^{2a}$ is $—C_{2-6}$alkylene-; $L^{2b}$ comprises, or consists of, one or more covalently bonded divalent members, the one or more divalent members being selected from the group consisting of $—C_{1-6}$alkylene-, $—C_{2-6}$alkylene-O—, $C_{3-8}$cycloalkylene, —C(O)—, —O—, —S—, —S(O)—, $—S(O)_2—$, $—NR^{30}—$, $—C(R^{31})=N—N—$, $—CH(CO_2H)—$,

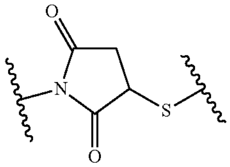
, an amino acid moiety, and phenylene; wherein the $C_{3-8}$cycloalkylene and phenylene of $L^{1b}$ are optionally independently substituted with 1-4 substituents independently selected from the group consisting of $C_{1-4}$alkyl, $C_{1-4}$haloalkyl, $C_1$ 4alkoxy, halo, cyano, and hydroxy; and $R^{30}$ and $R^{31}$ at each occurrence are independently hydrogen or $C_{1-4}$alkyl.

In further embodiments included in the foregoing, $L^{2b}$ is $—C(O)NR^{30}$-$L^{2c}$-, -cit-val-$C(O)C_{1-6}$alkylene-, $—NR^{30}C(O)—$, $—NR^{30}C(O)$-$L^{2c}$-, $—NR^{30}C(O)O$-$L^{2c}$-, -ala-val-C(O)$C_1$ 6alkylene-, -cit-val-C(O)O—$C_{2-6}$alkylene-O—$C_{1-6}$alkylene-, -ala-val-C(O)O—$C_{2-6}$alkylene-O—$C_{1-6}$alkylene-, —S—S—$C_{1-6}$alkylene-, $—NH—N=C(R^{31})$-phenylene-O—$C_{1-6}$alkylene-,

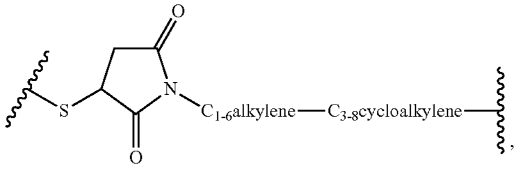
, $—C_{1-6}$alkylene-, $—C_{2-6}$alkylene-O—, or $C_{3-8}$cycloalkylene, and $L^2c$ is $—C_{1-6}$alkylene-, $—C_{1-6}$alkylene-$NR^{30}C(O)—C_{1-6}$alkylene-S—S—$C_{1-6}$alkylene-, $—C_{1-6}$alkylene-$NR^{30}C(O)NH—N=C(R^{31})$-phenylene-O—$C_{1-6}$alkylene-, $—C_{3-8}$cycloalkylene, $—(C_{2-6}$alkylene-O)—$C_{1-6}$alkylene-, $—C_{1-6}$alkylene-$C_{3-8}$cycloalkylene-, $—C_{3-8}$cycloalkylene-$C_{1-6}$alkylene-, $—C_{1-6}$alkylene-$C_{3-8}$cycloalkylene-$C_{1-6}$alkylene-, $—C_{1-6}$alkylene-S—S—$C_{1-6}$alkylene-, or

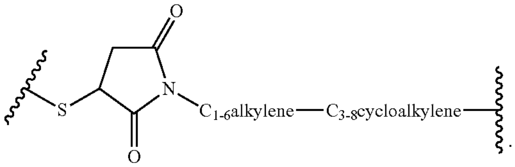
.

In further embodiments included in the foregoing, $L^{2b}$-$X^{2a}$ is

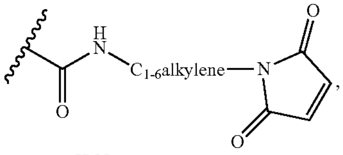
,

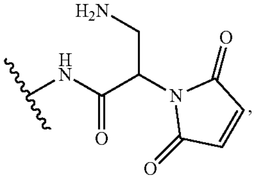
,

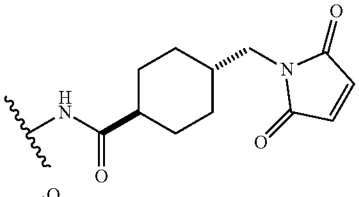
,

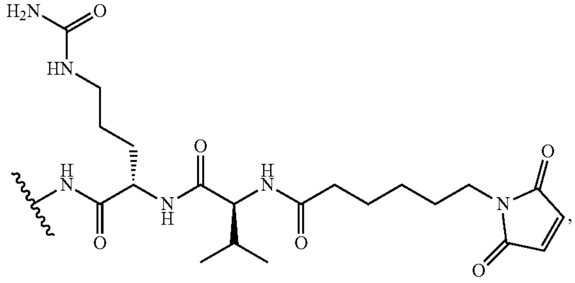
,

-continued

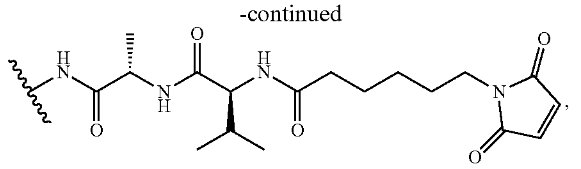

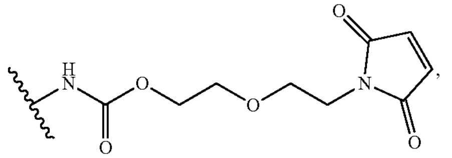

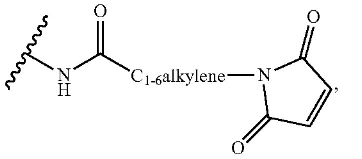

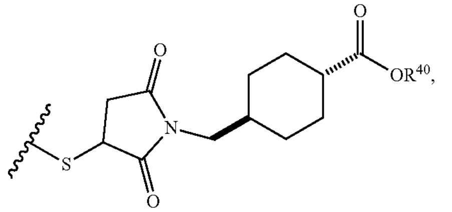

—C(O)NR$^{30}$—C$_{1-6}$alkylene-NR$^{30}$C(O)—C$_{1-6}$alkylene-S—S—C$_{1-6}$alkylene-C(O)—OR$^{40}$, —C(O)NR$^{30}$—C$_{1-6}$alkylene-NR$^{30}$C(O)—C$_{1-6}$alkylene-S—S—C$_{1-6}$alkylene-CH(SO$_3$H)—C(O)—OR$^{40}$, —C(O)NR$^{30}$—C$_{1-6}$alkylene-NR$^{30}$C(O)NH—N═C(R$^{31}$)-phenylene-O—C$_{1-6}$alkylene-C(O)—OR$^{40}$, or

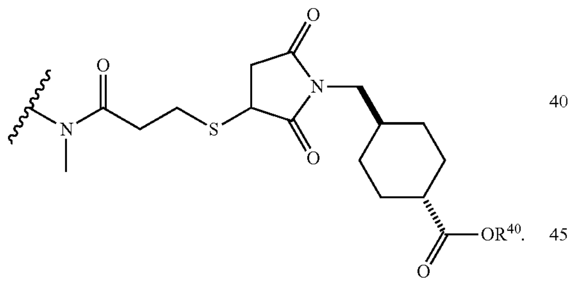

In some embodiments included in the foregoing, $L^2$ is $L^{2a}$-$L^{2b}$; $L^{2b}$ is —C(O)NR$^{30}$-$L^{2c}$- or —C(O)NR$^{30}$—. In still further embodiments included in the foregoing $L^{2a}$ is —$CH_2CH_2$—.

In some preferred embodiments according to formula (12), $R^9$ and $R^{10}$ are methyl.

In other preferred embodiments according to formula (12), $R^{11}$ and $R^{13}$ are each methyl.

In some embodiments according to formula (12), $R^{14}$ is H, C$_{1-6}$alkyl, —C$_{1-6}$alkylene-OH, —C$_{1-6}$alkylene-C$_{1-4}$alkoxy, —C$_{1-6}$alkylene-CO$_2$H, or —C$_{1-6}$alkylene-amide. In certain embodiments, $R^{14}$ is —C$_2$-C$_{30}$-alkylene-CO$_2$H. In certain embodiments, $R^{14}$ is —$CH_2CO_2H$; —$(CH_2)_2CO_2H$; —$(CH_2)_3CO_2H$; —$(CH_2)_4CO_2H$; —$(CH_2)_5CO_2H$; —$(CH_2)_6CO_2H$; —$(CH_2)_7CO_2H$; —$(CH_2)_8CO_2H$; —$(CH_2)_9CO_2H$; —$(CH_2)_{10}CO_2H$; —$(CH_2)_{11}CO_2H$; —$(CH_2)_{12}CO_2H$; —$(CH_2)_{13}CO_2H$; —$(CH_2)_{14}CO_2H$; —$(CH_2)_{15}CO_2H$; —$(CH_2)_{16}CO_2H$; —$(CH_2)_{17}CO_2H$; —$(CH_2)_{18}CO_2H$; —$(CH_2)_{19}CO_2H$; —$(CH_2)_{20}CO_2H$; —$(CH_2)_{21}CO_2H$; —$(CH_2)_{22}CO_2H$; —$(CH_2)_{23}CO_2H$; —$(CH_2)_{24}CO_2H$; —$(CH_2)_{25}CO_2H$; —$(CH_2)_{26}CO_2H$; —$(CH_2)_{27}CO_2H$; —$(CH_2)_{28}CO_2H$; —$(CH_2)_{29}CO_2H$; or —$(CH_2)_{30}CO_2H$. In certain embodiments, $R^{14}$ is —$(CH_2)_{15}CO_2H$. In preferred embodiments, $R^{14}$ is methyl.

In some embodiments, $R^{15}$ is H, C$_{1-6}$alkyl, —C$_{1-6}$alkylene-OH, —C$_{1-6}$alkylene-C$_{1-4}$alkoxy, —C$_{1-6}$alkylene-CO$_2$H, or —C$_{1-6}$alkylene-amide.

In certain embodiments, $R^{15}$ is $CH_2CO_2H$; $(CH_2)_2CO_2H$; $(CH_2)_3CO_2H$; $(CH_2)_4CO_2H$; $(CH_2)_5CO_2H$; $(CH_2)_6CO_2H$; $(CH_2)_7CO_2H$; $(CH_2)_8CO_2H$; $(CH_2)_9CO_2H$; $(CH_2)_{10}CO_2H$; $(CH_2)_{11}CO_2H$; $(CH_2)_{12}CO_2H$; $(CH_2)_{13}CO_2H$; $(CH_2)_{14}CO_2H$; $(CH_2)_{15}CO_2H$; $(CH_2)_{16}CO_2H$; $(CH_2)_{17}CO_2H$; $(CH_2)_{18}CO_2H$; $(CH_2)_{19}CO_2H$; $(CH_2)_{20}CO_2H$; $(CH_2)_{21}CO_2H$; $(CH_2)_{22}CO_2H$; $(CH_2)_{23}CO_2H$; $(CH_2)_{24}CO_2H$; $(CH_2)_{25}CO_2H$; $(CH_2)_{26}CO_2H$; $(CH_2)_{27}CO_2H$; $(CH_2)_{28}CO_2H$; $(CH_2)_{29}CO_2H$; or $(CH_2)_{30}CO_2H$. In certain embodiments, $R^{15}$ is —$(CH_2)_{15}CO_2H$.

In preferred embodiments, $R^{15}$ is methyl.

In other preferred embodiments, $R^{17}$ is hydrogen.

In preferred embodiments, one of m and n is 1, and the other is 0.

4. Pharmaceutical Compositions

In another preferred embodiment, the present invention provides a pharmaceutical formulation comprising a conjugate of the invention and a pharmaceutically acceptable carrier. The conjugates described herein including pharmaceutically acceptable carriers can be delivered to a patient using parenteral administration, including intramuscular, subcutaneous, and intravenous injections. Preferably, the conjugates of the invention comprising an antibody or antibody fragment as the targeting moiety are administered parenterally, more preferably intravenously.

The conjugates may be formulated for parenteral administration by injection, e.g., by bolus injection or continuous infusion. Injection is a preferred method of administration for the compositions of the current invention. Formulations for injection may be presented in unit dosage form, e.g., in ampoules or in multi-dose containers, with an added preservative. The compositions may take such forms as suspensions, solutions or emulsions in oily or aqueous vehicles. The compositions may take the form of liposomes or nanoparticles. Such liquids may additionally contain other pharmaceutically acceptable ingredients, such as anti-oxidants, buffers, preservatives, stabilizers, bacteriostats, suspending agents, thickening agents, and solutes which render the formulation isotonic with the blood (or other relevant bodily fluid) of the intended recipient. Suspending, stabilizing and/or dispersing agents may be added such as the cross-linked polyvinyl pyrrolidone, agar, or alginic acid or a salt thereof such as sodium alginate. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 μg/ml, for example from about 10 ng/ml to about 1 μg/ml.

Pharmaceutical formulations for parenteral administration include aqueous solutions of the conjugates in water-soluble form. Additionally, suspensions of the conjugates may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions. For injection, the agents of the invention may be formulated in aqueous solutions, preferably in physiologically compatible buffers such as Hanks's solution, Ringer's solution, or physiological saline buffer.

Alternatively, the conjugate may be in powder form for constitution with a suitable vehicle, e.g., sterile pyrogen-free water, before use. In addition to the formulations described previously, the conjugates may also be formulated as a depot preparation. Such long acting formulations may be administered by implantation or transcutaneous delivery (e.g., subcutaneously or intramuscularly), intramuscular injection, or a transdermal patch. Thus, for example, the conjugates may be formulated with suitable polymeric or hydrophobic materials (e.g., as an emulsion in an acceptable oil) or ion exchange resins, or as sparingly soluble derivatives, for example, as a sparingly soluble salt.

Suitable carriers, diluents, excipients, etc., can be found in standard pharmaceutical texts. See, for example, Handbook of Pharmaceutical Additives, 2nd Edition (eds. M. Ash and I. Ash), 2001 (Synapse Information Resources, Inc., Endicott, N.Y., USA), Remington's Pharmaceutical Sciences, 20th edition, pub. Lippincott, Williams & Wilkins, 2000; and Handbook of Pharmaceutical Excipients, 2nd edition, 1994.

Compounds and conjugates may be in the form of a salt, such as a pharmaceutically acceptable salt. The phrase "pharmaceutically acceptable salt," as used herein, refers to pharmaceutically acceptable organic or inorganic salts. Acid addition salts can be formed with an amino group. Preferred salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

A preferred pharmaceutical composition is a composition formulated for injection such as intravenous injection and includes about 0.01% to about 100% by weight of the drug conjugate, based upon 100% weight of total pharmaceutical composition.

5. Methods

A. Drug Conjugate Methods of Use

The present invention provides a number of methods that can be practiced utilizing the compounds and conjugates of the invention. Methods for using the drug conjugate of the current invention include: killing or inhibiting the growth or replication of a tumor cell or cancer cell, treating cancer, treating a pre-cancerous condition, killing or inhibiting the growth or replication of a cell that expresses an autoimmune antibody, treating an autoimmune disease, treating an infectious disease, preventing the multiplication of a tumor cell or cancer cell, preventing cancer, preventing the multiplication of a cell that expresses an autoimmune antibody, preventing an autoimmune disease, preventing an infectious disease, and cell ablation. These methods of use comprise administering to an animal such as a mammal or a human in need thereof an effective amount of an antibody drug conjugate. Preferred drug conjugates for many of the methods of use described herein include antibodies and antibody fragments, which target the particular tumor cell, cancer cell, or other target area.

The drug conjugate of the current invention may be useful for treating cancer, autoimmune disease and infectious disease in an animal. Compositions and methods for treating tumors by providing a subject the composition in a pharmaceutically acceptable manner with a pharmaceutically effective amount of a composition of the present invention are provided.

The drug conjugates may be particularly useful for the treatment of cancer and for the inhibition of the multiplication of a tumor cell or cancer cell in an animal. Cancer, or a precancerous condition, includes, but is not limited to, a tumor, metastasis, or any disease or disorder characterized by uncontrolled cell growth, can be treated or prevented by administration of the antibody drug conjugates of the current invention. The conjugate delivers a payload to a tumor cell or cancer cell. In one embodiment, the antibody drug conjugate specifically binds to or associates with a cancer-cell or a tumor-cell-associated antigen. The conjugate can be taken up inside a tumor cell or cancer cell through, for example, receptor-mediated endocytosis. The antigen can be attached to a tumor cell or cancer cell or can be an extracellular matrix protein associated with the tumor cell or cancer cell. Once inside the cell, the quinone moiety may be reduced leading to release of the drug as described above. The released drug may freely diffuse and induce cytotoxic activities.

The conjugate may bind to, for example, a tumor cell or cancer cell, a tumor cell or cancer cell antigen, which is on the surface of the tumor cell or cancer cell, or a tumor cell or cancer cell antigen, which is an extracellular matrix protein associated with the tumor cell or cancer cell. An antibody may be designed specifically for a particular tumor cell or cancer cell type. Therefore, the type of tumors or cancers that may be effectively treated can be altered by the choice of antibody.

Representative examples of precancerous conditions that may be targeted by the conjugate, include, but are not limited to: metaplasia, hyperplasia, dysplasia, colorectal polyps, actinic ketatosis, actinic cheilitis, human papillomaviruses, leukoplakia, lychen planus, and Bowen's disease.

Representative examples of cancers or tumors that may be targeted by the conjugate include, but are not limited to: lung cancer, colon cancer, prostate cancer, lymphoma, melanoma, breast cancer, ovarian cancer, testicular cancer, CNS cancer, renal cancer, kidney cancer, pancreatic cancer, stomach cancer, oral cancer, nasal cancer, cervical cancer, and leukemias. It will be readily apparent to the ordinarily skilled artisan that the particular cell binding agent used in the conjugate may be chosen such that it targets the drug to the tumor tissue to be treated with the drug (i.e., a targeting agent specific for a tumor-specific antigen is chosen). Examples of such targeting antibodies are well known in the art with non-limiting examples of: anti-Her2 for treatment of breast cancer, anti-CD20 for treatment of lymphoma, anti-PSMA for treatment of prostate cancer, and antiCD30 for treatment of lymphomas, including non-Hodgkin's lymphoma.

In an embodiment, the present invention provides a method of killing a cell. The method includes administering to the cell an amount of a conjugate of the invention sufficient to kill said cell. In an exemplary embodiment, the conjugate is administered to a subject bearing the cell. In a further exemplary embodiment, the administration serves to retard or stop the growth of a tumor that includes the cell (e.g., the cell can be a tumor cell).

For the administration to retard the growth, the rate of growth of the cell should be at least 10% less than the rate of growth before administration. Preferably, the rate of growth will be retarded at least 20%, 30%, 40%, 50%, 60%, 70%, 80%, 90%, or completely stopped.

Autoimmune diseases for which the drug conjugates may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, antiphospholipid antibody syndrome, and psoriatic arthritis), osteoarthritis, autoimmune gastrointestinal and liver disorders (such as, for example, inflannnatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteritis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). Diseases of particular interest may include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

The conjugates of the Invention may be useful for killing or inhibiting the multiplication of a cell that produces an infectious disease or for treating an infectious disease. The conjugates of the Invention may be used accordingly in a variety of settings for the treatment of an infectious disease in an animal. The conjugates may be used to deliver a drug to a target cell. Without being bound by theory, in one embodiment, the conjugate associates with an antigen on the surface of a target cell, and the conjugate is then taken up inside a target cell through receptor-mediated endocytosis. Once inside the cell, the payload drug may be released. The released drug is then free to migrate in the cytosol and induce cytotoxic activities. In an alternative embodiment, the drug is cleaved from the conjugate outside the target cell, and the drug subsequently penetrates the cell. In one embodiment, the conjugates kill or inhibit the multiplication of cells that produce a particular infectious disease. Particular types of infectious diseases that can be treated with the conjugates include, but are not limited to, Diptheria, Pertussis, Occult Bacteremia, Urinary Tract Infection, Gastroenteritis, Cellulitis, Epiglottitis, Tracheitis, Adenoid Hypertrophy, Retropharyngeal Abcess, Impetigo, Ecthyma, Pneumonia, Endocarditis, Septic Arthritis, Pneumococcal, Peritonitis, Bactermia, Meningitis, Acute Purulent Meningitis, Urethritis, Cervicitis, Proctitis, Pharyngitis, Salpingitis, Epididymitis, Gonorrhea, Syphilis, Listeriosis, Anthrax, Nocardiosis, *Salmonella*, Typhoid Fever, Dysentery, Conjuntivitis, Sinusitis, Brucellosis, Tullaremia, Cholera, Bubonic Plague, Tetanus, Necrotizing Enteritis, Actinomycosis, Mixed Anaerobic Infections, Syphilis, Relapsing Fever, Leptospirosis, Lyme Disease, Rat Bite Fever, Tuberculosis, Lymphadenitis, Leprosy, *Chlamydia, Chlamydia* Pneumonia, Trachoma, Inclusion Conjunctivitis, Systemic Fungal Diseases (Histoplarnosis, Coccicidiodomycosis, Blastomycosis, Sporotrichosis, Cryptococcsis, Systemic Candidiasis, Aspergillosis, Mucormycosis, Mycetoma, Chromomycosis), Rickettsial Diseases (Typhus, Rocky Mountain Spotted Fever, Ehrlichiosis, Eastern Tick-Borne Rickettsioses, Rickettsialpox, Q Fever, Bartonellosis), Parasitic Diseases (Malaria, Babesiosis, African Sleeping Sickness, Chagas' Disease, Leishmaniasis, Dum-Dum Fever, Toxoplasmosis, Meningoencephalitis, Keratitis, Entarnebiasis, Giardiasis. Cryptosporidiasis, Isosporiasis, Cyclosporiasis, Microsporidiosis, Ascariasis, Whipworm Infection, Hookworm Infection, Threadworm Infection, Ocular Larva Migrans, Trichinosis, Guinea Worm Disease, Lymphatic F ilariasis, Loiasis, River Blindness, Canine Heartworm Infection, Schistosomiasis, Swimmer's Itch, Oriental Lung Fluke, Oriental Liver Fluke, Fascioliasis, Fasciolopsiasis, Opisthorchiasis, Tapeworm Infections, Hydatid Disease, Alveolar Hydatid Disease), Viral Diseases (Measles, Subacute sclerosing panencephalitis, Common Cold, Mumps, Rubella, Roseola, Fifth Disease, Chickenpox, Respiratory syncytial virus infection, Croup, Bronchiolitis, Infectious Mononucleosis, Poliomyelitis, Herpangina, Hand-Foot-and-Mouth Disease, Bornholm Disease, Genital Herpes, Genital Warts, Aseptic Meningitis, Myocarditis, Pericarditis, Gastroenteritis, Acquired Immunodeficiency Syndrome (AIDS), Reye's Syndrome, Kawasaki Syndrome, Influenza, Bronchitis, Viral "Walking" Pneumonia, Acute Febrile Respiratory Disease, Acute pharyngoconjunctival fever, Epidemic keratoconjunctivitis, Herpes Simplex Virus 1 (HSV-1), Herpes Simples Virus 2 (HSV-2), Shingles, Cytomegalic Inclusion Disease, Rabies, Progressive Multifocal Leukoencephalopathy, Kuru, Fatal Familial Insomnia, Creutzfeldt-Jakob Disease, Gerstrnann-Straussler-Scheinker Disease, Tropical Spastic Paraparesis, Western Equine Encephalitis, California Encephalitis, St. Louis Encephalitis, Yellow Fever, Dengue, Lymphocytic choriomeningitis, Lassa Fever, Hemorrhagic Fever, Hantvirus Pulmonary Syndrome, Marburg Virus Infections, Ebola Virus Infections, and Smallpox).

Cell ablation uses include destroying or inhibiting: (1) cardiac pacemaker cells responsible for arrhythmias; (2) over-active neurons responsible for neurological disorders; and (3) hyperactive endocrine functions etc.

B. Dosages

Pharmaceutical compositions suitable for use with the present invention include compositions wherein the active ingredient is contained in a therapeutically effective amount, i.e., in an amount effective to achieve its intended purpose. The actual amount effective for a particular application will depend, inter alia, on the condition being treated, the severity and course of the disease, whether the molecule is administered for preventive or therapeutic purposes, previous therapy, the patient's clinical history and response, and the discretion of the attending physician. Determination of an effective amount is well within the capabilities of those skilled in the art, especially in light of the detailed disclosure herein.

For any compound described herein, the therapeutically effective amount can be initially determined from cell culture assays. Target plasma concentrations will be those concentrations of active compound(s) that are capable of inhibition cell growth or division. In preferred embodiments, the cellular activity is at least 25% inhibited. Target plasma concentrations of active compound(s) that are capable of inducing at least about 50%, 75%, or even 90% or higher inhibition of cellular activity are presently preferred. The percentage of inhibition of cellular activity in the patient can be monitored to assess the appropriateness of the plasma drug concentration achieved, and the dosage can be adjusted upwards or downwards to achieve the desired percentage of inhibition.

As is well known in the art, therapeutically effective amounts for use in humans can also be determined from animal models. For example, a dose for humans can be formulated to achieve a circulating concentration that has been found to be effective in animals. The dosage in humans can be adjusted by monitoring cellular inhibition and adjusting the dosage upwards or downwards, as described above.

A therapeutically effective dose can also be determined from human data for compounds which are known to exhibit similar pharmacological activities. The applied dose can be adjusted based on the relative bioavailability and potency of the administered compound as compared with the known compound.

Adjusting the dose to achieve maximal efficacy in humans based on the methods described above and other methods as are well-known in the art is well within the capabilities of the ordinarily skilled artisan.

In the case of local administration, the systemic circulating concentration of administered compound will not be of particular importance. In such instances, the compound is administered so as to achieve a concentration at the local area effective to achieve the intended result.

The molecule is suitably administered to the patient at one time or over a series of treatments. Depending on the type and severity of the disease, about 1 μg/kg to 15 mg/kg of molecule is an initial candidate dosage for administration to the patient, whether, for example, by one or more separate administrations, or by continuous infusion. A typical daily dosage might range from about 1 μg/kg to 100 mg/kg or more, depending on the factors mentioned above. An exemplary dosage of a conjugate to be administered to a patient is in the range of about 0.1 to about 10 mg/kg of patient weight. For repeated administrations over several days or longer, depending on the condition, the treatment is sustained until a desired suppression of disease symptoms occurs. An exemplary dosing regimen comprises a course of administering an initial loading dose of about 4 mg/kg, followed by additional doses every week, two weeks, or three weeks of a conjugate. Other dosage regimens may be useful. The progress of this therapy is easily monitored by conventional techniques and assays.

For other modes of administration, dosage amount and interval can be adjusted individually to provide plasma levels of the administered compound effective for the particular clinical indication being treated. For example, in one embodiment, a compound according to the invention can be administered in relatively high concentrations multiple times per day. Alternatively, it may be more desirable to administer a compound of the invention at minimal effective concentrations and to use a less frequent administration regimen. This will provide a therapeutic regimen that is commensurate with the severity of the individual's disease.

Utilizing the teachings provided herein, an effective therapeutic treatment regimen can be planned which does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

A compound of the invention may be administered alone or in combination with other treatments, either simultaneously or sequentially dependent upon the condition to be treated. Examples of treatments and therapies include, but are not limited to, chemotherapy (the administration of active agents, including, e.g. drugs, such as chemotherapeutics); immune therapy; surgery; and radiation therapy. A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Classes of immunooncology agents include PD-1 antagonists.

C. Methods of Evaluating Cellular Uptake

In some aspects, provided are methods for evaluating cellular uptake of an agent. The methods may comprise contacting a sample comprising a cell with a labeled agent as detailed herein and detecting light emission, whereby the detection of light emission indicates cellular uptake of the agent. The cellular uptake of the agent results in the reduction of the compound and the generation of a released reporter moiety.

(1) Fluorescent Reporter Moiety

In some embodiments, the reporter moiety may include a fluorescent reporter moiety. The fluorescent reporter moiety may include a fluorophore. Light emission is detected by exposing the sample to a wavelength of light and detecting the fluorescence generated by the released reported moiety. An increase in fluorescence or a change in fluorescence wavelength as compared to the fluorescence or fluorescence wavelength of a control sample indicates cellular uptake of the agent. The fluorophore may be conjugated in such a way as to quench its fluorescence to provide a fluorogenic or profluorescent probe that releases the payload as an unquenched fluorophore by way of its self-immolating property. The control sample may be sample medium only, without cells, a sample with cells but without experimental treatment, or a sample not contacted with labeled agent. Fluorescence may be detected inside or outside the cell. Non-reducible analogues of the disclosed quinone labeling moieties may be used as control labels.

(2) Bioluminescent Reporter Moiety

In some aspects, the reporter moiety may include a bioluminescent reporter moiety. The bioluminescent reporter moiety may include a prosubstrate for a luciferase. In some embodiments, the cell includes a luciferase. The luciferase may be expressed in the cell. Light emission is detected by detecting luminescence produced by the luciferase utilizing the released reporter moiety. The detection of any light emission may indicate the cellular uptake of the agent. Alternatively, luminescence of the sample may be compared to the luminescence of a control sample, wherein cellular uptake of the agent is indicated if the luminescence of the sample is higher than the luminescence of the control sample. The control sample may be a sample that is not contacted with a labeled agent or a cell type that is incompetent for uptake of the agent. Luminescence may be detected inside or outside the cell.

In some embodiments, the cell does not include or express a luciferase, and luciferase is added to the sample. Light emission is detected by detecting luminescence produced by the luciferase utilizing the released reporter moiety that may exit the cell or be present in a cell lysate. The detection of any light emission may indicate the cellular uptake of the agent. Alternatively, luminescence of the sample may be compared to the luminescence of a control sample, wherein cellular uptake of the agent is indicated if the luminescence of the sample is higher than the luminescence of the control sample. The control sample may be sample medium only, without cells, a sample with cells but without experimental treatment, a cell type incompetent for uptake of the agent or a sample not contacted with labeled agent. Luminescence may be detected inside or outside the cell. Non-reducible analogues of the disclosed quinone labeling moieties may be used as control labels.

(3) Sample

The labeled agents may be used with samples containing biological components. The sample may comprise cells, tissues, or organs in vitro or in vivo. The compounds are generally non-toxic to living cells and other biological components within the concentrations of use.

Cells may include eukaryotic cells, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof. The cells may not have been genetically modified via recombinant techniques (non-recombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a molecule to be detected by the methods of the invention, a moiety which alters the level or activity of the molecule to be detected, and/or a gene product unrelated to the molecule or moiety that alters the level or activity of the molecule. The cell may or may not express a luciferase.

(4) Contact

The labeled agents may be combined with the sample in a way that facilitates contact between the compound and the sample components of interest. Typically, the labeled agent or a solution containing the labeled agent is simply added to the sample.

The cell uptake levels for selected labeled agents can be monitored with/without treatments that permeabilize the plasma membrane, such as electroporation, shock treatments or high extracellular ATP. Alternatively, selected labeled agents can be physically inserted into cells, e.g., by pressure microinjection, scrape loading, patch clamp methods, or phagocytosis.

An additional detection reagent typically produces a detectable response due to the presence of a specific cell component, intracellular substance, or cellular condition, according to methods generally known in the art. When the additional detection reagent has, or yields a product with, spectral properties that differ from those of the subject labeled agents, multi-color applications are possible. This is particularly useful where the additional detection reagent is a dye or dye conjugate having spectral properties that are detectably distinct from those of the labeled agents.

In certain embodiments, washing steps are unnecessary when using the disclosed labeling reagents and labeled agents.

(5) Light Detection

The labeled agents are generally utilized by combining a labeled agent as described above with a sample of interest comprising a cell under conditions selected to yield a detectable optical response or light output. Typically, a specified characteristic of the sample is determined by comparing the optical response with a standard or expected response. The sample may be illuminated at a wavelength selected to elicit the optical response. Alternatively, the light emission from the sample may be measured in a reading device that can measure the light output (luminescence) generated by the luciferase and bioluminescent reporter moiety, e.g., using a luminometer or photomultiplier. The optical response or light output may also be measured over time, for example in the same reaction chamber for a period of seconds, minutes, hours, etc.

A detectable optical response means a change in, or occurrence of, an optical signal that is detectable either by observation or instrumentally. Typically, the detectable response is a change in fluorescence or luminescence such as a change in the intensity, excitation or emission wavelength distribution of fluorescence or luminescence, fluorescence or luminescence lifetime, fluorescence or luminescence polarization, or a combination thereof. The degree and/or location of the signal, compared with a standard or expected response, indicates whether, and to what degree, the sample possesses a given characteristic.

At any time after or during contact with the labeled agent, the sample is illuminated with a wavelength of light selected to give a detectable optical response and observed with a means for detecting the optical response. Equipment that is useful for illuminating the compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors.

The optical response or light output may be optionally detected by visual inspection or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

6. Kits

In another aspect, the present invention provides kits containing one or more of the compounds or compositions of the invention and directions for using the compound or composition. In an exemplary embodiment, the invention provides a kit for conjugating a linker arm of the invention or linker arm of the invention with a payload to another molecule. The kit includes the linker or linker plus payload, and directions for attaching the linker to a particular functional group. The kit may also include one or more of a cytotoxic drug, a targeting agent, a detectable label, pharmaceutical salts or buffers. The kit may also include a container and optionally one or more vial, test tube, flask, bottle, or syringe. Other formats for kits will be apparent to those of skill in the art and are within the scope of the present invention.

7. Chemical Synthesis

A. Preparation of Conjugation Reagents

Scheme 4

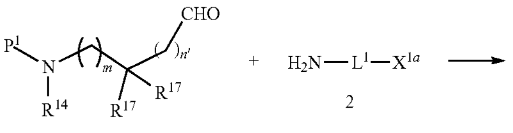

1

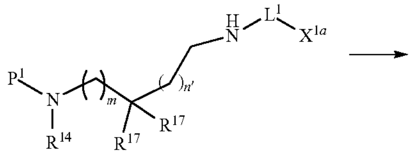

3

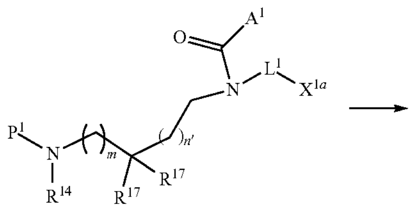

4

-continued

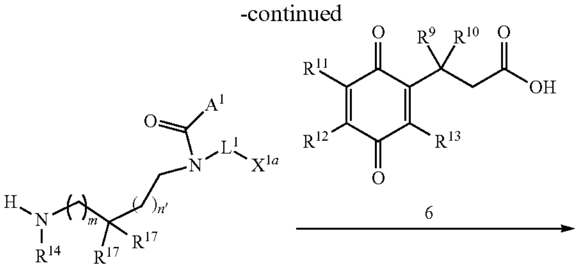

5

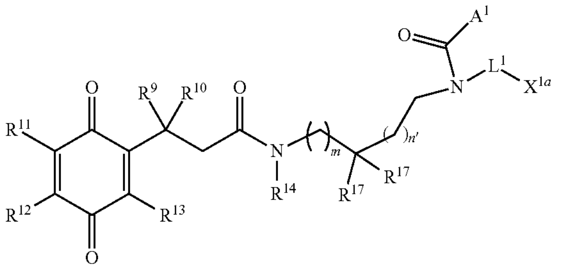

7

Conjugation reagents 7 may be prepared as generally illustrated in Scheme 4. Aldehydes 1, wherein $P^1$ is a nitrogen protecting group, may be subjected to a reductive amination reaction with amines 2 to provide amines 3. Typical reaction conditions include combining the reactants with a reducing agent (e.g., $NaBH_4$, $NaBH_3CN$, NaH$(OAc)_3$) in a solvent (e.g., ethanol, methanol, tetrahydrofuran, dichloroethane), optionally in the presence of a mild acid (e.g., acetic acid, ammonium hydroxide). Payload moieties $-A^1$ may be appended to amines 3 by reaction of a payload $HA^1$ with a suitable carbonate (e.g., bis(pentafluorophenyl) dicarbonate), chloroformate (e.g., 4-nitrophenyl chloroformate), phosgene, or triphosgene in an organic solvent (e.g., tetrahydrofuran) in the presence of a base (e.g., triethylamine or diisopropylethyl amine) to form an intermediate carbonate or carbonyl chloride (not shown) that may be reacted with amines 3 to provide carbamates 4. The protecting group $P^1$ may be removed using conditions well known in the art. For example, a tert-butoxycarbonyl (Boc) group may be removed with 50% of trifluoroacetic acid in the presence of triisopropyl silane or thioanisole in a solvent such as methylene chloride at room temperature for 30 minutes or longer to provide intermediates 5, which may be coupled with quinone carboxylic acid 6 under a variety of conditions. For example, quinone acid 6 may be converted to a mixed anhydride with a suitable chloroformate (e.g., isobutyl chloroformate) in the presence of a base (e.g., N-methylmorpholine) in a solvent (e.g., tetrahydrofuran) and the mixed anhydride reacted with 5 to provide 7. Alternatively, quinone acid 6 may be directly coupled to an amine linker by standard DCC coupling or DCC/HOBt conditions. Quinone acid 6 may also be activated by converting to acetyl chloride using oxalyl chloride or thionyl chloride, or converting to NHS ester using TSTU under basic conditions, or converting to a pentafluorobenzene ester.

Scheme 5

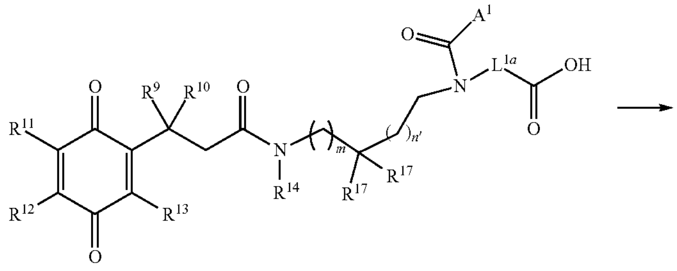

7.1

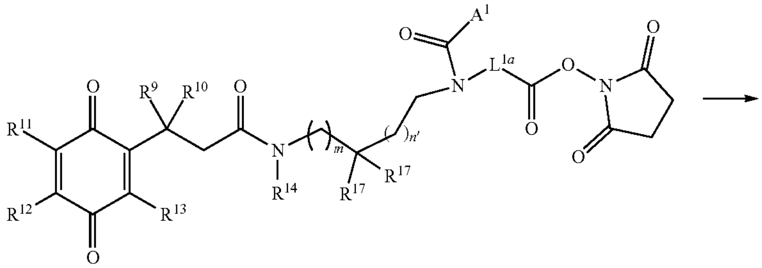

7.2

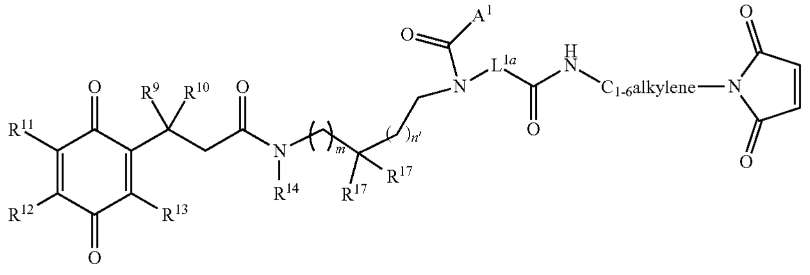

7.3

Certain compounds of formula 7 may be converted to other compounds of formula 7 by further functional manipulation of the $X^{1a}$ group. For example, compounds 7.1 wherein $X^{1a}$ is —COOH may be converted to compound 7.2, wherein $X^{1a}$ is

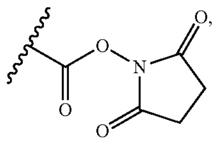 [SMILES: *C(=O)ON1C(=O)CCC1=O]

by reacting with TSTU under basic condition. Compound 7.2 may be further reacted with

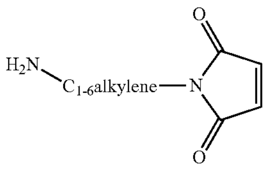

in the presence of a base (e.g., diispropylethylamine) in a solvent (e.g., dimethylformamide) to form compounds of formula 7.3, wherein $L^{1b}$ is —C(O)NR$^{20}$-$L^{1c}$-, $L^{1c}$ is $C_{1-6}$alkylene, and $X^{1a}$ is

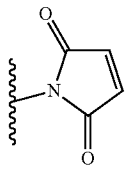 [SMILES: *N1C(=O)C=CC1=O]

(Scheme 5). Alternatively, the corresponding carboxylic acid 7.1 may be coupled with amines using standard amide bond forming conditions that are well known in the art (e.g., DCC and HOBt; DCC and DMAP).

Scheme 6

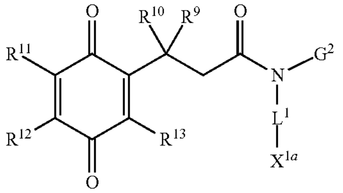

10

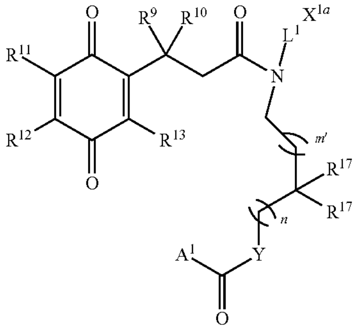

10 A

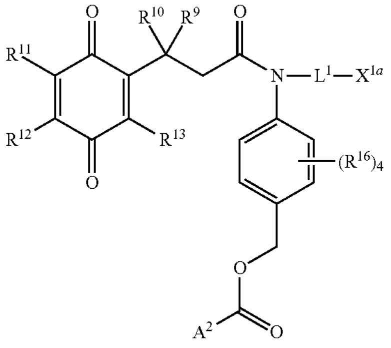

10B

Conjugation reagents include 10A family and 10B family (Scheme 6).

Scheme 7

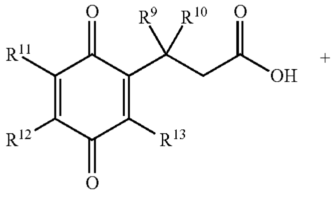

6

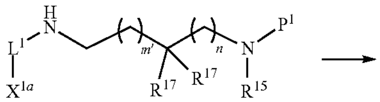

3a

-continued

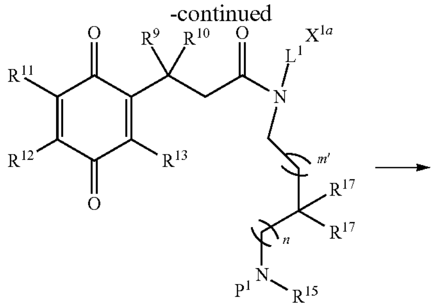

8a

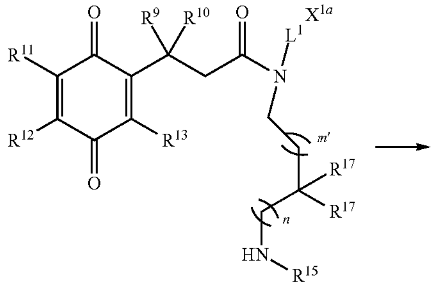

9a

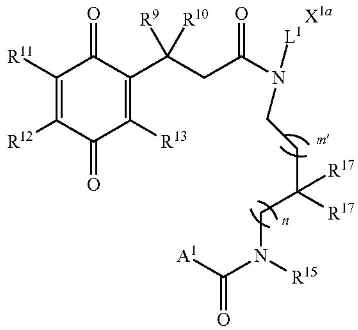

10C

Conjugation reagents 10C may be prepared by a general method illustrated in Scheme 7. Similarly, quinone acid 6 may be coupled to protected-diamine intermediate 3a by activating 6 with isobutyl chloroformate or acetyl chloride or other suitable standard coupling conditions to yield quinone amide 8a. Amine protecting group $P^1$, such as Boc, may be removed by TFA in the presence radical scavengers, such as triisopropyl silane or thioanisole to yield quinone diamine compound 9a. Payload $HA^1$ may be activated with a suitable carbonate or chloroformate (e.g., bis(pentafluorophenyl) dicarbonate, 4-nitrophenyl chloroformate), phosgene, or triphosgene in an organic solvent (e.g., tetrahydrofuran) in the presence of a base (e.g., triethylamine) to form an intermediate carbonate or carbonyl chloride (not shown) that may be reacted with amines 9a to provide carbamates 10C.

Scheme 8

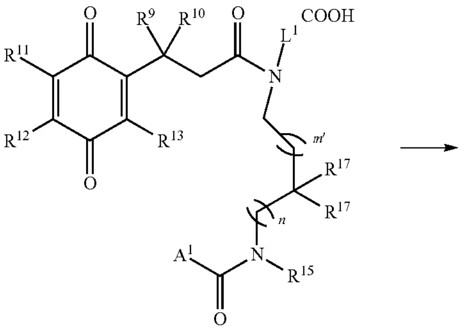

10A.1

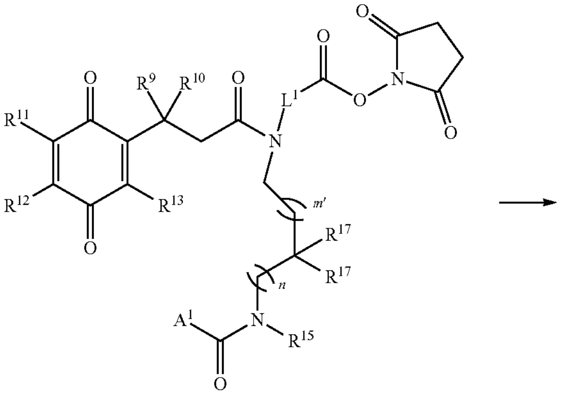

10A.2

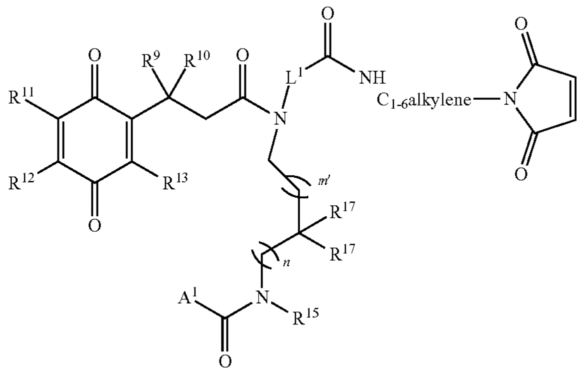

10A.3

Certain compounds of formula 10A may be converted to other compounds of formula 10A by further functional manipulation of the $X^{1a}$ group. For example, compounds 10A.1 wherein $X^{1a}$ is —COOH, may be converted to compound 10A.2, wherein $X^{1a}$ is

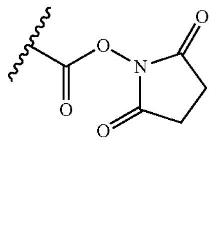 [SMILES: *C(=O)ON1C(=O)CCC1=O]

by reacting with TSTU under basic condition. Compound 10A.2 may be further reacted with

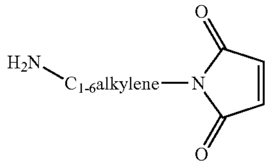

in the presence of a base (e.g., diispropylethylamine) in a solvent (e.g., dimethylformamide) to form compounds of formula 10A.3, wherein $L^{1b}$ is —C(O)$NR^{20}$-$L^{1c}$-, $L^{1c}$is $C_{1-6}$alkylene, and $X^{1a}$ is

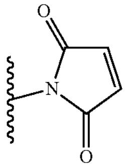 [SMILES: *N1C(=O)C=CC1=O]

(Scheme 8). Alternatively, the corresponding carboxylic acid 10A.1 may be coupled with amines using standard amide bond forming conditions that are well known in the art (e.g., DCC and HOBt; DCC and DMAP).

Scheme 9

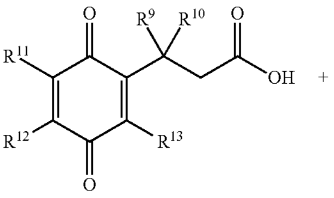

6

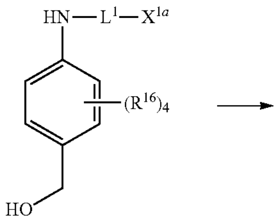

8b

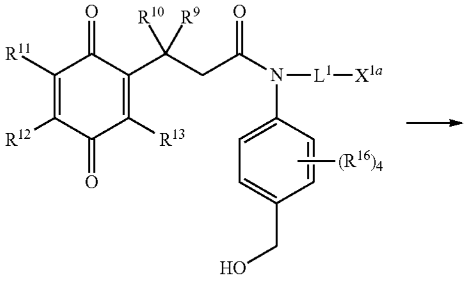

9b

-continued

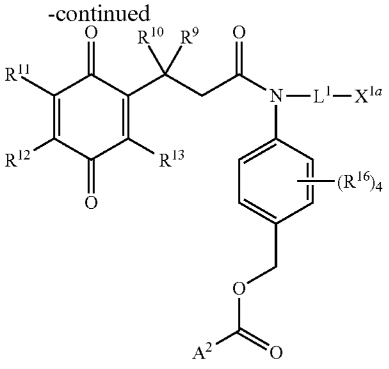

10B

Conjugation reagents 10B family may be prepared by a general method illustrated in Scheme 9. Quinone carboxylic acid 6 may be coupled to aminobenzyl alcohol 8b to generate compound 9b. which can be activated by triphosgene, isobutyl chloroformate, or bis(pentafluorobenzene) carbonate and further conjugated to payload $A^2$ moiety. Alternatively, payload $HA^2$ may be activated with a suitable carbonate or chloroformate (e.g., bis(pentafluorophenyl) dicarbonate, 4-nitrophenyl chloroformate), phosgene, or triphosgene in an organic solvent (e.g., tetrahydrofuran) in the presence of a base (e.g., triethylamine) to form an intermediate carbonate or carbonyl chloride (not shown) that may be reacted with alcohol 9b to provide carbamates 10B.

Scheme 10

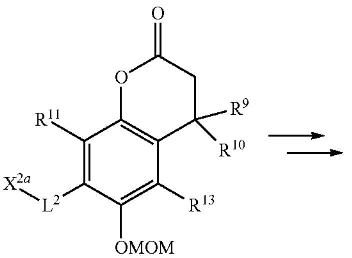

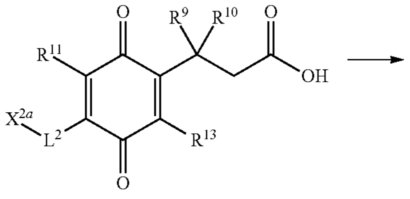

11

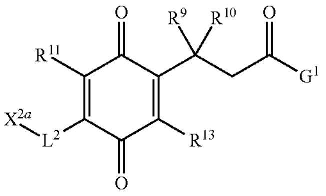

12

Conjugation reagents 12 may be prepared as generally illustrated in Scheme 10 and using chemistries disclosed by Zheng et al. in J. Org. Chem. (1999) 64 (1) 156-161 (e.g., Schemes 2-4). For example, a MOM-protected lactone may be transformed to quinone carboxylic acid 11 by oxidation with N-bromosuccinimide in an appropriate solvent (e.g., tetrahydrofuran and water).

Scheme 11

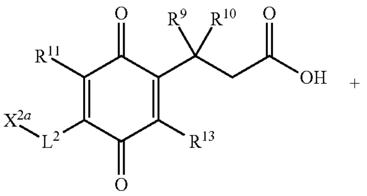

11

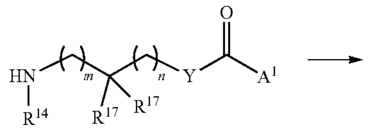

13

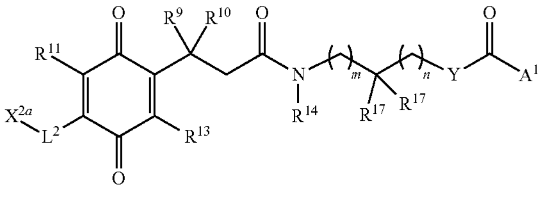

14

In the transformation of 11 to 12, $G^1$ as

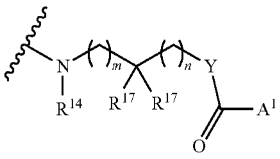

may be appended as shown generally in Scheme 11. Carboxylic acid 11 may be coupled with amine 13 using conditions analogous to those used to convert 5 to 7 in Scheme 4.

Scheme 12

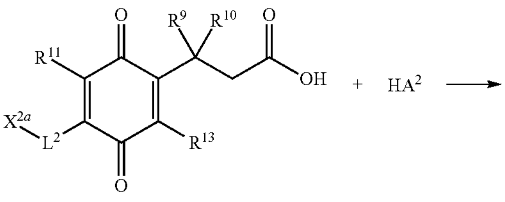

11

-continued

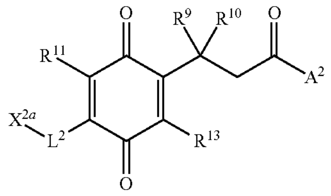

15

In the transformation of 11 to 12, $G^1$ as $-A^2$ may be appended as shown generally in Scheme 12. $HA^2$ may be reacted with 11 under standard amide coupling conditions for forming an amide, ester, or thioester, depending on whether $A^2$ is bonded through a nitrogen, oxygen, or sulfur atom.

Scheme 13

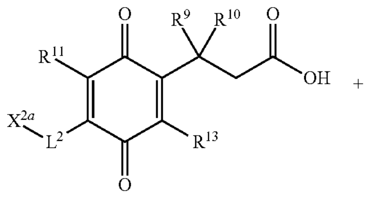

11

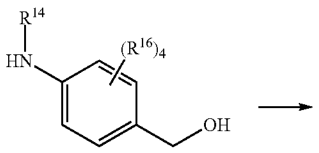

15

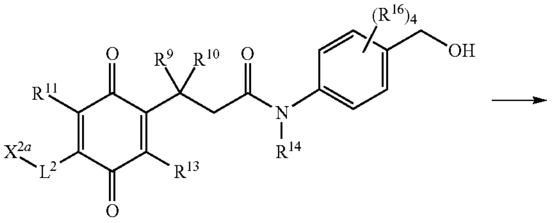

16

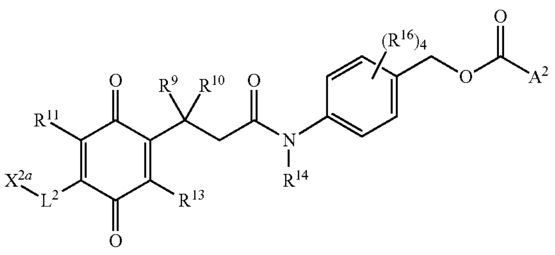

17

In the transformation of 11 to 12, $G^1$ as

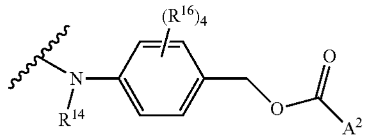

may be appended as shown generally in Scheme 13. Aniline 15 may be coupled with carboxylic acid 11 using standard amide bond forming conditions. Alcohol 16 may be converted to an activated carbonate (e.g., 4-nitrophenyl- or pentafluorophenyl-carbonate) or chloroformate and reacted with $HA^2$ under conditions analogous to those disclosed in US2008/0279868 to provide 17.

B. Preparation of Drug Conjugates

Typically, fewer than the theoretical maximum of drug moieties are conjugated to an antibody during a conjugation reaction. An antibody may contain, for example, many lysine residues that do not react with the drug-linker intermediate (D-L) or linker reagent. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups, which may be linked to a drug moiety. Most cysteine thiol residues in the antibodies of the compounds exist as disulfide bridges and must be reduced with a reducing agent such as dithiothreitol (DTT) or TCEP under partial or total reducing conditions. The loading (drug/antibody ratio) of an ADC may be controlled in several different manners, including: (i) limiting the molar excess of drug-linker intermediate or linker reagent relative to antibody, (ii) limiting the conjugation reaction time or temperature, and (iii) partial or limiting reductive conditions for cysteine thiol modification.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) maleimide groups (ii) activated disulfides, (iii) active esters such as NHS (N-hydroxysuccinimide) esters, HOBt (N-hydroxybenzotriazole) esters, haloformates, and acid halides; (iv) alkyl and benzyl halides such as haloacetamides; and (v) carboxyl.

Conjugation reagents may also be coupled with an engineered antibody using click chemistry such as the reaction between an alkyne and an azide. See Jain et al., Pharm. Res. (2015) 32: 3526-40, which is hereby incorporated by reference.

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

In general, to prepare conjugates of a partially reduced antibody having an average 2 drugs per antibody, the relevant antibody is reduced using a reducing agent such as dithiothreitol (DTT) or tricarbonyl ethylphosphine (TCEP) (about 1.8 equivalents) in PBS with 1 mM DTPA, adjusted to pH 8 with 50 mM borate. The solution is incubated at 37° C. for 1 hour, purified using a 50 mL G25 desalting column equilibrated in PBS/1 mM DTPA at 4° C. The thiol concentration, the protein concentration, and the ratio of thiol to antibody can be determined using procedures disclosed in U.S. Pat. No. 7,829,531. Conjugates having an average 4 drugs per antibody can be made using the same methodology, using about 4.2 equivalents of a suitable reducing agent to partially reduce the antibody.

The partially reduced antibody samples may be conjugated to a corresponding Drug-Linker compound using about 2.4 and about 4.6 molar equivalents of Drug-Linker compound per antibody to prepare the 2 and 4 drugs per antibody conjugates, respectively. The conjugation reactions may be incubated on ice for 1 hour, quenched with about 20-fold excess of cysteine to drug, and purified by elution over a G25 desalting 25 column at about 4° C. The resulting Drug-Linker-antibody conjugates may be concentrated to about 3 mg/mL, sterile filtered, aliquoted and stored frozen.

Alternatively, free thiol groups may be introduced into the antibody through reaction of lysines of the antibody with 2-iminothiolane. Initially, the antibody to be conjugated may be buffer exchanged into 0.1 M phosphate buffer pH 8.0 containing 50 mM NaCl, 2 mM DTPA, pH 8.0 and concentrated to 5-10 mg/mL. Thiolation may be achieved through addition of 2-iminothiolane to the antibody. The amount of 2-iminothiolane to be added is determined in preliminary experiments and varies from antibody to antibody. In the preliminary experiments, a titration of increasing amounts of 2-iminothiolane is added to the antibody, and following incubation with the antibody for one hour at room temperature, the antibody is desalted into 50 mM HEPES buffer pH 6.0 using a Sephadex G-25 column and the number of thiol groups introduced determined rapidly by reaction with dithiodipyridine (DTDP). Reaction of thiol groups with DTDP results in liberation of thiopyridine which is monitored at 324 nm. Samples at a protein concentration of 0.5-1.0 mg/ml may be used. The absorbance at 280 nm is used to accurately determine the concentration of protein in the samples, and then an aliquot of each sample (0.9 mL) is incubated with 0.1 mL DTDP (5 mM stock solution in ethanol) for 10 minutes at room temperature. Blank samples of buffer alone plus DTDP may also be incubated alongside. After 10 minutes, absorbance at 324 nm is measured and the number of thiols present quantitated using an extinction coefficient for thiopyridine of $19800M^{-1}$.

Typically, a thiolation level of three thiol groups per antibody is desired. For example, this may be achieved through adding a 15 fold molar excess of 2-iminothiolane followed by incubation at room temperature for 1 hour. Antibody to be conjugated is therefore incubated with 2-iminothiolane at the desired molar ratio and then desalted into conjugation buffer (50 mM HEPES buffer pH 6.0 containing 5 mM Glycine, 3% Glycerol and 2 mM DTPA). The thiolated material is maintained on ice whilst the number of thiols introduced is quantitated as described above.

After verification of the number of thiols introduced, the drug-linker molecule containing a reactive $X^{1a}/X^{2a}$ group may be added at a 3-fold molar excess per thiol. The conjugation reaction may be carried out in conjugation buffer also containing a final concentration of 5% ethylene glycol dimethyl ether (or a suitable alternative solvent). The drug-linker stock solution may be dissolved in 90% ethylene glycol dimethyl ether, 10% dimethyl sulfoxide. For addition to antibody, the stock solution may be added directly to the thiolated antibody, which has enough ethylene glycol dimethyl ether added to bring the final concentration to 5%, or pre-diluted in conjugation buffer containing a final concentration of 10% ethylene glycol dimethyl ether, followed by addition to an equal volume of thiolated antibody.

The conjugation reaction may be incubated at room temperature for 2 hours with mixing. Following incubation the reaction mix may be centrifuged at 14000 RPM for 15 minutes, and the pH adjusted to 7.2 if purification is not immediate. Purification of conjugate may be achieved through chromatography using a number of methods. Conjugate may be purified using size-exclusion chromatography on a Sephacryl S200 column pre-equilibrated with 50 mM HEPES buffer pH 7.2 containing 5 mM glycine, 50 mM NaCl and 3% glycerol. Chromatography may be carried out at a linear flow rate of 28 cm/h. Fractions containing conjugate are collected, pooled and concentrated. Alternatively, purification may be achieved through ion-exchange chromatography. Conditions vary from antibody to antibody and need to be optimized in each case. For example, antibody-drug conjugate reaction mix may be applied to an SP-Sepharose column pre-equilibrated in 50 mM HEPES, 5 mM Glycine, 3% glycerol, pH 6.0. The antibody conjugate may be eluted using a gradient of 0-1 M NaCl in equilibration buffer. Fractions containing the conjugate may be pooled, the pH adjusted to 7.2, and the sample concentrated as required.

To conjugate with amino groups of an antibody (e.g., lysine), a solution of an antibody in aqueous buffer may be incubated with a molar excess of a conjugation reagent bearing a reactive group $X^{1a}/X^{2}a$. The reaction mixture may be quenched by addition of excess amine (such as ethanolamine, taurine, etc.). The antibody drug conjugate may then be purified by gel filtration. The number of payload molecules bound per antibody molecule can be determined by measuring spectrophotometrically. An average of 1-10 payload molecules/antibody molecule may be linked by this method. In some embodiments, a preferred average number of linked payload molecules is 2-5. In other embodiments, a preferred average number of linked payload molecules is 3-4.5.

8. Examples

The foregoing may be better understood by reference to the following examples, which are presented for purposes of illustration and are not intended to limit the scope of the invention.

Example 1

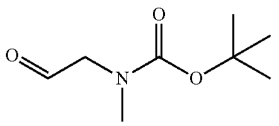

+

-continued

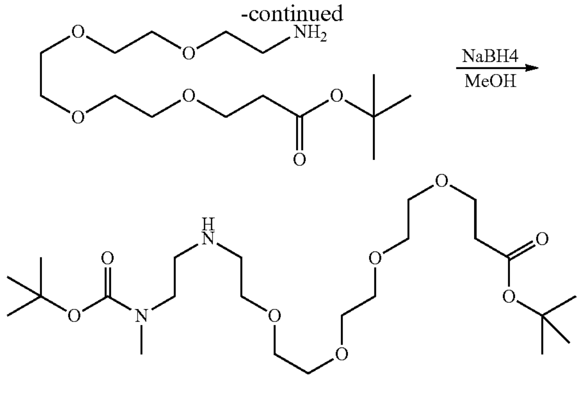

Synthesis of N-[(PEG)$_4$-COO-t-Bu]-N'—Boc-N'-methyl-ethylenediamine

To a solution of N-t-BuOOC-(PEG)$_4$-amine (0.557 g, 1.73 mmol) in 20 mL of methanol, (N-methyl)-N-Boc acetaldehyde (0.3 g, 1.73 mmol) was added. The mixture was stirred at room temperature for 3 hours. $NaBH_4$ (0.196 g, 5.2 mmol) was added to the mixture at 0° C., and the resultant mixture was stirred at 0° C. for 1 hour and then 1 hour at room temperature. The reaction was quenched by adding 5 mL of water. After removal of solvent, 5 mL of water was added, and the mixture was extracted three times with methylene chloride. The combined organic layer was dried over $Na_2SO_4$, and the product was purified by flash silica chromatography using heptane/ethyl acetate to methylene chloride/methanol to give a yield of 64.5% (0.535 g). $^1$H NMR (300 MHz, $CD_2Cl_2$) δ ppm: 3.5-3.8 (m, 18H, $CH_2$), 3.45 (br, 2H, $CH_2$), 2.98 (br, 2H, $CH_2$), 2.83 (s, 3H, $NCH_3$), 2.46 (t, 2H, $COCH_2$), 1.42 (s, 18H, $CH_3$); MS-ESI (m/e): 479.6 [M+H].

Using analogous procedures, the following intermediate amines were likewise prepared from appropriate starting materials.

TABLE 2

| | |
|---|---|
| 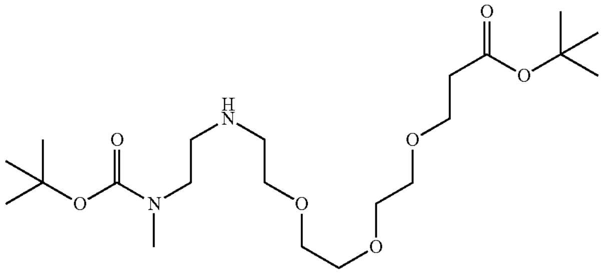 | $^1$H NMR (300 MHz, $CD_2Cl_2$) δ ppm: 3.68 (t, 2H, $OCH_2$), 3.56-3.60 (br, 10H, $CH_2$), 3.53 (t, 2H, $OCH_2$), 3.29 (t, 2H, CH2), 2.85 (s, 3H, $NCH_3$), 2.7-2.8 (m, 4H, NCH2), 2.47 (t, 2H, $COCH_2$), 1.44 (s, 18H, $CH_3$); MS-ESI (m/e): 435.5 [M + H]. |
| 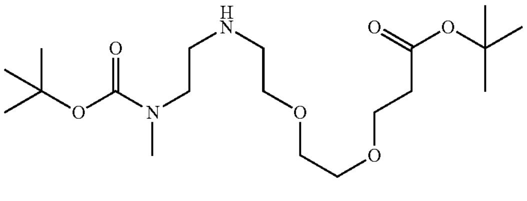 | $^1$H NMR (300 MHz, $CD_2Cl_2$) δ ppm: 3.67 (t, 2H, $OCH_2$), 3.56-3.60 (br, 6H, $OCH_2$), 3.29 (t, 2H, $CH_2$), 2.85 (s, 3H, $NCH_3$), 2.7-2.8 (m, 4H, NCH2), 2.46 (t, 2H, $COCH_2$), 1.45 (s, 18H, $CH_3$); MS-ESI (m/e): 391.4 [M + H]. |
| 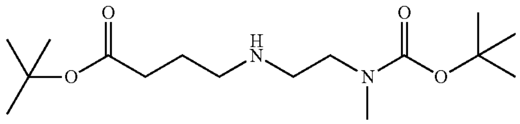 | MS (m/e) ($C_{16}H_{32}N_2O_4$), 317.4[M + H]. |
| 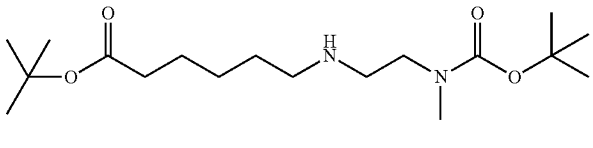 | $^1$H NMR (300 MHz, $CD_2Cl_2$) δ 3.25-3.30 (t, J = 9, 2H), 2.83 (s, 3H), 2.69-2.73 (t, J = 6, 2H), 2.56-2.61 (t, J = 9, 2H), 2.16-2.21 (t, J = 6, 2H), 1.46-1.61 (m, 4H), 1.42 (s, 18 H), 1.26-1.38 (m, 2H). MS (m/e) [M + H] ($C_{18}H_{37}N_2O_4$) calculated 345.5, observed 345.4. |

Example 2 (Prophetic Example)
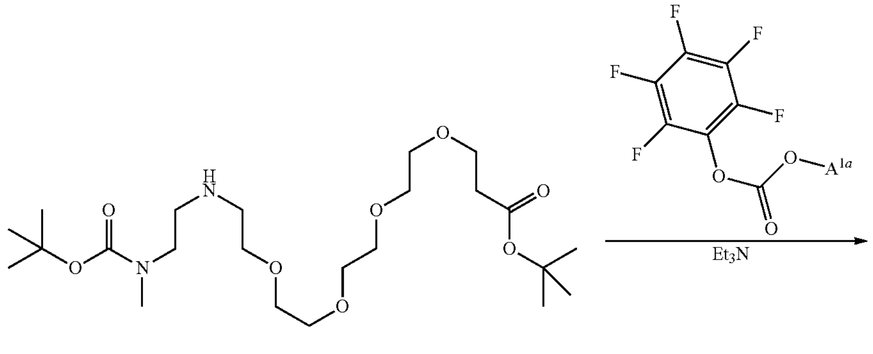
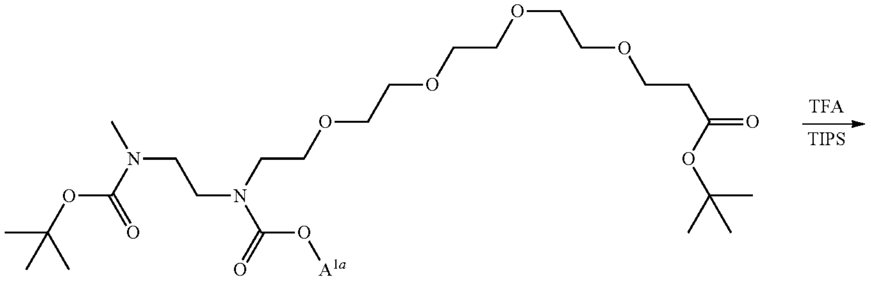
20
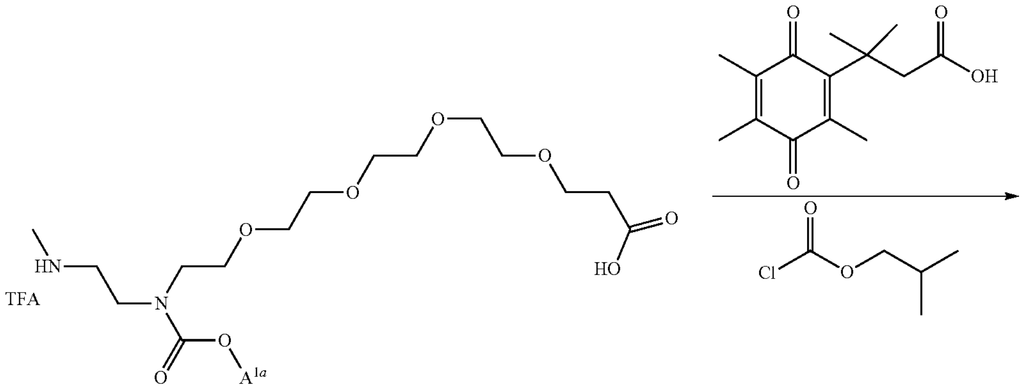
21

-continued

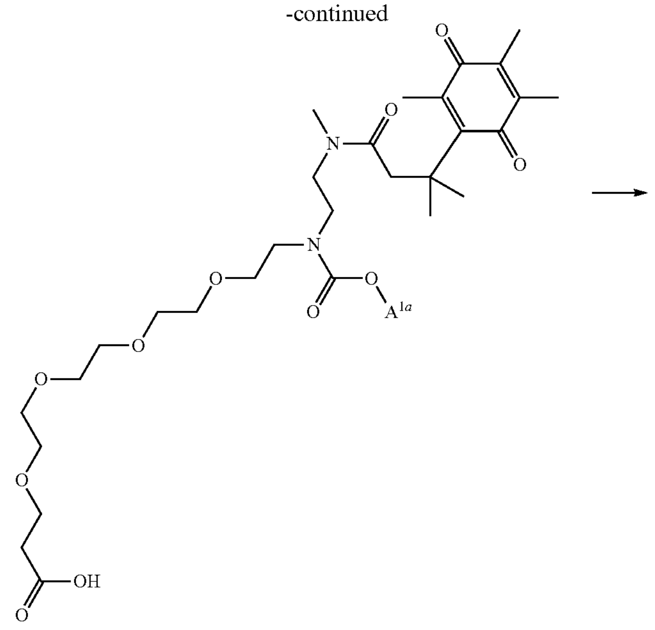

22

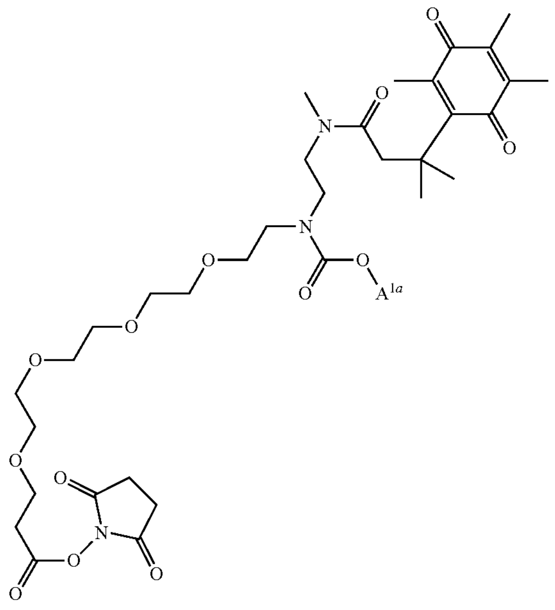

23

Synthesis of N-[(PEG)$_4$COO-t-Bu]-N'—Boc-N'-methyl-ethylene-diamine payload carbamate 20 (Prophetic Example)

To a mixture of a payload molecule HO-A$^{1a}$ (0.526 mmol) and bis(pentafluorophenyl) dicarbonate (0.276 g, 0.630 mmol) in 10 mL of dry tetrahydrofuran, triethylamine (0.106 mg, 1.05 mmol) may be added at room temperature under argon. The mixture may be stirred for 2-3 minutes, and N-[(PEG)$_4$COO-t-Bu]-N'—Boc-N'-methyl-ethylene diamine (0.553 mg, 1.16 mmol) added. The mixture may be stirred at room temperature for 30 minutes, and the product purified.

Synthesis of N-[(PEG)$_4$COOH]—(N'-methyl)-ethylenediamine payload carbamate 21 (Prophetic Example)

N-[(PEG)$_4$COO-t-Bu]-N'—Boc-N-methyl-ethylenediamine payload carbamate (0.136 mmol) and triisopropylsilane (50 μL) may be dissolved in 10 mL of methylene chloride and trifluoroacetic acid (1:1 in volume), and the mixture stirred at room temperature for 2 hours. After removal of the solvent, the residue may be dried under high vacuum overnight.

Synthesis of 22 (Prophetic Example)

To a solution of 3-methyl-3-(2,4,5-trimethyl-3,6-dioxocyclohexa-1,4-dien-1-yl)butanoic acid (107 mg, 0.428 mmol)

and isobutyl chloroformate (58.4 mg, 0.427 mmol) in 10 mL dry tetrahydrofuran, N-methyl morpholine (86.5 mg, 0.855 mmol) may be added at 0° C. The resultant mixture may be stirred 30 minutes at 0° C., and N'-methyl-N-[(PEG)$_4$COOH]ethylene-diamine] payload carbamate 21 in 5 mL of $CH_2Cl$ added, and the mixture stirred for 1 hour. The product may be directly purified with flash silica column chromatography.

Synthesis of 23 (Prophetic Example)

To a solution of 22 (0.314 mmol) and N,N,N',N'-Tetramethyl-O—(N-succinimidyl)uronium tetrafluoroborate (1.57 mmol) in 20 mL acetonitrile and methylene chloride (1:1), diisopropylethylamine (325 mg, 2.51 mmol) may be added at room temperature. The mixture may be stirred for 30 minutes. 120 mL of methylene chloride may be added, and the resultant mixture washed with citric acid (30%) solution and water. The organic layer may be dried over $Na_2SO_4$ and purified.

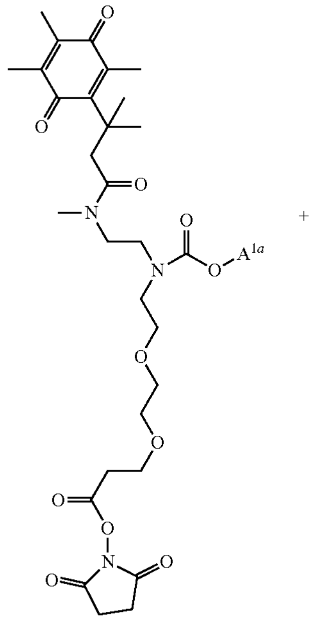

24

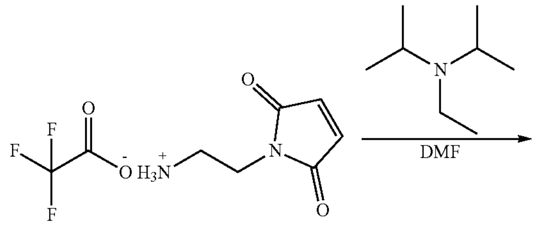

-continued

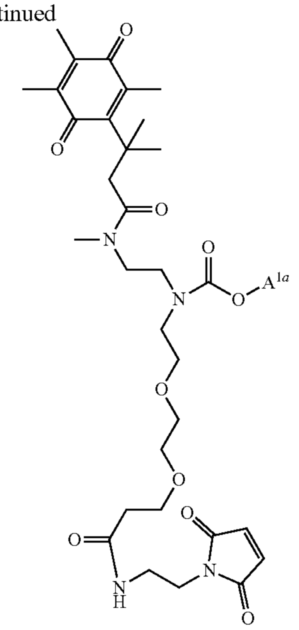

25

Synthesis of 25 (Prophetic Example)

Approximately 100 mg (392 μmol, 2 equiv.) of 1-(2-aminoethyl)-1H-pyrrole-2,5-dione TFA salt may be added to a vial together with 2 mL DMF and 196 μmol (1 equiv.) of the respective NHS ester 24 dissolved in 1 mL DMF. 70 μL diisopropylethylamine (392 μmol, 2 equiv.) may be added and then stirred at room temperature for over an hour. The reaction mixture may be dried down, and then purified by flash column chromatography.

Example 3

Antibody Drug Conjugate (Prophetic Lysine Conjugation Example)

To demonstrate conjugation of an antibody with the conjugation reagents of the present invention, the monoclonal antibody, Herceptin, may be labeled with 24. Lyophilized Herceptin may be dissolved in 0.1 M Sodium Bicarbonate, pH 8.6 at 10 mg/mL, and then diluted to 1 mg/mL in 100 μL of the same buffer. A 50 mM stock of 24 may be prepared in 100% DMSO. For labeling of the antibody, 24 may be added to 100 μL of diluted Herceptin (0.66 nmol). The sample may then be covered in foil and incubated for 60 minutes at room temperature on a tube rotator. To remove free 24, 100 μL of the labeling reaction may be placed onto an equilibrated G-25 Sequencing MicroSpin Column (Amersham, 200 μL resin) and eluted by spinning for 30 seconds at 3000 rpm. The conjugated Herceptin may be contained in the flow-through. Conjugation efficiency may be determined by spectrophotometry by taking the absorbance of the Herceptin-24 at 280 nm and 320 nm. The degree of labeling may be 2.3 molecules of 24 per one Herceptin antibody molecule.

Example 4

Antibody Drug Conjugate (Prophetic Lysine Conjugation Example)

A solution of huN901 antibody (2.5 mg/mL) in aqueous buffer (50 mM potassium phosphate, 50 mM sodium chloride, 2 mM ethylenediaminetetraacetic acid disodium salt), pH 6.5, may be incubated with a 6-fold molar excess of conjugation reagent (e.g., 24) in dimethylacetamide (DMA) to give a final DMA concentration of 20%. The reaction may be allowed to proceed for 13 hours at ambient temperature. The reaction mixture may be split into two portions. One portion may be purified by passage over a Sephadex G25 gel filtration column, and the second portion purified over a Sephacryl S300 gel filtration column. In each case the fractions containing monomeric conjugate may be pooled. The concentration of the conjugate may be determined spectrophotometrically. Purification by Sephadex G25 chromatography may give a conjugate containing, on the average, 2.08 payload molecules linked per antibody molecule. Purification by Sephacryl S300 chromatography may give a conjugate containing, on the average, 1.61 payload molecules linked per antibody molecule.

Example 5

Antibody Drug Conjugate (Prophetic Thiol Conjugation Example)

A solution of PBS/diethylenetriaminepentaacetic acid (2.2 mL) may be added to 4.2 mL of reduced antibody and the resulting solution cooled to 0° C. using an ice bath. In a separate flask, a stock DMSO solution of conjugation reagent (e.g., 25) (8.5 mol conjugation reagent per mol reduced antibody) may be diluted with MeCN. The MeCN solution of conjugation reagent may be rapidly added to the antibody solution, and the reaction mixture stirred using a vortex instrument for 5-10 seconds, returned to the ice bath, and allowed to stir at 0° C. for 1 hour, after which time 218 μL of a cysteine solution (100 mM in PBS/DTPA) may be added to quench the reaction. 60 μL of the quenched reaction mixture may be saved as a "qrm" sample. While the reaction proceeds, three PD10 columns (Sephadex G25, available from Sigma-Aldrich, St. Louis, Mo.) may be placed in a cold room and equilibrated with PBS (which had been pre-cooled to 0° C. using an ice bath). The quenched reaction mixture, which contained the conjugate, may be concentrated to −3 mL by ultracentrifugation using two Ultrafree 4 centrifuge filtering devices (30K molecular weight cutoff membrane; Millipore Corp.; Bedford, Mass.; used according to manufacturer's instructions), which may be pre-cooled to 4° C. in a refrigerator, and the concentrated reaction mixture eluted through the pre-chilled PD 10 columns using PBS as the eluent (1 mL for each column). The eluted conjugate may be collected in a volume of 1.4 mL per column for a total eluted volume of 4.2 mL. The eluted conjugate solution may then be filtered using a sterile 0.2 micron syringe-end filter, 250 μL of conjugate solution set aside for analysis, and the remainder of the conjugate solution frozen in sterile vials. The concentration of conjugate, the number of drug molecules per antibody, the amount of quenched drug-linker and the percent of aggregates may be determined using procedures disclosed in U.S. Pat. No. 7,829,531.

Example 6

Antibody Drug Conjugate (Prophetic Thiol Conjugation Example)

The conjugation method described herein is based on introduction of free thiol groups to the antibody through reaction of lysines of the antibody with 2-iminothiolane followed by reaction of the drug-linker molecule with an active maleimide group. Initially the antibody to be conjugated may be buffer exchanged into 0.1 M phosphate buffer pH 8.0 containing 50 mM NaCl, 2 mM DTPA, pH 8.0 and concentrated to 5-10 mg/ml. Thiolation may be achieved through addition of 2-iminothiolane to the antibody. The amount of 2-iminothiolane to be added may be determined in preliminary experiments and varies from antibody to antibody. In the preliminary experiments, a titration of increasing amounts of 2-iminothiolane may be added to the antibody, and following incubation with the antibody for one hour at room temperature, the antibody may be desalted into 50 mM HEPES buffer pH 6.0 using a Sephadex G-25 column, and the number of thiol groups introduced determined rapidly by reaction with dithiodipyridine (DTDP). Reaction of thiol groups with DTDP results in liberation of thiopyridine, which is monitored at 324 nm. Samples at a protein concentration of 0.5-1.0 mg/ml may be used. The absorbance at 280 nm may be used to accurately determine the concentration of protein in the samples, and then an aliquot of each sample (0.9 ml) may be incubated with 0.1 ml DTDP (5 mM stock solution in ethanol) for 10 minutes at room temperature. Blank samples of buffer alone plus DTDP may also be incubated alongside. After 10 minutes, absorbance at 324 nm may be measured and the number of thiols present quantitated using an extinction coefficient for thiopyridine of $19800M^{-1}$.

Typically, a thiolation level of three thiol groups per antibody is desired. For example, this may be achieved through adding a 15 fold molar excess of 2-iminothiolane followed by incubation at room temperature for 1 hour. Antibody to be conjugated may therefore be incubated with 2-iminothiolane at the desired molar ratio and then desalted into conjugation buffer (50 mM HEPES buffer pH 6.0 containing 5 mM Glycine, 3% Glycerol and 2 mM DTPA). The thiolated material may be maintained on ice whilst the number of thiols introduced is quantitated as described above.

After verification of the number of thiols introduced, the drug-linker molecule containing an active maleimide group may be added at a 3-fold molar excess per thiol. The conjugation reaction may be carried out in conjugation buffer also containing a final concentration of 5% ethylene glycol dimethyl ether (or a suitable alternative solvent). The drug-linker stock solution may be dissolved in 90% ethylene glycol dimethyl ether, 10% dimethyl sulfoxide. For addition to antibody, the stock solution may be added directly to the thiolated antibody, which has enough ethylene glycol dimethyl ether added to bring the final concentration to 5%, or pre-diluted in conjugation buffer containing a final concentration of 10% ethylene glycol dimethyl ether, followed by addition to an equal volume of thiolated antibody.

The conjugation reaction may be incubated at room temperature for 2 hours with mixing. Following incubation the reaction mix may be centrifuged at 14000 RPM for 15 minutes, and the pH adjusted to 7.2 if purification is not immediate. Purification of conjugate may be achieved through chromatography using a number of methods. Conjugate may be purified using size-exclusion chromatography on a Sephacryl S200 column pre-equilibrated with 50 mM HEPES buffer pH 7.2 containing 5 mM glycine, 50 mM NaCl and 3% glycerol. Chromatography may be carried out at a linear flow rate of 28 cm/h. Fractions containing conjugate may be collected, pooled, and concentrated. Alternatively, purification may be achieved through ion-exchange chromatography. Conditions may vary from antibody to antibody and need to be optimized in each case. For example, antibody-drug conjugate reaction mix may be applied to an SP-Sepharose column pre-equilibrated in 50 mM HEPES, 5 mM Glycine, 3% glycerol, pH 6.0. The antibody conjugate may be eluted using a gradient of 0-1M NaCl in equilibration buffer. Fractions containing the conjugate may be pooled, the pH was adjusted to 7.2 and the sample concentrated as required.

Example 7

Cellular Release of Luciferin from Herceptin Conjugates of PBI-5508 and PBI-6855

PBI 5508

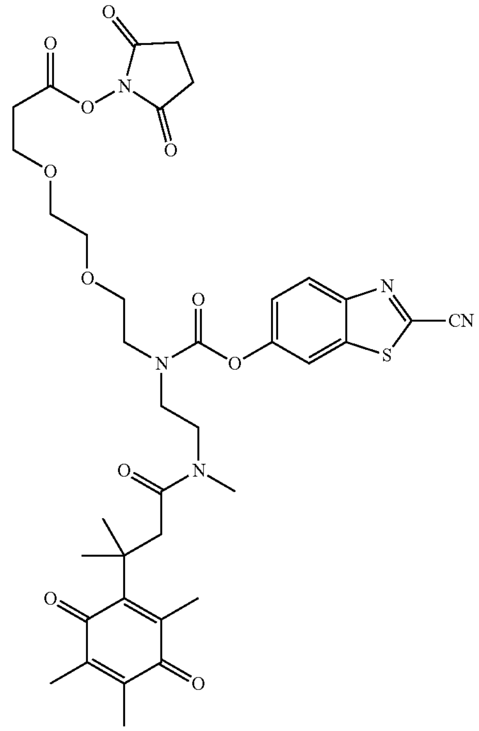

-continued

PBI 6855

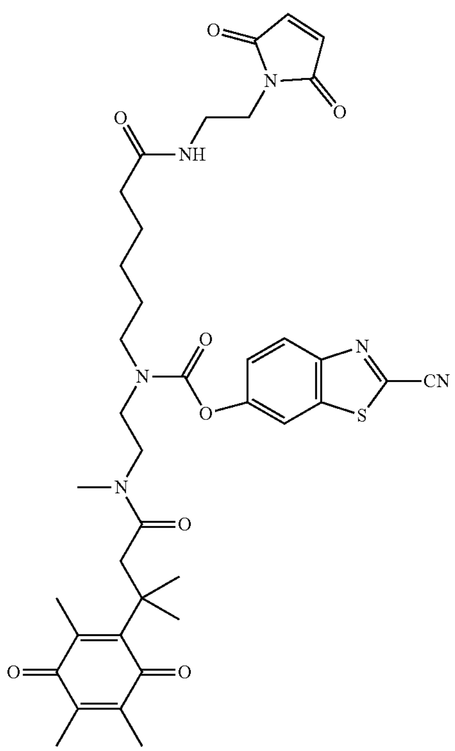

Herceptin conjugates of PBI-5508 (lysine conjugate) and PBI-6855 (thiol conjugate), prepared and conjugated to Herceptin using general methods described herein or in WO2015/116867, displayed the following characteristics:

| ADC Information | |
|---|---|
| ADC Name | Herceptin-5508-01 |
| Lot # | N/A |
| Yield | 68% |
| Total quantity (mg) | 16.24 |
| Concentration (mg/mL) | 2.90 |
| Volume (ml) | 5.50 |
| DAR | ~5 |
| HIC-HPLC | 3.60% |
| SEC-HPLC | 4.20% |
| RP-HPLC | n/a |
| Endotoxin (EU/mg) | n/a |
| ICE | n/a |
| ADC Name | Herceptin-6855 |
| Lot # | N/A |
| Yield | 50% |
| Total quantity (mg) | 12.60 |
| Concentration (mg/mL) | 3.70 |
| Volume (ml) | 3.40 |
| DAR | ~4 |
| HIC-HPLC | 4.40% |
| SEC-HPLC | 18.40% |
| RP-HPLC | n/a |
| Endotoxin (EU/mg) | n/a |
| ICE | n/a |

HIC-HPLC indicates the % of unconjugated antibody
SEC-HPLC indicates the % of high molecular weight aggregation The cyanobenzothiazole moiety of Herceptin conjugated PBI-5508 and PBI-6855 is converted to a D-luciferin moiety by incubation with D-cysteine. Conditions that release the D-luciferin moiety produce free D-luciferin that can be detected with a luciferin detection reagent that minimally contains ATP, Mg2+, and luciferase that produces light in proportion to the amount of free D-luciferin.

Figure 2:
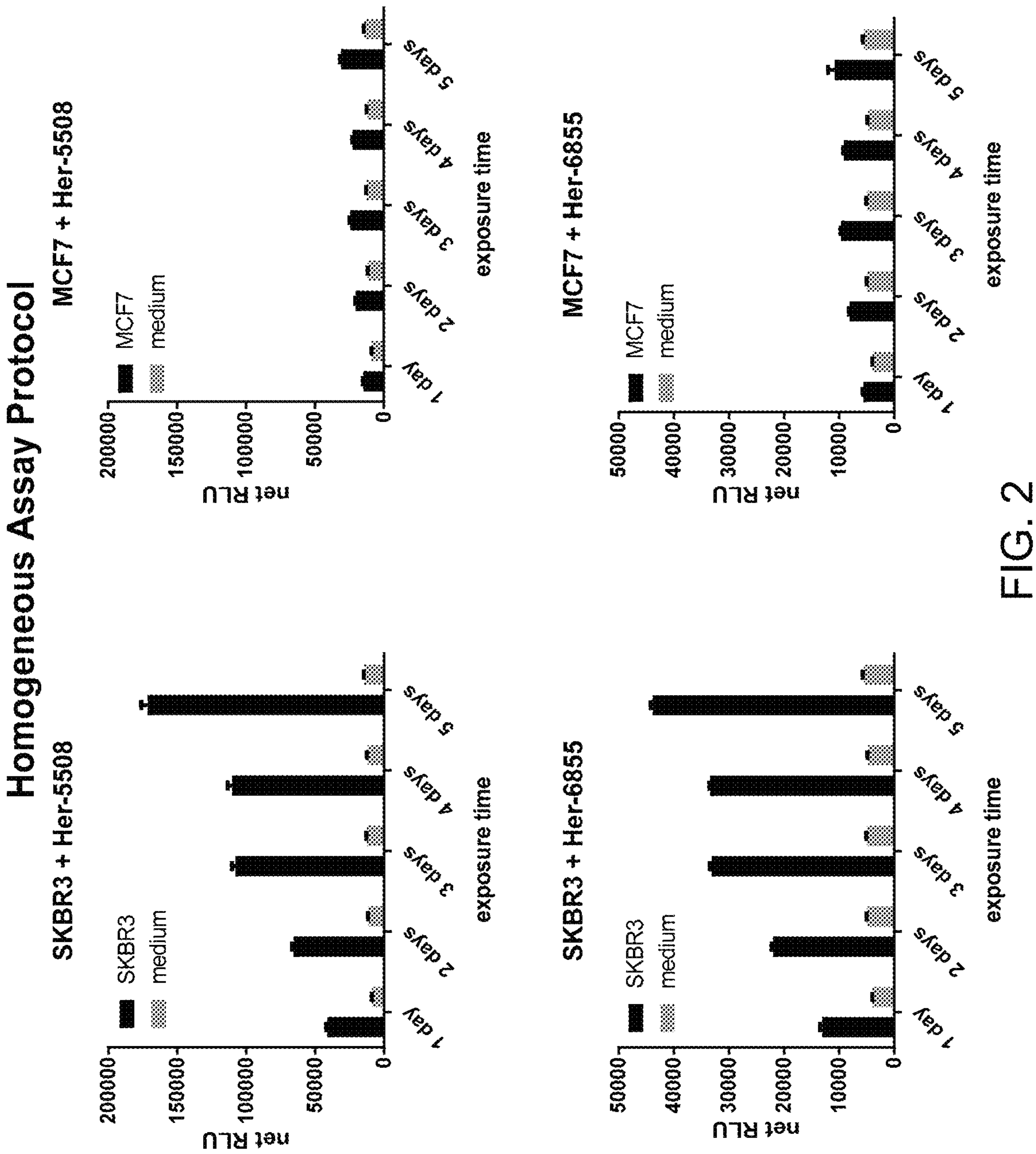
FIG. 2 shows luciferin luminescence upon cellular release of luciferin from the Herceptin Conjugate of PBI-5508 or PBI-6855 in HER positive and negative cells (Example 7).

Luciferin was released from the Herceptin conjugates upon exposure to cultured cells, consistent with the proposed mechanism of cellular uptake followed by release in the reducing environment inside of cells (FIGS. 1 and 2). The results in FIGS. 1 and 2 were obtained following incubations with SKBR2 cells or MCF7 cells. SKBR3 are known as HER2 positive cells because they express human epidermal growth factor receptor 2 (HER2) on the outer surface of their plasma membranes. MCF7 cells are HER2 negative cells because they do not express HER2. The Herceptin antibody binds to HER2 so the Herceptin luciferin-conjugates are expected to bind to and be internalized by the HER positive SKBR3 cells but not by HER2 negative MCF7 cells. FIGS. 1 and 2 show that in the presence of Her2 positive SKBR3 cells both conjugates released luciferin such that it accumulated over time. In contrast, medium alone and Her2 negative MCF7 cells released little or no luciferin from the conjugates.

Herceptin-5508 or Herceptin-6855 was incubated with the HER2 positive cell line SKB3 or with the HER2 negative cell line MCF7 for 1, 2, 3, 4, or 5 days. 10,000 cells per well were initially plated in a 96 well plate in 50 μL of McCoys medium and 1 hour later the conjugates were added to a concentration of 30 nM each. At each time point shown, the medium was removed to a second plate with an equal volume of a lytic luciferin detection reagent containing ATP and UltraGlo® luciferase (Promega Corporation), and luminescence was read on a plate reading luminometer (medium transfer assay protocol, FIG. 1). In this case, luciferin released inside of cells is detected after it diffuses into the medium. The detection reagent was also added to the cells remaining in the original plate, and luminescence was read on a plate reading luminometer (homogeneous assay protocol, FIG. 2). In this case, luciferin that remains associated with the cells is detected in the cell lysate. Parallel incubations in McCoys medium with no cells were also performed and luminescence from those wells was measured according to the medium transfer and the homogeneous protocols. An additional set of parallel measurements were taken from wells with medium but without conjugates added, and those background values were subtracted from the conjugate values to give net luminescence.

Example 8

Non-Cellular Release of Luciferin from Herceptin Conjugates of PBI-5508

Using a luciferin moiety as a probe payload on antibodies and on one protein that is not an antibody (bovine serum albumin), it was unexpectedly found that conjugation to a protein stabilizes TMQ-linked payload against non-cell mediated release by a reductive mechanism. This property may provide an additional advantage in ADCs where it is critical that payload is not released outside of target cells. The observations are as follows. When D-luciferin is derivatized on the 6' hydroxyl by addition of the TMQ linker, its activity as a substrate for luciferase is blocked (PBI-4312), but free D-luciferin that is fully active with luciferase is readily released

PBI 4312

Figure 3:
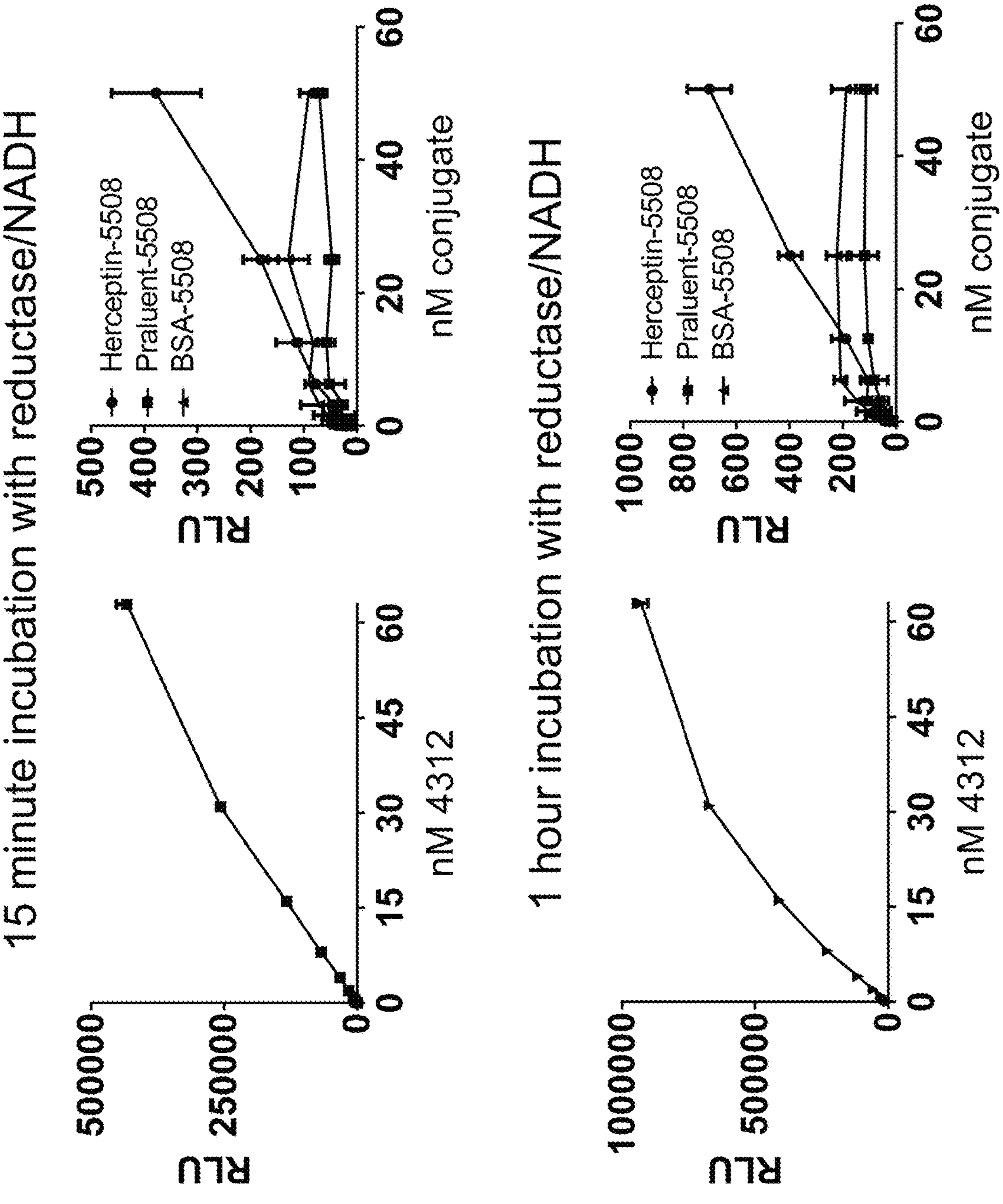
FIG. 3 shows luciferin luminescence upon non-cellular release of luciferin from PBI-4312, and Herceptin, BSA, and Praluent conjugates of PBI-5508 (Example 8).

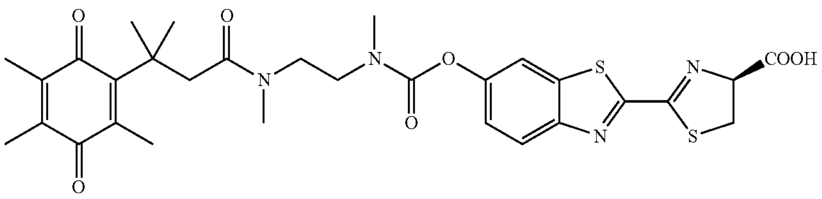

from a luciferin-TMQ derivative when subjected to reducing conditions inside or outside of a cell. However, release of D-luciferin from a protein-TMQ-luciferin conjugate by an extracellular reductive mechanism was substantially diminished compared to luciferin-TMQ. In other words, the protein moiety of the conjugate stabilizes the luciferin payload against reductive release from the TMQ linker in a non-cellular environment. Non-cellular reducing conditions include an aqueous reducing agent solution (e.g. DTT) or a reductase reaction mixture (FIG. 3). This was true for two conjugates with a luciferin payload as well as a luciferin-TMQ conjugate with bovine serum albumin (BSA). Whereas the reaction conditions produced substantial amounts of light with PBI-4312 (>900,000 RLU after 1 hour), only minimal signals were produced from similar amounts of the protein conjugates (<800 RLUs after 1 hour).

Bovine serum albumin, Praluent (an antibody drug for treating hypercholesterolemia), and Herceptin (an antibody drug for treating Her2 positive breast cancer) were conjugated to PBI-5508 and purified to remove unconjugated reactants. The three conjugate preparations (Herceptin-PBI-5508, Praluent-PBI-5508, BSA-PBI-5508) were then incubated with D-cysteine to convert the CBT moieties to luciferin moieties that would be released as free D-luciferin after reduction of the TMQ moiety. The PBI-5508 conjugates as well as PBI-4312, a luciferin-TMQ derivative that was not conjugated to a protein, were then incubated with a luciferin detection reagent supplemented with a reductase enzyme (human diaphorase) and NADH for 15 minutes or for 1 hour. It was previously shown that these conditions release luciferin, but that luciferin is not released when the reductase/NADH is left out. The luciferin detection reagent contains ATP and UltraGlo luciferase and it produces light in proportion to the amount of free D-Luciferin present in the reaction mixture.

The stabilization against extracellular reductive release of a payload from a TMQ linker by tertiary conjugation to an antibody may provide an additional measure safety for conjugates bearing a cytotoxic agent.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. Any and all patents, patent applications, scientific papers, and other references cited in this application, as well as any references cited therein, are hereby incorporated by reference in their entirety.

What is claimed is:

1. A conjugate of formula (I), or a salt thereof, $$Cb\text{-}(G)_p \qquad (I)$$

wherein

Cb is a cell binding moiety;

p is a number from 1 to 20;

G is formula (II), (III), or (IV)

(II)

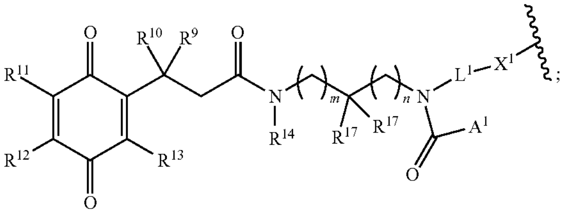

(III)

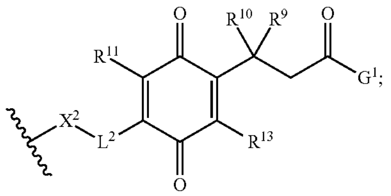

(IV)

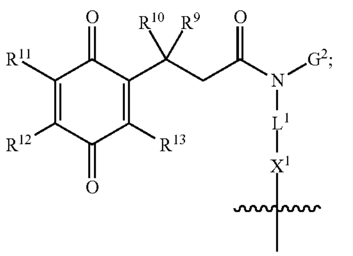

$R^9$ and $R^{10}$ are each independently selected from $C_{1-4}$alkyl;

$R^{11}$, $R^{12}$, and $R^{13}$ are each independently selected from the group consisting of H, $C_{1-4}$alkyl, $C_{1-4}$alkoxy, bromo, chloro, and amino, or $R^{11}$ and $R^{12}$ in formula (II) or (IV), together with the atoms to which they are attached form a fused phenyl ring;

$L^1$ is a first linker moiety;

$L^2$ is a second linker moiety;

$G^1$ is $-A^2$,

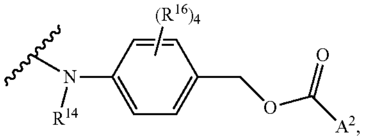

or

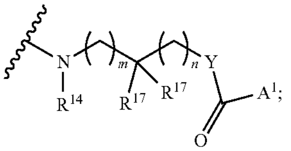

$G^2$ is

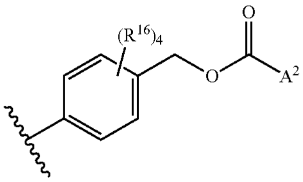

or

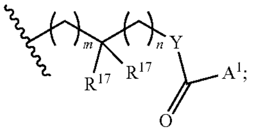

$X^1$ and $X^2$ are each an antibody-linking moiety;

Y is O or $NR^{15}$;

$R^{14}$ and $R^5$ are each independently H, $C_{1-30}$alkyl optionally substituted with 1-8 halogens, $-C_{1-30}$alkylene-OH, $-C_{1-30}$alkylene-$C_{1-4}$alkoxy, $-C_{1-30}$alkylene-COOH, or $-C_{1-30}$alkylene-amido;

$R^{16}$, at each occurrence, is independently H, halogen, $CH_3$, $OCH_3$, or $NO_2$;

$R^{17}$, at each occurrence, is independently H or $C_{1-4}$alkyl or both $R^{17}$ together with the carbon to which they are attached form a cycloalkyl ring having from 3-7 carbons;

m is an integer from 0-2;

n is an integer from 0-2;

$A^1$ is a payload moiety bonded through a substitutable oxygen or sulfur atom; and $A^2$ is a payload moiety bonded through a substitutable oxygen, sulfur, or nitrogen atom.

2. The conjugate of claim 1, or a salt thereof, wherein: $X^1$ or $X^2$ is

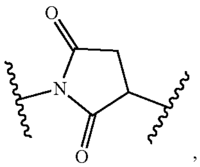

,

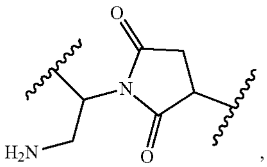

,

—C(O)$CH_2$—, —NHC(S)—, —NHC(O)—, —C(O)—, —$CH(SO_3H)$—C(O)—,

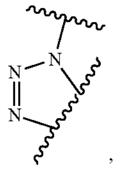,
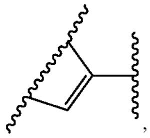,

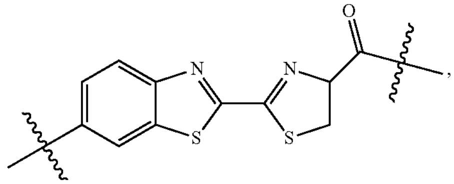,

—NH—, or —N($C_{1-6}$alkyl)-.

3. The conjugate of claim 1, or a salt thereof, wherein G is formula (II) or (IV);

$L^1$ is $L^{1a}$ or $L^{1a}$-$L^{1b}$, wherein $L^{1b}$ is bonded to $X^1$;

$L^{1a}$ is —$C_{1-12}$alkylene-, -($C_{2-6}$alkylene-O)$_x$—$C_{1-6}$alkylene-, or $C_{3-8}$cycloalkylene;

$L^{1b}$ comprises one or more covalently bonded divalent members, the one or more divalent members being selected from the group consisting of —$C_{1-6}$alkylene-, —$C_{2-6}$alkylene-O-, $C_{3-8}$cycloalkylene, —C(O)—, —O—, —S—, —S(O)—, —$S(O)_2$—, —$NR^{20}$—, —C($R^{21}$)═N—NH—, —CH($CO_2H$)—,

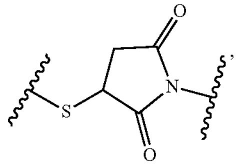 [SMILES: *SC1CC(=O)N(*)C1=O], an amino acid moiety, and phenylene;

wherein the $C_{3-8}$cycloalkylene and phenylene of $L^{1a}$ and/or $L^{1b}$ is optionally independently substituted with 1-4 substituents independently selected from the group consisting of $C_{1-4}$alkyl, $C_{1-4}$haloalkyl, $C_{1-4}$alkoxy, halo, cyano, and hydroxy;

$R^{20}$ and $R^{21}$ at each occurrence are independently hydrogen or $C_{1-4}$alkyl; and x is an integer from 1 to 20.

4. The conjugate of claim 3, or a salt thereof, wherein $L^{1b}$ is —C(O)$NR^{20}$-$L^{1c}$-, -cit-val-C(O)$C_{1-6}$alkylene-, —$NR_{20}$C(O)—, —$NR^{20}$C(O)-$L^{1c}$-, —$NR^{20}$C(O)O-$L^{1c}$-, -ala-val-C(O)$C_{1-6}$alkylene-, -cit-val-C(O)O-$C_{2-6}$alkylene-O-$C_{1-6}$alkylene-, -ala-val-C(O)O-$C_{2-6}$alkylene-(—$C_{1-6}$alkylene-, —S—S-$C_{1-6}$alkylene-, —NH—N═C($R^{21}$)-phenylene-O-$C_{1-6}$alkylene-,

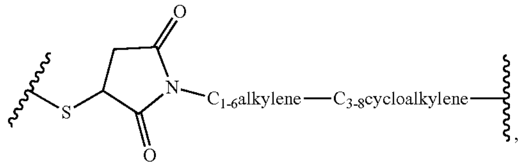, $C_{1-6}$alkylene-, —$C_{2-6}$alkylene-O—, or $C_{3-8}$cycloalkylene, and $L^{1c}$ is —$C_{1-6}$alkylene-, —$C_{1-6}$alkylene-$NR^{20}$C(O)—$C_{1-6}$alkylene-S—S-$C_{1-6}$alkylene-, —$C_{1-6}$alkylene-$NR^{20}$C(O)NH-N═C($R^{21}$)-phenylene-O-$C_{1-6}$alkylene-, $C_{3-8}$cycloalkylene, -($C_{2-6}$alkylene-O)—$C_{1-6}$alkylene-, —$C_{1-6}$alkylene-$C_{3-8}$cycloalkylene-, —$C_{3-8}$cycloalkylene-$C_{1-6}$alkylene-, —$C_{1-6}$alkylene-$C_{3-8}$cycloalkylene-$C_{1-6}$alkylene-, —$C_{1-6}$alkylene-S—S-$C_{1-6}$alkylene-, or

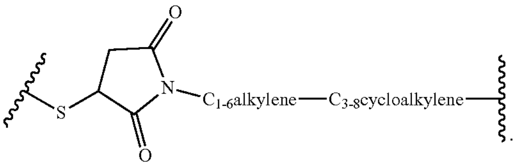.

5. The conjugate of claim 3, or a salt thereof, wherein $L^{1a}$ is -$(CH_2CH_2O)_{1-2}$—$CH_2CH_2$—;

$L^{1b}$ is —C(O)$NR^{20}$-$L^{1c}$-, -ala-val-C(O)$(CH_2)_5$—, -cit-val-C(O)$(CH_2)_5$—, or

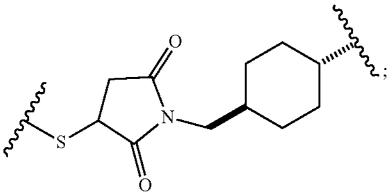;

and $L^{1c}$ is —$CH_2CH_2$—, —$CH_2CH_2$—$NR^{20}$C(O)—$CH_2CH_2$—S—S—$CH(CH_3)CH_2CH_2$—, —$CH_2CH_2$—$NR^{20}$C(O)NH—N═C($CH_3$)-1,4-phenylene-O—$CH_2CH_2CH_2$—, or

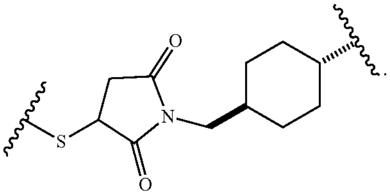.

6. The conjugate of claim 4, or a salt thereof, wherein: $L^{1b}$-$X^1$ is

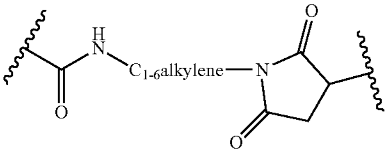,

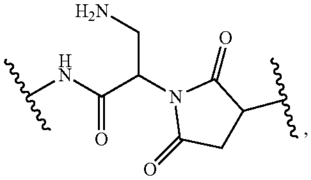,

-continued
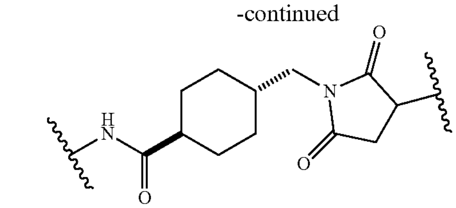
,
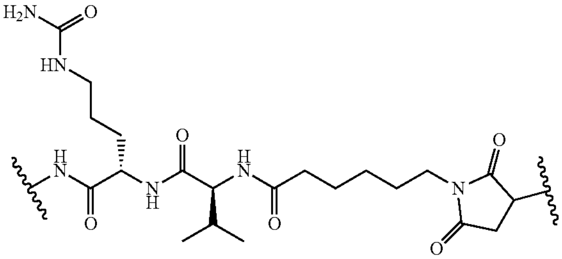
,
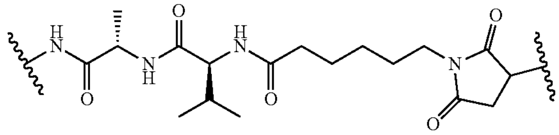
,
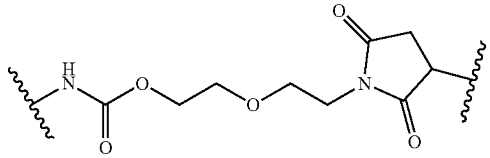
,
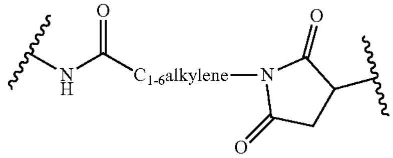
,
-continued
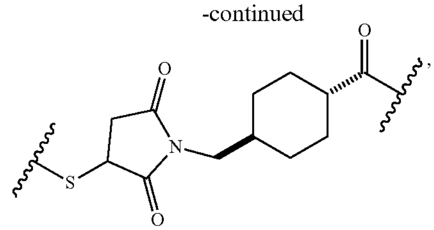
,
$-C(O)NR^{20}-C_{1-6}$alkylene-$NR^{20}C(O)-C_{1-6}$alkylene-S—S—$C_{1-6}$alkylene-C(O)—, $-C(O)NR^{20}-C_{1-6}$alkylene-$NR^{20}C(O)-C_{1-6}$alkylene-S—S—$C_{1-6}$alkylene-CH($SO_3H$)—C(O)—, $-C(O)NR^{20}-C_{1-6}$alkylene-$NR^{20}C(O)$NH—N=C($R^{21}$)-phenylene-O—$C_{1-6}$alkylene-C(O)—, or
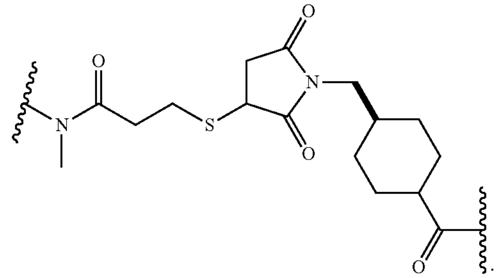
.
7. The conjugate of claim 3, or a salt thereof, wherein $L^1$-$X^1$ is:
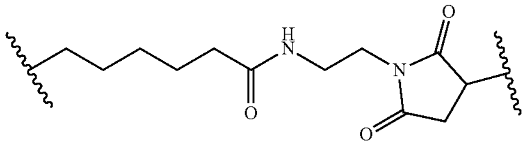
,
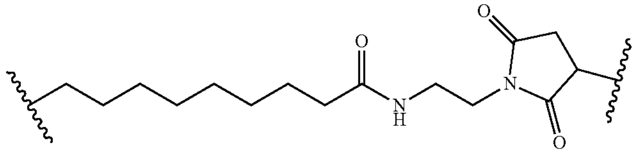
,
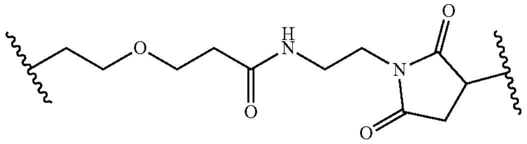
,
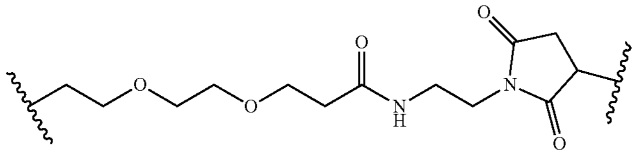
, -continued
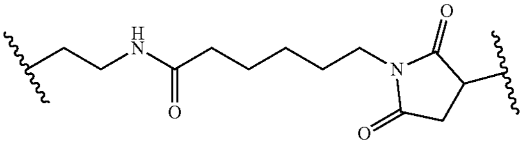,
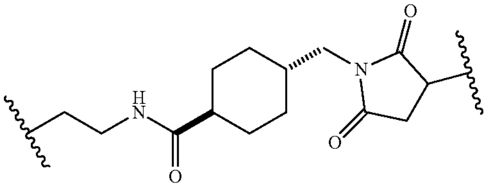,
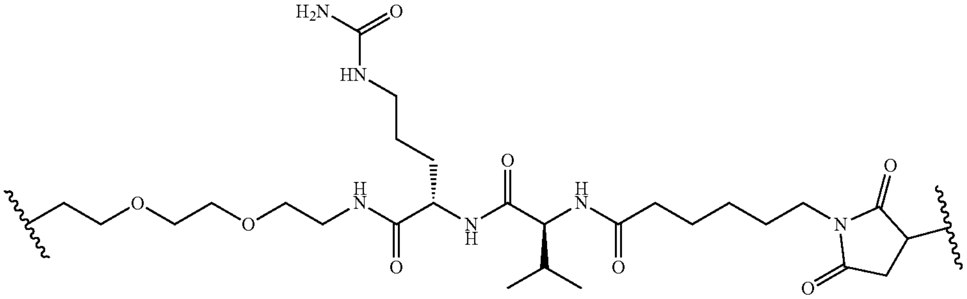,
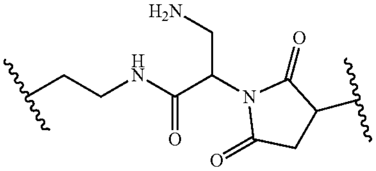,
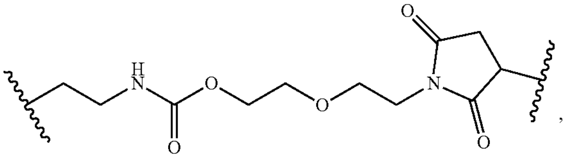,
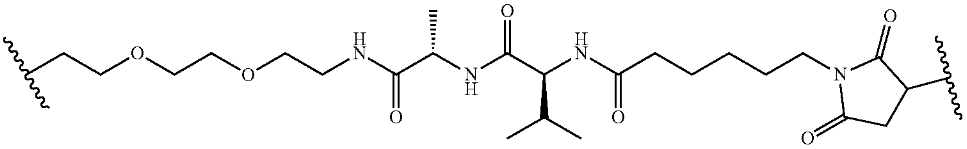,
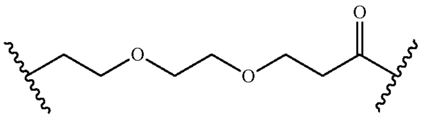,
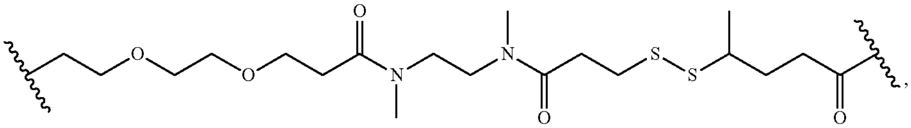,
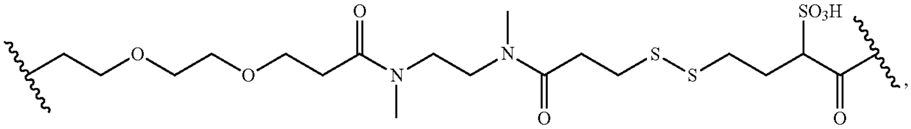,
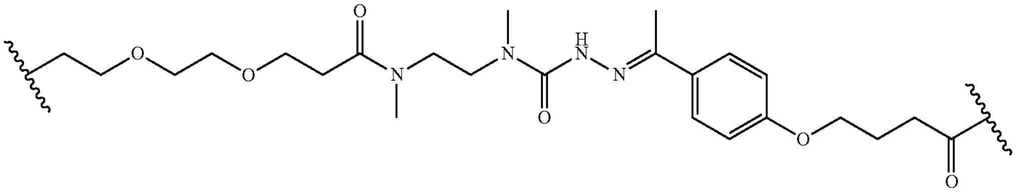, or
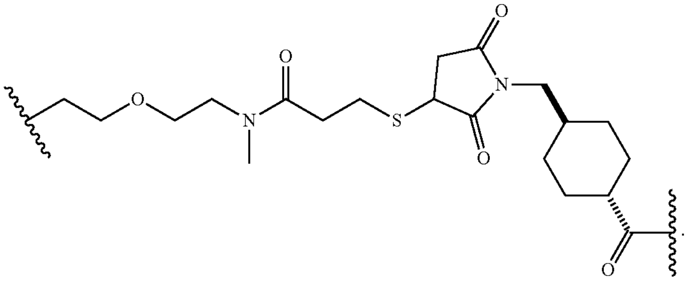.

8. The conjugate of claim 1, or a salt thereof, wherein G is formula (III);

$L^2$ is $L^{2a}$ or $L^{2a}$-$L^{2b}$, wherein $L^{2b}$ is bonded to $X^2$;

$L^{2a}$ is —$C_{2-6}$alkylene-;

$L^{2b}$ comprises one or more covalently bonded divalent members, the one or more divalent members being selected from the group consisting of —$C_{1-6}$alkylene-, —$C_{2-6}$alkylene-O—, $C_{3-8}$cycloalkylene, —C(O)—, —O—, —S—, —S(O)—, —$S(O)_2$—, —$NR^{30}$—, —$C(R^{31})$=N—N—, —$CH(CO_2H)$—,

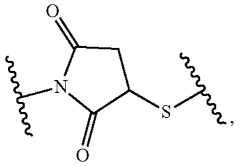 [SMILES: *SC1CC(=O)N(*)C1=O], an amino acid moiety, and phenylene;

wherein the $C_{3-8}$cycloalkylene and phenylene of $L^{1b}$ are optionally independently substituted with 1-4 substituents independently selected from the group consisting of $C_{1-4}$alkyl, $C_{1-4}$haloalkyl, $C_{1-4}$alkoxy, halo, cyano, and hydroxy; and $R^{30}$ and $R^{31}$ at each occurrence are independently hydrogen or $C_{1-4}$alkyl.

9. The conjugate of claim 8, or a salt thereof, wherein:

$L^{2b}$ is —$C(O)NR^{30}$-$L^{2c}$-, -cit-val-$C(O)C_{1-6}$alkylene-, —$NR^{30}C(O)$—, —$NR^{30}C(O)$-$L^{2c}$-, —$NR^{30}C(O)O$-$L^{2c}$-, -ala-val-$C(O)C_{1-6}$alkylene-, -cit-val-C(O)O-$C_{2-6}$alkylene-O-$C_{1-6}$alkylene-, -ala-val-C(O)O-$C_{2-6}$alkylene-O-$C_{1-6}$alkylene-, —S—S-$C_{1-6}$alkylene-, —NH—N=$C(R^{31})$-phenylene-O-$C_{1-6}$alkylene-,

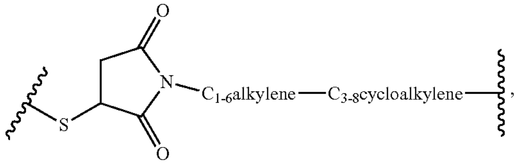, $C_{1-6}$alkylene-, —$C_{2-6}$alkylene-O—, or $C_{3-8}$cycloalkylene, and $L^{2c}$ is —$C_{1-6}$alkylene-, —$C_{1-6}$alkylene-$NR^{30}C(O)$—$C_{1-6}$alkylene-S—S-$C_{1-6}$alkylene-, —$C_{1-6}$alkylene-$NR^{30}C(O)NH$—N=$C(R^{31})$-phenylene-O-$C_{1-6}$alkylene-, —$C_{3-8}$cycloalkylene, —($C_{2-6}$alkylene-O)—$C_{1-6}$alkylene-, —$C_{1-6}$alkylene-$C_{3-8}$cycloalkylene-, —$C_{3-8}$cycloalkylene-$C_{1-6}$alkylene-, —$C_{1-6}$alkylene-$C_{3-8}$cycloalkylene-$C_{1-6}$alkylene-, —$C_{1-6}$alkylene-S—S-$C_{1-6}$alkylene, or

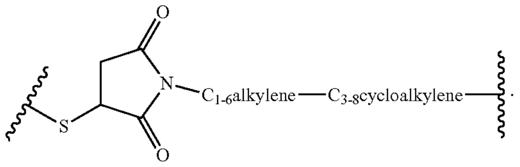.

10. The conjugate of claim 9, or a salt thereof, wherein:

$L^{2b}$-$X^2$ is

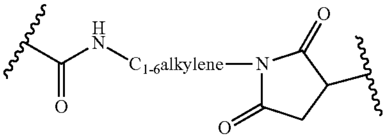,

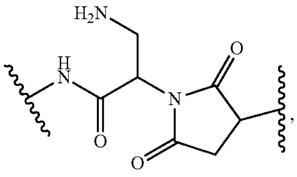,

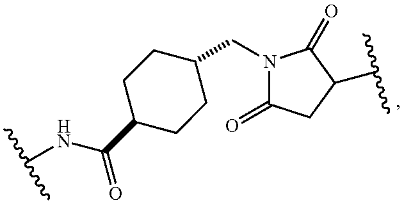,

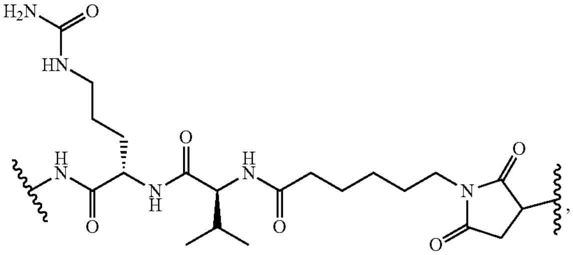,

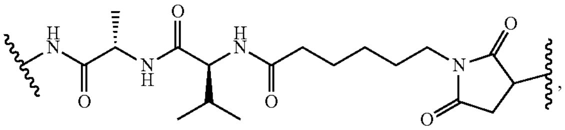,

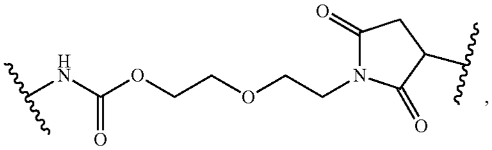,

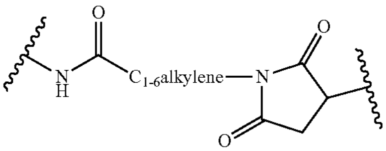,

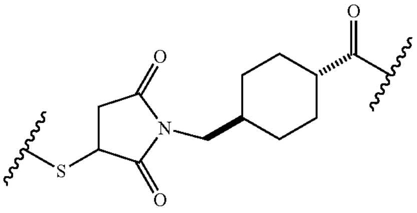,

—C(O)NR$^{30}$—$C_{1-6}$alkylene-NR$^{30}$C(O)—$C_{1-6}$alkylene-S—S—$C_{1-6}$alkylene-C(O)—, —C(O)NR$^{30}$—$C_{1-6}$alkylene-NR$^{30}$C(O)—$C_{1-6}$alkylene-S—S—$C_{1-6}$alkylene-CH($SO_3H$)—C(O)—, —C(O)NR$^{30}$—$C_{1-6}$alkylene-NR$^{30}$C(O)NH—N═C(R$^{31}$)-phenylene-O—$C_{1-6}$alkylene-C(O)—, or

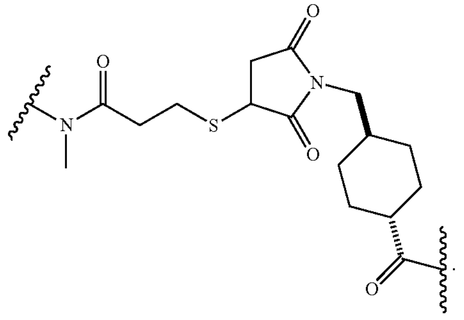

11. The conjugate of claim 1, or a pharmaceutically acceptable salt thereof, wherein $A^1$ and $A^2$ are a cytotoxic moiety.

12. The conjugate of claim 1, or a pharmaceutically acceptable salt thereof, wherein $A^1$ and $A^2$ are an anticancer drug moiety derived from a duocarmycin, a pyrrolobenzodiazepine, an auristatin, a doxorubicin, SN-38, or a maytansinoid.

13. The conjugate of claim 1, or a salt thereof, wherein the cell binding moiety is an antibody moiety, Ab.

14. The conjugate of claim 1, or a salt thereof, wherein the cell binding moiety is a small molecule drug moiety, and p is 1.

15. A pharmaceutical composition comprising the conjugate of claim 1, or a pharmaceutically acceptable salt thereof, and a pharmaceutically acceptable carrier.

16. A method of treating a proliferative disorder comprising administering a therapeutically effective amount of the conjugate of claim 1, or a pharmaceutically acceptable salt thereof, to a patient in need thereof.

17. A kit comprising the conjugate of claim 1, or a pharmaceutically acceptable salt thereof, and instructions for use.

18. The conjugate of claim 1, or a salt thereof, wherein $A^1$ and $A^2$ are a reporter moiety.

19. The conjugate of claim 18, or a salt thereof, wherein the reporter moiety comprises a bioluminescent reporter moiety, fluorescent reporter moiety, or colorimetric reporter moiety.

20. The conjugate of claim 19, or a salt thereof, wherein the bioluminescent reporter moiety comprises a substrate for a luciferase.

21. The conjugate of claim 19, or a salt thereof, wherein the fluorescent reporter moiety comprises a fluorophore.

22. The conjugate of claim 21, or a salt thereof, wherein the fluorophore is coumarin, R110, fluorescein, DDAO, resorufin, cresyl violet, silyl xanthene, or carbopyronine.

23. A method for evaluating cellular uptake of an agent, the method comprising:

a) contacting a sample with a conjugate of claim 18, or a salt thereof, wherein the sample comprises a cell; and b) detecting light emission, whereby the detection of light emission indicates cellular uptake of the agent.

24. The method of claim 23, wherein the cellular uptake of the agent results in the reduction of the conjugate and the generation of a released reporter moiety.

25. The method of claim 24, wherein the released reporter moiety comprises a fluorescent reporter moiety and wherein detecting light emission comprises exposing the sample to a wavelength of light and detecting fluorescence level in the sample, wherein an increase in fluorescence or a change in fluorescence wavelength as compared to the fluorescence or fluorescence wavelength of a control sample indicates cellular uptake of the agent.

26. The method of claim 25, wherein the control sample is a sample that is not contacted with a labeled agent or a sample that is incompetent for uptake of the agent.

27. The method of claim 24, wherein the reporter moiety comprises a bioluminescent reporter moiety.

28. The method of claim 27, wherein the bioluminescent reporter moiety comprises a substrate for a luciferase and detecting light emission comprises detecting the luminescence produced by the luciferase utilizing the released reporter moiety.

29. The method of claim 27, wherein the cell comprises a luciferase.

30. The method of claim 27, further comprising contacting the sample with a luciferase, and wherein detecting light emission comprises detecting the luminescence produced by the luciferase utilizing the released reporter moiety.

31. The method of claim 23, wherein the light emission is detected inside or outside the cell.

* * * * *